United States Patent [19]
Oshima et al.

[11] Patent Number: 6,071,393
[45] Date of Patent: Jun. 6, 2000

[54] NITROGEN OXIDE CONCENTRATION SENSOR

[75] Inventors: Takafumi Oshima, Nagoya; Masashi Ando, Nishi-kasugai-gun; Noboru Ishida, Kagamigahara; Satoshi Sugaya, Inuyama; Norihiko Nadanami, Kasugai, all of Japan

[73] Assignee: NGK Spark Plug Co., Ltd., Nagoya, Japan

[21] Appl. No.: 08/866,452

[22] Filed: May 30, 1997

[30] Foreign Application Priority Data

| | | | |
|---|---|---|---|
| May 31, 1996 | [JP] | Japan | 8-160812 |
| Nov. 29, 1996 | [JP] | Japan | 8-334987 |
| Dec. 2, 1996 | [JP] | Japan | 8-337520 |
| Dec. 3, 1996 | [JP] | Japan | 8-337483 |
| Dec. 18, 1996 | [JP] | Japan | 8-354135 |

[51] Int. Cl.$^7$ .................................................. G01N 27/407
[52] U.S. Cl. .......................... 204/425; 204/426; 204/427; 204/781; 204/783.5; 204/784.5
[58] Field of Search ................................. 204/421–429; 205/780.5, 781, 783.5, 784, 784.5, 785

[56] References Cited

U.S. PATENT DOCUMENTS

| | | | |
|---|---|---|---|
| 4,541,898 | 9/1985 | Mase et al. | 204/425 |
| 4,541,900 | 9/1985 | Mase et al. | 204/425 |
| 4,624,770 | 11/1986 | Yamada et al. | 204/425 |
| 4,634,514 | 1/1987 | Nishizawa et al. | 204/425 |
| 4,645,572 | 2/1987 | Nishizawa et al. | 204/425 |
| 4,722,779 | 2/1988 | Yamada et al. | 204/426 |
| 4,755,274 | 7/1988 | Mase et al. | 204/425 |
| 4,808,269 | 2/1989 | Kawanabe et al. | 204/425 |
| 4,824,548 | 4/1989 | Iino et al. | 204/425 |
| 4,824,549 | 4/1989 | Hamada et al. | 204/425 |
| 4,851,103 | 7/1989 | Usami et al. | 204/425 |
| 5,108,577 | 4/1992 | Mase et al. | 204/426 |
| 5,145,566 | 9/1992 | Logothetis et al. | 205/784 |
| 5,194,135 | 3/1993 | Hayakawa et al. | 204/425 |
| 5,217,588 | 6/1993 | Wang et al. | 204/426 |
| 5,288,389 | 2/1994 | Yamada et al. | 204/425 |
| 5,419,828 | 5/1995 | Nakano et al. | 204/426 |
| 5,474,665 | 12/1995 | Friese et al. | 204/426 |
| 5,549,804 | 8/1996 | Hotzel et al. | 204/426 |

FOREIGN PATENT DOCUMENTS

| | | |
|---|---|---|
| 0 259 093 | 3/1988 | European Pat. Off. . |
| 0 422 665 | 4/1991 | European Pat. Off. . |
| 0 678 740 A1 | 4/1995 | European Pat. Off. . |
| 0 678 740 | 10/1995 | European Pat. Off. . |
| 0 731 351 | 9/1996 | European Pat. Off. . |
| 8-14570 | 2/1996 | Japan . |
| 2288873 | 11/1995 | United Kingdom . |

OTHER PUBLICATIONS

N. Kato et al., "Performance of Thick Film NOx Sensor on Diesel and Gasoline Engines", SAE Technical Paper No. 970858, International Congress & Exposition, Detroit, Michigan, Feb. 22–27, 1997, pp. 199–206.

N. Kato et al., "Thick Film ZrO2 NOx Sensor", SAE Technical Paper No. 960334, Society of Automotive Engineers, Inc. 1996, pp. 137–142.

Primary Examiner—T. Tung
Attorney, Agent, or Firm—Morrison & Foerster

[57] ABSTRACT

A small-sized inexpensive nitrogen oxide concentration sensor capable of measuring the concentration of the nitrogen oxide in a measuring gas to a high accuracy. A first oxygen pumping cell, an oxygen concentration measuring cell and a second oxygen pumping cell are formed in different solid electrolyte layers of zirconia and electrodes of oxygen concentration measuring cell are isolated from electrodes of the oxygen pumping cells by insulating film.

12 Claims, 31 Drawing Sheets

OXYGEN CONCENTRATION IN EXHAUST GAS (TYPE 1-3)  (TYPE 4)

FIG. 22 A

STEP NO.

 1 PROTECTIVE PASTE 3

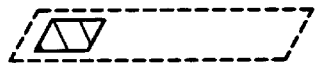 2 PT CONTAINING POROUS PASTE 4

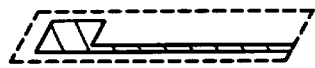 3 FIRST OXYGEN PUMPING ELECTRODE a; PASTE 1

 4 ZrO$_2$ SHEET (FIRST LAYER)

 5 INSULATING COATING PASTE 3

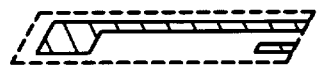 6 FIRST OXYGEN PUMPING ELECTRODE b; PASTE 2

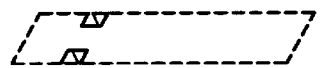 7 FIRST DIFFUSION APERTURE; PASTE 5

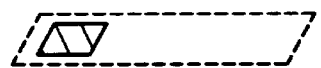 8 CARBON COATING PASTE 6

 9 13% PR WIRE ⌀0.2 x 7.5

 10 INSULATING COATING PASTE 3

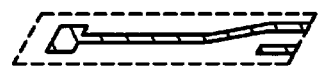 11 OXYGEN REFERENCE ELECTRODE a; PASTE 2

 12 INSULATING COATING PASTE 3

 13 ZrO$_2$ SHEET (SECOND LAYER)

 14 INSULATING COATING PASTE 3

A1 STAGE = 1 - 21     A2 STAGE = 22 - 27

FIG. 22 B

STEP NO.

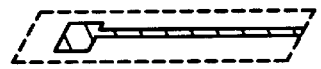  15  OXYGEN REFERENCE ELECTRODE b; PASTE 1

— 16  13% PR WIRE; $\phi\,0.2 \times 7.5$

  17  INSULATING COATING; PASTE 3

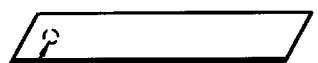  18  $ZrO_2$ SHEET (THIRD LAYER)

— 2nd DIFFUSION APERTURE

  19  INSULATING COATING; PASTE 3

— 20  13% PR WIRE; $\phi\,0.2 \times 7.5$

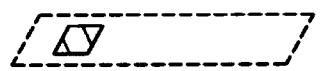  21  CARBON COATING PASTE 6

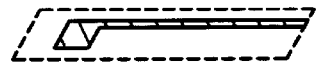  22  SECOND OXYGEN PUMPING ELECTRODE b; PASTE 1

  23  INSULATING COATING; PASTE 3

  24  $ZrO_2$ SHEET (FOURTH LAYER)

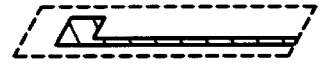  25  SECOND OXYGEN PUMPING ELECTRODE a; PASTE 1

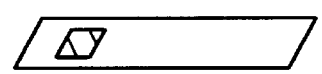  26  PT CONTAINING POROUS PASTE 4

  27  PROTECTIVE COATING PASTE 3

\* SECOND DIFFUSION APERTURE:
ALUMINA PELLET (1.3 DIAMETER x 0.8 THICKNESS)

A1 STAGE = 1 - 21        A2 STAGE = 22 - 27

FIG. 25
| STEPS B | STEP NO. | |
|---|---|---|
|  | 27b | INSULATING COATING; PASTE 3 |
|  | 28b | ALUMINA POROUS PASTE 5 |
|  | 29b | ZrO$_2$ SHEET (FIFTH LAYER) |
|  | 30b | PROTECTIVE COATING; PASTE 3 |
FIG. 22 [ 1 - 26 ] + (B) 27b - 30b RELATION OF Ip2 OFFSET v. OXYGEN CONCENTRATION RELATION OF Ip2 GAIN ($\triangle$Ip2) v. OXYGEN CONCENTRATION RELATION OF TEMPERATURE v. PUMP VP1 (mV)

HEATER POWER (W)

RELATION OF Ip2 v. OXYGEN CONCENTRATION

RELATION OF Ip2 v. GAIN ($\Delta$ Ip2) CONCENTRATION

FIG. 46
STEP 13d REPLACES STEP 13 IN FIG.22
STEP NO.
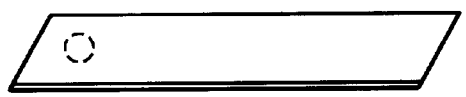
13d ZrO$_2$ SHEET
(SECOND LAYER)
D PROCESS STEPS 22d - 25d FOLLOW THE LAST STEP 21
OF PROCESS A1 IN FIG. 22
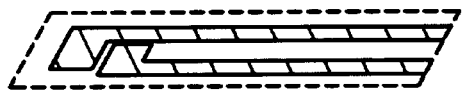
22d SECOND OXYGEN PUMPING
ELECTRODE a, b; PASTE 1
23d INSULATING COATING;
PASTE 3
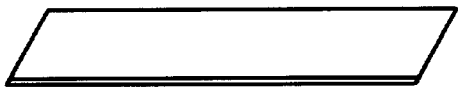
24d ZrO$_2$ SHEET
(FOURTH LAYER)
25d PROTECTIVE COATING ;
PASTE 3

NITROGEN OXIDE CONCENTRATION SENSOR

FIELD OF THE INVENTION

This invention relates to a nitride oxide concentration sensor for measuring the concentration of nitrogen oxide ($NO_x$), for instance as a component of exhaust gas of a combustor or an internal combustion engine, and a method for measuring the concentration. The objective measuring gas (gas to be measured) in accordance with the present invention includes exhaust gases of internal combustion engines used for vehicles such as car, ship or aircraft or for industrial application or combustion gases of a boiler or the like.

BACKGROUND

Recently, with intensification of exhaust gas regulations, studies for directly measuring the concentration of $NO_x$ contained in the exhaust gases of internal combustion engines for controlling the internal combustion engines or catalysts are on the progress. In particular, studies into a $NO_x$ gas concentration sensor of the type in which oxygen is pumped out by a first oxygen pumping cell, using a solid electrolyte (oxygen ion electro-conductive member), such as zirconia, to an extent that not permits decomposition of $NO_x$, and in which oxygen is further pumped out of the $NO_x$ containing residual gas by a second oxygen pumping cell for decomposing $NO_x$ and measuring a current $Ip_2$ generated by the dissociated oxygen ions to detect the $NO_x$ gas concentration, are conducted briskly because it is felt that such sensor can measure the $NO_x$ gas concentration without being affected by obstructive gases contained in the exhaust gas, such as HC or CO.

As a conventional nitrogen oxide concentration sensor, there is disclosed in, for example, SAE paper No. 960334, pages 137 to 142, 1996, a nitrogen oxide concentration sensor in which, in the inside of a laminate structure of solid electrolyte layers of thin plate-shaped zirconia, a first cavity having a first oxygen pumping cell and an oxygen concentration measuring cell, a second cavity having a second oxygen pumping cell, a first diffusion path for communicating the first cavity with the measuring gas side and a second diffusion path for communicating the first and second cavities with each other, are formed, as shown in a plan view of FIG. 3 and in an enlarged cross-sectional view of FIG. 4 taken along line A–A' of FIG. 3.

Referring to FIG. 4, 1 is the first diffusion path, 2 is the first cavity, 3 is the second diffusion path, 5-1, 5-2, 5-3, 5-4, 5-5 and 5-6 are laminated solid electrolyte layers of thin plate-shaped zirconia, 6 is the first oxygen pumping cell, 7 is the oxygen concentration measuring cell, 8 is the second oxygen pumping cell, 9 is an atmosphere inlet and 10 is a heater. The first oxygen pumping cell 6, oxygen concentration measuring cell 7 and second oxygen pumping cell 8 are provided with electrodes of porous platinum or porous rhodium 6-a, 6-b; 7-a, 7-b and 8-a, 8-b, respectively. In the present specification, the oxygen pumping cell and the oxygen concentration measuring cell are termed "oxygen cell".

In the present nitrogen oxide concentration sensor, the oxygen cells are maintained at constant temperatures by supplying a current to the heater 10. The measuring gas, such as an exhaust gas of the internal combustion engines, is introduced via the first diffusion path 1 into the first cavity 2. Oxygen is extracted (pumped out) by the first oxygen pumping cell 6 from the measuring gas introduced into the first cavity 2. The oxygen concentration in the first cavity 2 is monitored by the oxygen concentration measuring cell 7 so that oxygen is extracted up to a low oxygen concentration at which nitrogen oxides are not decomposed. The oxygen concentration is maintained at the resulting value.

The gas in the first cavity 2, maintained at this low oxygen concentration, is introduced via the second diffusion path 3 into the second cavity 4. From the measuring gas, introduced into the second cavity 4, oxygen is extracted by the second oxygen pumping cell 8. Since oxygen is extracted substantially completely by the second oxygen pumping cell 8 to achieve a lower oxygen concentration, and also since nitrogen oxides are completely decomposed into nitrogen and oxygen under the catalytic function of porous rhodium used as an electrode, oxygen produced on decomposition of nitrogen oxides are extracted by the second oxygen pumping cell 8. It is disclosed that, since the current value ($\mu A$) of the current flowing through the second oxygen pumping cell 8 has a linear relation with the concentration (ppm) of the nitrogen oxides contained in the measuring gas, the concentration of nitrogen oxides contained in the measuring gases may be measured if the correlation between the concentration of the nitrogen oxides and the pump current $Ip2$ is obtained in advance.

SUMMARY OF THE DISCLOSURE

According to the course of investigation toward the present invention, the following problems have been encountered.

The detected value of the nitrogen oxide concentration by this nitrogen oxide concentration sensor is not affected by the content of other possibly co-existing gases, such as CO, hydrocarbons, $CO_2$, $SO_2$ etc. However, the above detected value is affected to a more or less extent by oxygen contained in the measuring gas. Although this effect is not so large, it proves to be a significant error if the nitrogen oxides detected are of low concentration. On the other hand, since the solid electrolyte layer is heated to approximately 700° C. at the time of using the nitrogen oxide concentration sensor, the specific resistance of the solid electrolyte layer is lowered to a level of approximately several (or a few) hundred ohm-cm. Thus the conventional sensor having the electrodes of the oxygen concentration measuring cell and the second oxygen pumping cell which are provided on the same solid electrolyte layer suffers from a problem that the oxygen concentration measurement precision is low. This is believed to be ascribable to current leakage between the electrodes, such that the nitrogen oxide concentration is low in measurement accuracy resulting in that the oxygen concentration in the first cavity cannot be controlled accurately. The same holds for the nitrogen oxide concentration sensor disclosed in EPO 678740A1.

In the JP Patent Kokai JP-A-62-276453 (JP Patent Kokoku Publication JP-B-8-14570), there is disclosed an air/fuel ratio sensor having plural oxygen cells comprised of plural solid electrolyte layers 5-1, 5-2, 5-3 and 5-4 and porous electrodes 6-a, 6-b, 7-a, 7-b, 7-c, 8-a and 8-b, as shown in FIG. 5. This air/fuel ratio sensor has a first cavity 2 towards the first diffusion path 1 of an inlet portion of the measuring gas and a second cavity 4 communicating with a second diffusion path 3 having a gas diffusion resistance about twice that of the first diffusion path as compared to the first cavity 2. A pair of oxygen concentration measuring cells 7, 7' are provided in the first cavity 2 and in the second cavity 4 and are alternatively (separately from each other) used at a lean air/fuel ratio area and a rich air/fuel ratio area, respectively, for improving the oxygen concentration detection accuracy in the lean area. Also, it is envisaged to provide an air/fuel ratio sensor capable of accurately detecting the air/fuel ratio as found based on a detected value of the oxygen concentration for a prolonged perioıf of time by correcting changes with lapse of time of detection values of the oxygen concentration by taking advantage of the fact that the second diffusion path 3 is not clogged with particulate materials contained in the measuring gas, even if the first diffusion path is lowered in air permeability by the particulate materials. This applies to the case where the measuring gas is an exhaust gas of the internal combustion engine.

(1) It is a primary object of the present invention to provide a small-sized inexpensive nitrogen oxide concentration sensor capable of detecting the concentration of the nitrogen oxide in the measuring gas to a high accuracy.

It is a further object of the present invention to provide a method for detecting the concentration of the nitrogen oxide capable of detecting the concentration to a high accuracy at a practical level.

Further, the present inventors have found that, in a $NO_x$ gas concentration sensor in which an electrode outside the second measuring chamber of the second oxygen pumping cell is exposed to an exhaust gas atmosphere, the measured value of the $NO_x$ gas concentration (current $Ip_2$) exhibits significant dependency on changes in the oxygen concentration, or additionally on temperature changes, of the exhaust gas atmosphere such that there are occasions where the $No_x$ gas concentration cannot be measured accurately.

In view of the foregoing, it is a third object of the present invention to provide a $NO_x$ gas concentration sensor in which the measured value of the $NO_x$ gas concentration (current Ip2) exhibits dependency on changes in the oxygen concentration of the exhaust gas atmosphere to a lesser extent.

It is a fourth object of the present invention to provide a $NO_x$ gas concentration sensor in which the measured value of the $NO_x$ gas concentration (current Ip2) exhibits dependency on changes in the oxygen concentration and temperature of the exhaust gas atmosphere to a reduced extent. As such $NO_x$ gas concentration sensor, there is disclosed in the above-mentioned JP Patent Kokai Publication JP-A-62-276453 such a sensor in which the oxygen pumping out side of the second oxygen pumping cell is exposed to the exhaust gas.

However, the information acquired by the present inventors suggests that, since the oxygen pumping out side of the second oxygen pumping cell is exposed to the exhaust gases, the measured value of the $NO_x$ concentration depends significantly on changes in the oxygen concentration in the exhaust gases, such that it may be difficult to accurately measure the $NO_x$ concentration in a low oxygen concentration atmosphere.

In view of the foregoing, it is a fifth object of the present invention to provide a $NO_x$ concentration sensor capable of detecting the concentration of the $NO_x$ gas exhibiting a low oxygen concentration dependency.

Other objects of the present invention will become clear from the disclosure of the specification and the drawings in their entirety.

In connection with the above-mentioned first object, a nitrogen oxide concentration sensor according to an aspect A1 of the present invention has a first cavity comprising a first oxygen pumping cell and an oxygen concentration measuring cell, in which the first oxygen pumping cell has a solid electrolyte layer(e.g., of thin-plate shaped zirconia) having a pair of porous electrodes. Further, the sensor has a second cavity comprising a second oxygen pumping cell having a solid electrolyte layer(,e.g., of thin-plate shaped zirconia) having a pair of porous electrodes, a first diffusion path (resistance) for communicating the first cavity with the side of a measuring gas and a second diffusion path (resistance) for communicating the first cavity with the second cavity. According to aspect A1 the sensor has a feature that the first oxygen pumping cell, oxygen concentration measuring cell and the second oxygen pumping cell are provided in mutually different solid electrolyte layers, respectively. The pair of porous electrodes of the oxygen pumping cells are usually disposed on both sides of the electrolyte layer, typically sandwiching the electrolyte layer.

A method for measuring the concentration of the nitrogen oxide in an aspect A2 of the present invention typically employs a sensor according to aspect A1. The method comprises extracting oxygen from a first cavity by a first oxygen pumping cell while measuring the oxygen concentration by the oxygen concentration measuring cell from a measuring gas introduced via a first diffusion path into the first cavity, to a pre-set low oxygen concentration which does not substantially decompose the nitrogen oxide, introducing the resulting measuring gas set to a pre-set low oxygen concentration via a second diffusion path into a second cavity, extracting oxygen while a pre-set voltage is impressed across the second oxygen pumping cell provided in the second cavity to decompose the nitrogen oxide in the measuring gas in the second cavity, and measuring the concentration of the measuring gas based on a pumping current $Ip_2$ flowing at this time through the second oxygen pumping cell. The pump current is a minute current of, for example, the $\mu A$ order.

For accomplishing the third object, the present invention according to an aspect B provides following features. Namely, protection means (member) at least partially surrounding the electrode outside of the second measuring chamber (cavity) provided on the second oxygen pumping cell is provided for alleviating changes in the atmosphere in the vicinity of the electrode brought about by changes in the state of the measuring gas. Such changes in atmosphere include rapid changes in the oxygen concentration in the atmosphere, changes in temperature or changes in the flow of the atmosphere gas. The protective means may be provided for completely surrounding the electrode.

In the aforementioned $NO_x$ gas concentration sensor, the measuring current caused by $NO_x$ decomposition exhibits temperature and oxygen concentration dependency, thus obstructing accurate measurement of the $NO_x$ gas concentration.

According to an aspect C of the present invention, it is a fourth object to provide a $NO_x$ gas concentration sensor which has a low dependency to the temperature and oxygen concentration and enables precise measurement of the $NO_x$ concentration.

In connection with this object, the present inventors have found the following fact. Namely, if, in a $NO_x$ concentration sensor having a first measuring chamber (cavity) into which is introduced the measuring gas and a first oxygen pumping cell for pumping out oxygen from the first measuring chamber for controlling the oxygen concentration in the first measuring chamber to a constant value, the electrode of the first oxygen pumping cell is of substantially the same length as the first measuring chamber, there is produced a significant oxygen concentration gradient in the first measuring chamber, and hence an electromotive force (EMF) is produced on the electrode of the oxygen pumping cell in the vicinity of the distal end of the measuring chamber to affect measurement of the $NO_x$ gas concentration. The present inventors have conducted perseverant searches for improving this and arrived at the aspect C of the present invention.

For accomplishing the above-mentioned fourth object of the present invention, a $NO_x$ gas concentration sensor of the present invention, in aspect C, provides the following features. Namely, the measuring gas is introduced via a first diffusion resistance (path) into the first measuring chamber (cavity), and oxygen of the introduced gas is selectively pumped out of the first measuring chamber, wherein the ratio of the length of at least the electrode of the first oxygen pumping cell mounted on the wall surface of the first measuring chamber to the overall length of the first measuring chamber in the flowing direction of the measuring gas in the first measuring chamber is given by (electrode/overall length)=¼ to ¾.

As mentioned before, it is the fifth object of the present invention to provide a $NO_x$ concentration sensor capable of detecting the $NO_x$ gas concentration exhibiting a low oxygen concentration dependency.

In connection with the above object, the present inventors have found that a $NO_x$ gas concentration sensor of the type in which oxygen is pumped out by the first oxygen pumping cell to the extent that $NO_x$ is substantially not decomposed and oxygen is further pumped out by a second oxygen pumping cell from a residual gas containing $NO_x$ to decompose $NO_x$ for detection as the current has the following drawback. Namely, if the oxygen pumping out side of the second oxygen pumping cell is exposed to the exhaust gas atmosphere, (a) the electromotive force (EMF) generated in the second oxygen pumping cell depends on changes in the oxygen concentration in the exhaust gas atmosphere and (b) the current flowing across the electrodes of the second oxygen pumping cell ($NO_x$ gas concentration measuring current) $Ip_2$ depends on changes in the oxygen concentration in the exhaust gas since the relation "$Ip_2=(Vp_2-EMF)/R$" holds, where $Vp_2$ is the voltage applied across the second oxygen pumping cell for $NO_x$ decomposition, and R is resistance across the electrodes of the second oxygen pumping cell.

As a result of our further searches, the present inventors have found that the above inconveniences can be overcome by providing an electrode (oxygen pumping out side electrode) as a counter-electrode with respect to the electrode of the oxygen pumping cell in the second measuring chamber in the inside of the device (between layers of the laminated solid electrolyte) for pumping out oxygen via a lead part of the electrode or a portion thereof and exhausting the pumped out oxygen, via the following means.

Thus the sensor according to an aspect D of the present invention has the following features:

that of the paired electrodes of the second oxygen pumping cell, the electrode provided outside of the second measuring chamber (cavity) referred to hereinafter as "electrode of the second oxygen pumping cell provided outside of the second measuring chamber") is arranged so as not to be in direct contact with the atomsphere outside the sensor, and that diffusion resistance means discharging the oxygen with a diffusion resistance is provided around the electrode of the second oxygen ion pump cell provided outside of the second measuring chamber.

BRIEF DESCRIPTION OF THE DRAWINGS

FIGS. 22(A) and 22(B) illustrate the method for producing a nitrogen oxide concentration sensor embodying the present invention and a layout thereof.

FIG. 24A is a cross-sectional view taken along the long side of the sensor and FIG. 24B is a cross-sectional view taken along the plane of a porous diffusion layer and a protective layer protecting an electrode placed outside the second measuring chamber of the second oxygen pumping cell shown in FIG. 24A.

FIG. 25 illustrates the layout of a $NO_x$ gas sensor according to a further embodiment of the present invention.

FIGS. 29A, 29B and 29C are a cross-sectional view taken along the long side thereof, a plan view of a first measuring chamber and an enlarged schematic cross-sectional view of the first measuring chamber, respectively.

FIG. 46 illustrates a method for producing a $NO_x$ gas concentration sensor used for measurement and the layout thereof.

PREFERRED EMBODIMENTS

Figure 1:
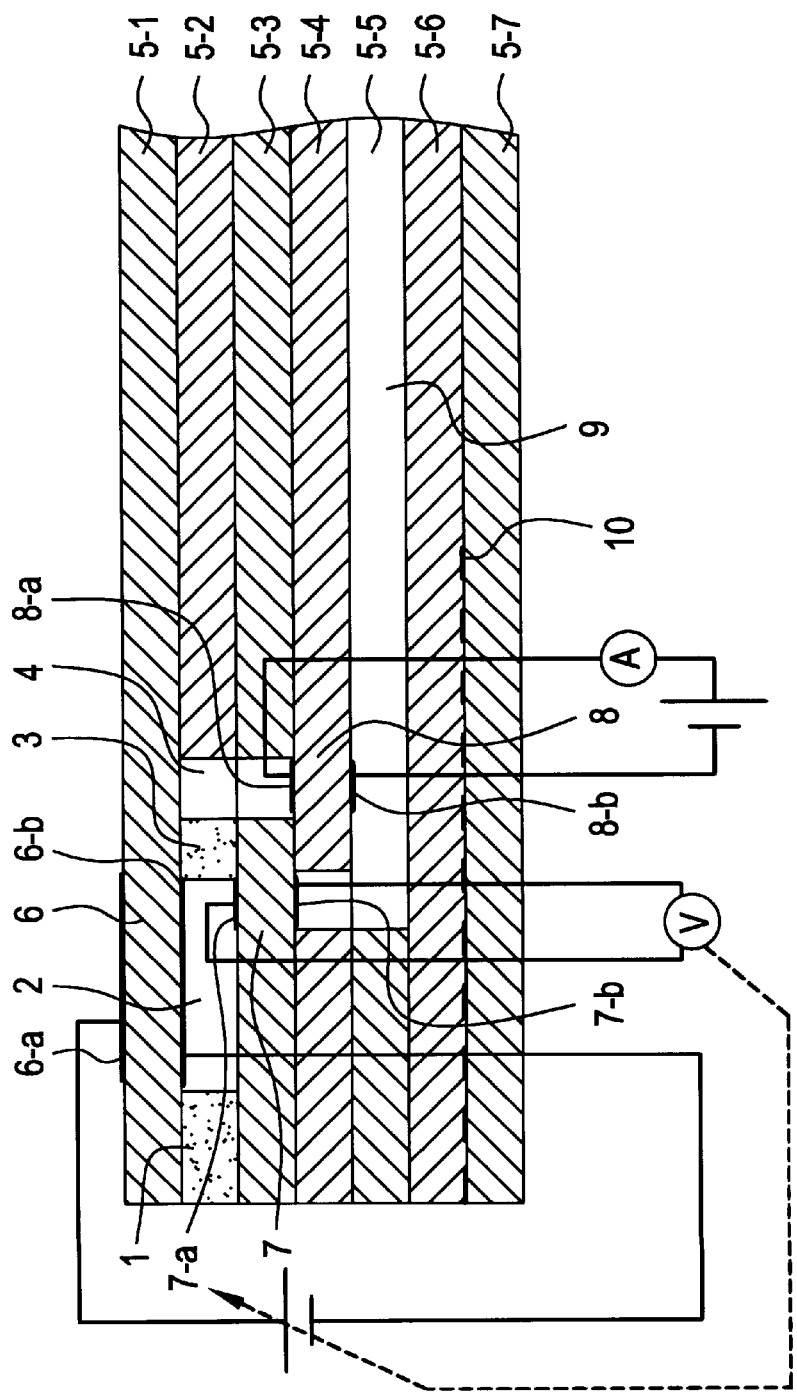
FIG. 1 is a longitudinal cross-sectional view showing an embodiment of a nitrogen oxide concentration sensor of the present invention.

Illustrative of the solid electrolytes of zirconia are solid solutions of zirconia and yttria and those of zirconia and calcia. In addition, solid solution of hafnia, that of perovskite type oxides or that of oxides of trivalent metals, may be used. As porous electrodes provided on the surface of the solid electrolyte, platinum, rhodium or alloys thereof having the catalytic function are preferably used. For producing the porous electrode, a thick film-forming method or plasma spraying may be employed. In the former method, a mixture of platinum powders with powders of the same material as a solid electrolyte is formed into a paste which is screen-printed on the solid electrolyte layer and fired to form a thick film. Alternatively, the above paste is plasma-sprayed onto the solid electrolyte layer for forming a film. If the electrode has a catalytic function, carbon monoxide or a hydrocarbon gas interfering with measurement of the nitrogen oxide tends to be decomposed by the catalytic action and removed. As the diffusion path, ceramics having fine through-holes or porous ceramics or a pressed or filled mass of ceramic powders are preferably used.

The nitrogen oxide concentration sensor according to the present aspect A1 is similar to the sensor described in the above-mentioned SAE paper No. 960334 in having in the inside of laminated solid electrolyte layers of thin plate-shaped zirconia a first cavity presenting a first oxygen pumping cell and an oxygen concentration measuring cell, a second cavity presenting a second oxygen pumping cell, a first diffusion path for communicating the first cavity with the measuring gas side and a second diffusion path for communicating the first cavity with the second cavity. However, the sensor according to the present aspect differs from the sensor of the SAE paper in that the electrode of the oxygen concentration measuring cell and the electrode of the second pumping cell are not provided on the same solid electrolyte layer.

By this difference, the nitrogen oxide concentration sensor of the present invention can control the oxygen concentration in the first cavity to high precision since the current leakage occurring between the electrodes of the oxygen concentration measuring cell and the second oxygen pumping cell is significantly decreased while the oxygen concentration in the first cavity is improved in measurement accuracy. Since the oxygen concentration in the first cavity can be stably controlled in this manner to a low level close to an oxygen concentration corresponding to the start of the decomposition of the nitrogen oxides in the first cavity, the concentration of nitrogen oxides contained in a trace amount in the exhaust gas is improved significantly. By applying the technique of producing a ceramic multi-layer substrate to the ceramic solid electrolyte material, it becomes possible to produce a small-sized nitrogen oxide concentration sensor of the present invention having the above structure inexpensively and with high productivity.

With a preferred nitrogen oxide concentration sensor of the present invention, the electrode(s) of the oxygen concentration measuring cell is (are) electrically isolated from the electrodes of the first pumping cell and the second oxygen pumping cell by an insulating film or an insulating layer provided between the sold electrolyte layers. In the conventional nitrogen oxide concentration sensor in which two or more oxygen concentration cells are provided in the solid electrolyte of the same layer, the electrodes are not completely isolated from each other. This, however, becomes possible with the nitrogen oxide concentration sensor of the present invention, such that current leakage between the electrodes can be prohibited completely by the insulating film or the insulating layer provided between the solid electrolyte layers.

With the above-described structure of the nitrogen oxide concentration sensor, the oxygen concentration measuring cell is improved in measuring accuracy such that the oxygen concentration in the first cavity can be controlled accurately. This further improves the measuring accuracy of the nitrogen oxide concentration in the nitrogen oxide concentration sensor to enable accurate detection of a low nitrogen oxide concentration. Although the insulating films may be provided between all of the solid electrolyte layers, it is desirable to provide the insulating films only between the solid electrolyte layers in need of isolation. In place of providing insulating films, insulating layer(s) of, for example, alumina may be substituted for solid electrolyte layer(s) not provided with an oxygen cell.

Another preferred nitrogen oxide concentration sensor according to the present invention has a second cavity charged with a porous material or porous powders. For example, the same porous material is charged into the second diffusion path and into the second cavity, so that the second cavity is reduced significantly in effective volume. If the second cavity is reduced significantly in effective volume, the nitrogen oxide concentration sensor is significantly improved in response characteristics to the nitrogen oxide. The capacity of the second cavity is preferably not more than 0.1 mm$^3$ or not more than 50% of the capacity of the first cavity.

With another preferred nitrogen oxide concentration sensor according to the present invention, the porous electrode of the second oxygen pumping cell provided on the side of the second cavity is formed of a metal selected form the group consisting of platinum, rhodium, palladium, iridium and rhenium, or alloys thereof, with other electrodes being formed of platinum or platinum alloy. In particular, since the porous electrode containing rhodium has a catalytic function of decomposing nitrogen oxides, nitrogen oxides in the second cavity can be completely decomposed without necessity of excessively raising the temperature of the sensor part of the sensor, such that the low nitrogen oxide concentration of an order of ppm (typically several or a few ppms) can be measured as current value of the second oxygen pumping cell. The porous electrodes provided in the first cavity are preferably metals selected from platinum, rhodium, palladium, iridium or rhenium, or alloys thereof, with at least one selected from Ag, Au, Ni, Co, Cr, Fe, Mn, Cu, Ti, Al, Pb, Zn, Sn and In.

In a further preferred nitrogen oxide concentration sensor of the present invention, the insulating film or layer is alumina ceramic, e.g. of high-purity alumina. The alumina ceramic exhibits excellent insulating properties under elevated temperatures, while it enables simultaneous firing with solid electrolyte layers of zirconia. In addition, the starting materials are available relatively with ease.

In a still further preferred nitrogen oxide concentration sensor of the present invention, the first cavity is substantially in register with the second cavity when the nitrogen oxide concentration sensor is viewed being projected in a direction perpendicular to the solid electrolyte layer, with the first cavity communicating with the second cavity by the second diffusion path extending through the solid electrolyte layer between the first and second cavities in a direction perpendicular to the solid electrolyte layers.

The nitrogen oxide concentration sensor of the above-described configuration has a merit that, if a rod-shaped sensor part is inserted into an exhaust gas conduit, flown through by an exhaust gas as measuring gases, via an aperture (hole) formed in the conduit, the distances of the sensor part from the conduit wall of the oxygen cells become substantially equal to one another, so that, if there is a temperature gradient due to thermal conduction in the long side direction of the sensor part, no temperature difference is produced between the oxygen cells, so that no errors are produced in the measured values. On the other hand, the sensors need to be maintained at elevated temperatures in order to permit decomposition of nitrogen oxides in the second cavity of the sensor. If the sensor part is constructed so that the cavities are in register with each other, the heat generating part of a heater having a planar heating part annexed for keeping up the temperature can be reduced in size. Since the distances of the oxygen cells from the conduit wall are equal, the sensor affected by the temperature difference due to thermal conduction through the sensor part or to temperature distribution in an exhaust pipe, thus facilitating control of the temperature of the oxygen cells of the sensor to a constant value.

In a nitrogen oxide concentration sensor according to a yet further embodiment of the present invention, plural layers each having a heater having a planar heat generating part are layered on laminated solid electrolyte layers, such that, when the nitrogen oxide concentration sensor is viewed being projected from a perpendicular direction on the solid electrolyte layer, the first cavity, second cavity and the planar heat generating part are all substantially in register with one another. The heater(s) is preferably layered substantially in register with one another for maintaining the temperature of the oxygen concentration measuring cell at a constant value so as to easily raise the temperature of the second cavity. The planar-shaped heat generating part is meant to include such a heat generating part in which heating wire or pattern is provided in an angled/meandered form on one plane. Two heaters, for example, may also be provided and a sensor unit provided in-between by way of providing a sandwich structure. If a gap or conduit communicating with the outside is provided between the heater and the solid electrolyte layer, it becomes possible to discharge the oxygen gas extracted by the pumping cells.

The lower the oxygen concentration, the lower becomes the decomposition temperature of the nitrogen oxide. In general, the heater annexed to the nitrogen oxide concentration sensor is preferably able to maintain the temperature of the oxygen concentration measuring cell at not lower than 700° C. The heater satisfying this condition preferably has its heat generating part formed of a composite material of ceramics, platinum or platinum alloy(s), while having its lead portion formed of platinum or platinum alloys. The lead portion of the heater has an ambient temperature resistance not higher than 30% of the ambient temperature resistance of the heater itself. If the lead portion has a reduced resistance value, it becomes possible to reduce the loss of the electrical energy used for heating the sensor.

The measuring method for measuring the nitrogen oxide concentration in the aspect A2 of the present invention has following features: That is, with the use of the nitrogen oxide concentration sensor according to the aspect A1, oxygen is extracted from the first cavity by the first pumping cell as the oxygen concentration is measured by the oxygen concentration measuring cell until reaching a low oxygen concentration at which nitrogen oxide is not decomposed from the measuring gas introduced via the first diffusion path into the first cavity. Meanwhile the resulting measuring gas lowered to a pre-set low oxygen concentration is introduced via the second diffusion path into the second cavity, and a pre-set voltage is impressed across the second pumping cell provided in the second cavity for extracting oxygen as the nitrogen oxide in the measuring gas in the second cavity is decomposed. Thus the concentration of the nitrogen oxide in the measuring gases is measured on the basis of a pump current $Ip_2$ flowing in the second oxygen pumping cell. The pump current Ip2 is a microcurrent, e.g., at the $\mu A$ order.

That is, the above-mentioned nitrogen oxide concentration sensor is used, and oxygen is extracted by the first oxygen pumping cell as the oxygen concentration is monitored by the oxygen concentration measuring cell up to a pre-set low oxygen concentration at which the nitrogen oxides are not decomposed from the measuring gas introduced via the first diffusion path into the first cavity. The measuring gas set to the pre-set low oxygen concentration after oxygen extraction, such as oxygen partial pressure of 0.1 Pa ($10^{-6}$ atm or approximately 100 ppm), are introduced via the second diffusion path into the second cavity. A pre-set voltage higher than that applied by first oxygen pumping cell provided in the first cavity, such as 450 mV, is applied across the second oxygen pumping cell provided in the second cavity for decomposing nitrogen oxides in the measuring gas introduced into the second cavity, as oxygen is extracted, and the concentration of the nitrogen oxides in the measuring gases is measured from the current value flowing through the second oxygen pumping cell. For providing a constant oxygen partial pressure, it suffices if the first oxygen pumping cell is controlled so as to assure a constant electromotive force (EMF) (e.g., 150 mV) of the oxygen measuring cell in the first cavity.

Although the voltage to be impressed across the second pumping cell is varied with the temperature in the second cavity, the type of the catalyst contained in the second cavity or with the type of the electrode of the second oxygen pumping cell etc., it is preferably such a voltage at which $CO_2$ or $H_2O$ is not decomposed, for example, 300 to 800 mV, so as to permit stable measurement of the nitrogen oxide concentration, if the temperature is 700° C. and the electrode is of porous rhodium (Rh).

The measuring method for measuring the nitrogen oxide concentration of the present aspect is high in measuring accuracy of the oxygen concentration measuring cell since the current leakage between the electrodes of the oxygen concentration measuring cell and the electrodes of other oxygen cells is smaller than with the conventional detection method, while there is no current leakage between the electrodes due to insulation between the electrodes by the insulating films or layers, thus assuring high measuring accuracy of the oxygen concentration measuring cell. owing to the high measuring accuracy of the oxygen concentration measuring cell, the oxygen concentration in the first cavity can be controlled highly accurately to a pre-set low concentration at which nitrogen oxides are not decomposed, so that the measuring gases containing the nitrogen oxides of low oxygen concentration may be fed from the second diffusion path to the second cavity in order to decompose the nitrogen oxides in the measuring gases for accurately detecting the nitrogen oxides from the intensity of the current flowing in the second cavity. The detection value obtained by this detection method is not varied with the concentration of intervening gas (gas components) other than oxygen in the measuring gas. The fluctuations in the measured value due to the oxygen concentration in the measuring gas are not significant.

In another preferred detection method for nitrogen oxides according to the present aspect, the effect of the oxygen concentration in the measuring gas on detection values of the concentration of the nitrogen oxides is corrected on the basis of data measured using a reference gas having different known oxygen concentration and nitrogen oxide concentration. This enables correction in the fluctuations in the detected values by the concentration of oxygen contained in the measuring gas, resulting in a further improved accuracy of $NO_x$ detection.

In another preferred method for measuring the nitrogen oxides according to the present aspect, the data is given as the following relations (i) to (iii):

(i) the relation between the oxygen concentration of the measuring gas and the pumping current $Ip_2$ of the first oxygen pumping cell when the oxygen concentration in the first cavity is maintained by the first oxygen pumping cell at a low oxygen concentration at which the nitrogen oxide is not decomposed, during which the oxygen concentration in the first cavity is monitored by the oxygen concentration measuring cell using the reference gas;

(ii) the relation between the $O_2$ concentration at a zero nitrogen oxide concentration and the pump current $Ip_2(\mu A)$ of the second oxygen pumping cell extracting oxygen from the second cavity; and (iii) the relation between the concentration of nitrogen oxide (ppm) as found of the reference gas having an oxygen concentration of the same level as the measuring gas and the nitrogen oxide concentration different from the measuring gas and the pump current $Ip_2$ of the second oxygen pumping cell. Since these data are variable depending on the design parameters of the sensor, manufacturing fluctuations, such as sensor setting temperatures, air permeability of the first diffusion path and the second diffusion path, ratio thereof, the capacity (volume) of the first cavity and the second cavity, or ratio thereof etc., it is preferred that measurement data be previously found for each sensor.

In another preferred method for detecting nitrogen oxides according to the present aspect, it is assumed that, even if the oxygen concentration in the measuring gases is changed, a pre-set functional relation, such as a linear relation, exists between the nitrogen oxide concentration (ppm) and the pump current $Ip_2$ ($\mu A$). Then, based on the above data stored in advance in a micro-computer memory, the nitrogen oxide concentration is found and corrected by processing by a micro-computer. These results can be displayed on a display or outputted on a recorder. If the processing for correcting the measured value is carried out by a micro-computer annexed to the detector, the measured and corrected values having high accuracy can be obtained on a real-time basis. The corrected detection value can be displayed or recorded, while the measured value can be fed back to the controller of a combustor, such as an internal combustion engine, for controlling the operating state of the combustor.

Figure 16:
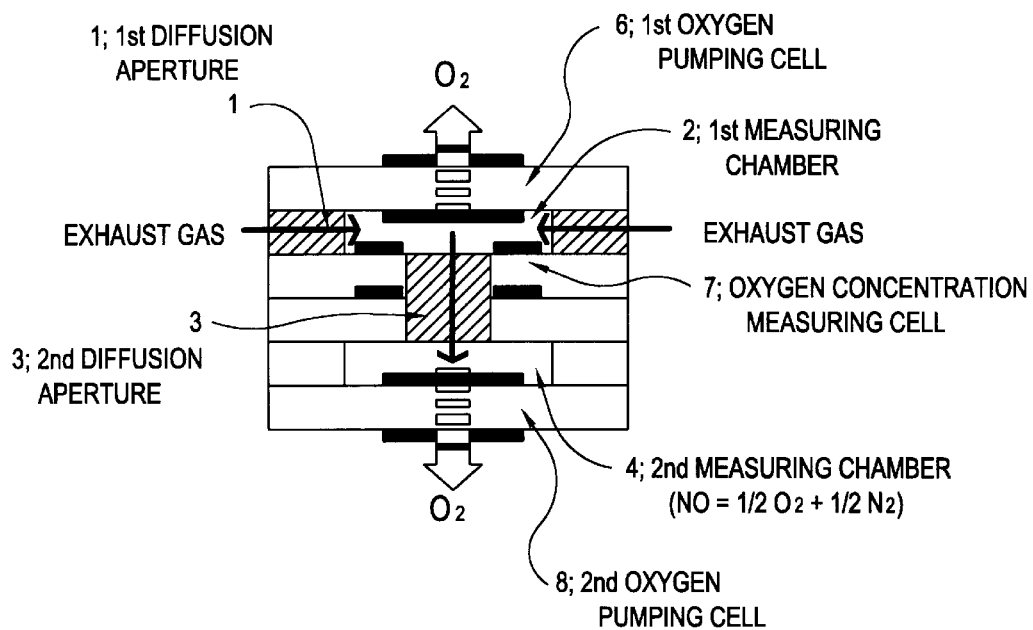
FIG. 16 is a schematic structural view for illustrating the measuring principle of a nitrogen oxide concentration sensor according to an embodiment of the present invention, with the sensor being shown as it is cut along its short side.

The principle of measurement by a nitrogen oxide concentration sensor according to an embodiment in an aspect A3 of the present invention will be now explained. FIG. 16 is a cross-sectional view taken along a short-side direction of the sensor for illustrating the measurement principle of a nitrogen oxide concentration sensor embodying the present invention. The sensor shown in FIG. 16 includes a laminate of layers: i.e., a layer of a first oxygen pumping cell 6 having a solid electrolyte layer and a pair of oxygen pumping electrodes on both sides of the solid electrolyte layer, a layer of a first measurement chamber (first cavity or space) 2, a layer of an oxygen concentration measuring cell 7 having a solid electrolyte layer and a pair of oxygen partial pressure detection electrodes on both sides of the solid electrolyte layer, a solid electrolyte layer, a layer of a second measuring chamber (second cavity or space) 4, and a layer of a second oxygen pumping cell 8 having a solid electrolyte layer and a pair of oxygen pumping electrodes on both sides of the solid electrolyte layer, in this order. In addition, a first diffusion aperture (first diffusion path) 1 is provided on both sides of the first measuring chamber 2, while a second diffusion aperture (second diffusion path) 3 is provided for being passed through the layer of the oxygen concentration measuring cell 7 and the solid electrolyte layer for communicating the chambers 2, 4 with each other.

The principle of measurement by the nitrogen oxide concentration sensor shown in FIG. 16 will be explained. First, (a) exhaust gas is diffused through the first diffusion aperture 1 into the first measuring chamber 2. (b) By the first oxygen pumping cell 6, the oxygen in the exhaust gases flowing into the first measuring chamber 2 by the first oxygen pumping cell 6 is pumped out insofar as $NO_x$ is not decomposed. At this time, the oxygen partial pressure in the first measuring chamber 2 is controlled to a constant value by driving the first oxygen pumping cell 6 based on an output signal of an oxygen partial pressure detecting electrode (electrode of the oxygen concentration measuring cell 7). (c) The concentration-controlled $O_2$ gas and $NO_x$ gas are diffused from the first measuring chamber 2 via second diffusion aperture 3 into the second measuring chamber 4. (d) By the oxygen in the second measuring chamber 4 in the second oxygen pumping cell 8 being pumped out the oxygen concentration in the second measuring chamber 4 is lowered to an extent sufficient for starting the dissociation of $NO_x$ so that the $NO_x$ gas in the second measuring chamber 4 is decomposed into $N_2$ and $O_2$. Since the value of the pump current $Ip_2$ flowing in the second oxygen pumping cell 8 is correlated substantially linearly with the value of the $NO_x$ concentration, the $NO_x$ concentration can be measured by measuring the value of $Ip_2$, so that it becomes possible to measure the concentration of the nitrogen oxide in the exhaust gases. By providing an oxygen partial pressure detection electrode and the oxygen pumping electrode in different solid electrolyte layers in the nitrogen oxide concentration sensor, the leakage current ceases to flow between the electrodes. Since the residual oxygen concentration in the first measuring chamber 2 can be measured more accurately, the $NO_x$ concentration can be detected more reliably on the basis of the concentration of oxygen derived from $NO_x$ decomposition.

Figure 17:
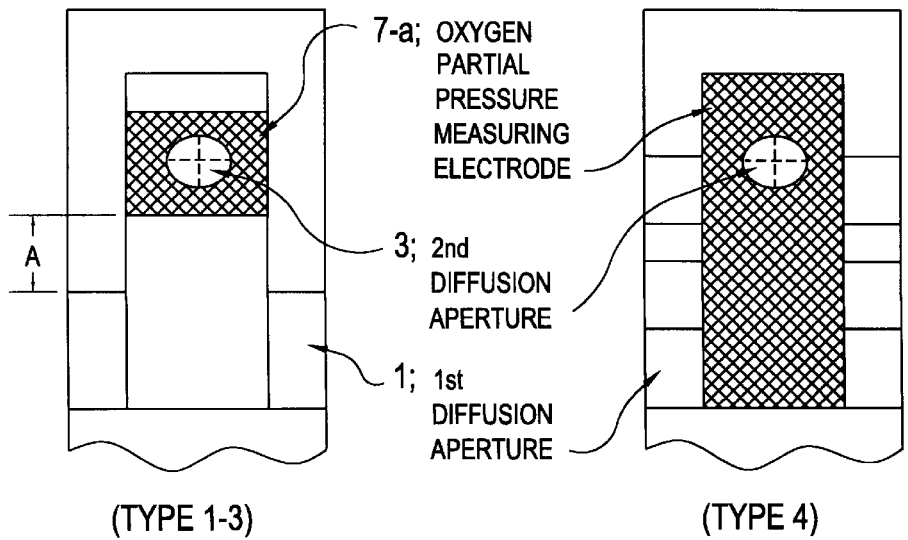
FIG. 17 shows the cross-section taken along the surface of a solid electrolyte layer of a first measuring chamber, into which flows the measuring gas, for illustrating the schematic structure of a nitrogen oxide concentration sensor according to an embodiment and a further modification (Embodiment A5), with the left side half and the right side half showing a $NO_x$ sensor (nitrogen oxide concentration sensor) of the present embodiment and a $NO_x$ sensor of a Comparative Embodiment (Comparative Embodiment A2).

Referring to FIG. 17, another embodiment in the aspect A3 of the present invention will be explained. FIG. 17 shows the cross-section taken along the surface of the solid electrolyte layer of the first measuring chamber (first diffusion path or first diffusion speed-regulator). On the left and right sides of FIG. 1 are shown a $NO_x$ sensor of the present embodiment (nitrogen oxide concentration sensor) and a $NO_x$ sensor of the Control Example. The principle of the $NO_x$ sensor of the present embodiment is explained by comparison of these two sensors. First, in the $NO_x$ sensor of the Control Example on the right side of FIG. 17, four first diffusion apertures (first diffusion paths) 1 for flowing the measuring gas into the first measuring chamber 2 are formed in the vicinity of the second diffusion aperture (second diffusion path) 3. An oxygen partial pressure detection electrode 7-a is provided in contact with the first diffusion aperture 1 over substantially the entire bottom surface of the first measuring chamber 2 (with a length longer than the entire length of the first measuring chamber 2). On the other hand, in the $NO_x$ sensor of the embodiment of the present invention shown on the left side of FIG. 17, two diffusion apertures 1 are formed at a significant (or substantial) distance from the second diffusion aperture 3, while the oxygen partial pressure detection electrode 7-a is smaller in area than the entire bottom surface of the second measuring chamber 2, that is shorter than the entire length of the first measuring chamber,that is provided only in part, and at a pre-set distance from the first diffusion aperture 1 only around or in the vicinity of the second diffusion aperture. This feature of the $NO_x$ sensor of the present embodiment that 'the diffusion aperture 1 is formed at a significant (or substantial) distance from the second diffusion aperture 3, while the oxygen partial pressure detection electrode 7-a is smaller in area than the entire bottom surface of the second measuring chamber 2, that is shorter than the entire length of the first measuring chamber (that is, provided only in part) and at a pre-set distance from the first diffusion aperture 1 only around or in the vicinity of the second diffusion aperture', is also the feature possessed by a $NO_x$ sensor shown in FIG. 15, which will be explained later.

In the information acquired by the present inventors, the following four facts have been found. First, in a $NO_x$ sensor, the oxygen concentration in the first measuring chamber is substantially represented by an average value of the oxygen concentration present on the oxygen partial pressure detection electrode. Therefore, even granting that the oxygen concentration is locally low in the first measuring chamber, the oxygen concentration in the first measuring chamber is controlled responsive to the average value of the concentration of oxygen present on the oxygen partial pressure detection electrode, so that, if an oxygen concentration higher than the actual value is detected, excess oxygen is pumped out of the first measuring chamber such that $NO_x$ decomposition is likely to occur in the first measuring chamber.

Second, the oxygen concentration in the vicinity of the first diffusion aperture in the first measuring chamber is thought to be higher than in the remaining portion of the first measuring chamber. Therefore, if the oxygen concentration in the vicinity of the first diffusion aperture affects the detection of the oxygen concentration by the oxygen partial pressure detection electrode, the voltage across the first oxygen pumping cell is raised automatically. Such rise in the impressed voltage is not desirable since it usually gives rise to 'blackening' in the solid electrolyte layer formed of zirconia.

Third, if the output of the oxygen partial pressure detection electrode is low in following-up property to changes in the conditions of the measuring gas, such as changes in the oxygen concentration in the exhaust gas of a diesel engine amounting to 4 to 18%, control of the first oxygen pumping cell having the output as an input parameter cannot be optimized. The result is that the concentration of the residual oxygen sent from the first measuring chamber to the second measuring chamber is varied so that it may become impossible to make accurate measurement of the $NO_x$ concentration in the second measuring chamber.

Fourth, if the oxygen concentration in the first measuring chamber is set to a higher value for prohibiting decomposition of $NO_x$ or prohibiting 'blackening' in the first measuring chamber, a larger offset is tolerated in the measurement of the nitrogen oxide concentration in the second measuring chamber. Such 'offset' raises the temperature dependency and oxygen concentration dependency of the measurement of the nitrogen oxide concentration.

If the $NO_x$ sensor of the Control Example shown on the right side of FIG. 17 is verified on the basis of the first to fourth facts, the oxygen partial pressure detection electrode 7-a is significantly large in size as compared to the bottom surface area of the first measuring chamber 2 (wall surface area of the first cavity in which is formed the second diffusion aperture), and moreover the electrode 7-a is disposed adjacent to the first diffusion aperture 1, such inconvenience may arise that the nitrogen oxide concentration cannot be measured accurately, as mentioned above. Conversely, with the $NO_x$ sensor of the embodiment on the left side of FIG. 17, since the oxygen partial pressure detection electrode 7-a is sufficiently smaller in size than the area of the entire bottom surface of the first measuring chamber 2 and is disposed at a spacing from the first diffusion aperture 1 only around or in the vicinity of the second diffusion aperture 3, and thus the inconvenience proper to the $NO_x$ sensor of the Control Example is resolved in its entirety. Preferably, the distance on the same plane between the electrode of the oxygen concentration measuring cell and the (internal) exit of the first diffusion path is set so as to be substantially 1.5 mm or longer. In the present invention, the description of the range of numerical figures includes both upper and lower limits and optional intermediate values.

EXAMPLES

The present invention will now be explained with reference to drawings of Examples of the invention. The present invention is however not limited to these merely illustrative Examples.

Example A1

FIG. 1 is a longitudinal cross-sectional view showing an end part of a nitrogen oxide concentration sensor according to an embodiment of the present invention. In this figure, 1 is a first diffusion path, 2 a first cavity, 3 a second diffusion path, and 4 a second cavity. 5-1 to 5-7 denote solid electrolyte layers of thin plate-shaped zirconia. 6 is a first oxygen pumping cell, and 6-a, 6-b are porous electrodes of the first oxygen pumping cell. 7 is an oxygen concentration measuring cell, and 7-a, 7-b are porous electrodes of the first oxygen concentration measuring cell. 8 is a second oxygen pumping cell, and 8-a, 8-b are porous electrodes of the second pumping cell. 9 and 10 are an atmospheric air inlet and a heater, respectively.

Figure 3:
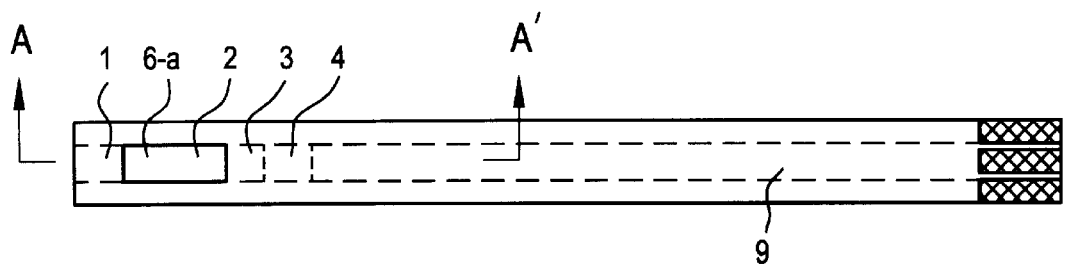
FIG. 3 is a plan view showing an example of a conventional nitrogen oxide concentration sensor.
Figure 4:
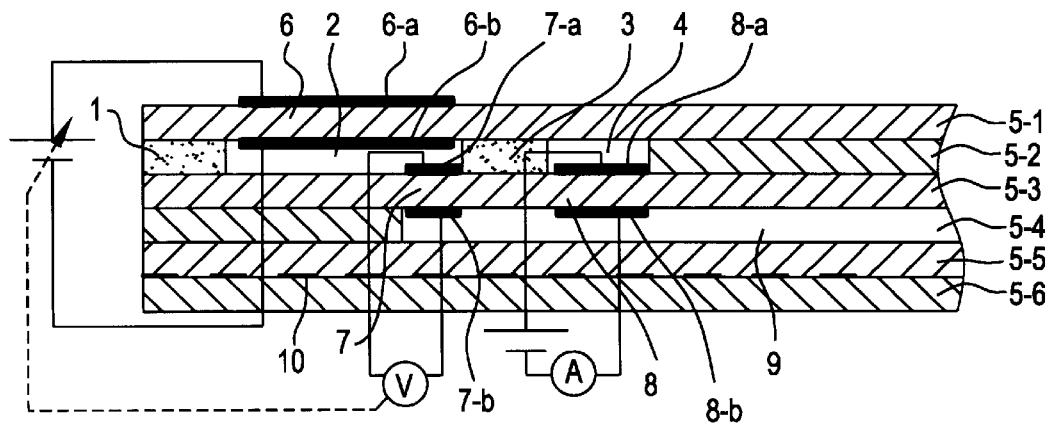
FIG. 4 is an enlarged cross-sectional view of the nitrogen oxide concentration sensor taken along line A–A' of FIG. 3.
Figure 5:
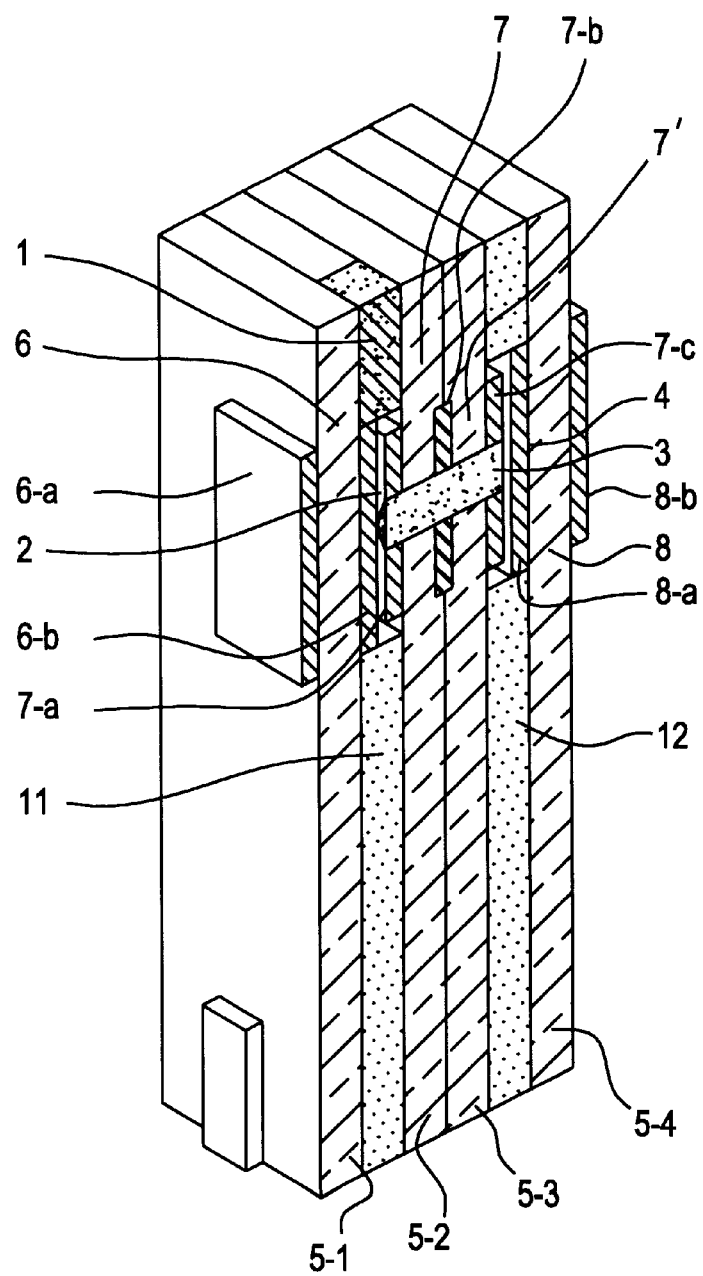
FIG. 5 is a perspective view showing the cross-section of a conventional air/fuel ratio sensor at a mid portion.

The nitrogen oxide concentration sensor shown in FIG. 1 differs from the conventional nitrogen oxide concentration sensor shown in FIGS. 3 and 4 in that the oxygen concentration measuring cell 7 and the second oxygen pumping cell are provided in different solid electrolyte layers 5-3 and 5-4. Since the oxygen cells are provided in the different solid electrolyte layers in the nitrogen oxide concentration sensor of the present invention, the current leakage between the electrodes of the oxygen cells is only little thus raising the accuracy with which the oxygen concentration is measured by the oxygen concentration measuring cell 7. The oxygen concentration in the first cavity 1 is monitored by the oxygen concentration measuring cell 7 at the same time as the nitrogen oxide in the first cavity 2 is controlled to a lower oxygen concentration at which the oxygen concentration in the first cavity 2 is not decomposed, for example, to approximately 100 ppm. Since the oxygen concentration in the first cavity can be stably controlled in this manner, the nitrogen oxide concentration in the measuring gas with the low nitrogen oxide concentration can be detected with high accuracy.

That is, the measuring gases with the low oxygen concentration are sent via the second diffusion path 3 to the second cavity 4. From the measuring gas in the second cavity 4, oxygen is extracted by the second pumping cell 8. If the oxygen concentration in the second cavity 4 is lowered to a value at which the nitrogen oxides are decomposed, the decomposition reaction of $2NO_x \rightarrow N_2 + XO_2$ occurs to yield $O_2$ which is extracted by the second oxygen pumping cell 8. Since the major portion of $O_2$ extracted at this time is $O_2$ generated by the above decomposition reaction, the concentration of nitrogen oxides in the measuring gases can be detected by measuring the current flowing in the second oxygen pumping cell.

For decomposing NO without lowering the oxygen concentration in the second cavity 4 to a value which decomposes $CO_2$ or $H_2O$, a constant voltage of, for example, 450 mV, is impressed across the second oxygen pumping cell 8. With this method for measuring the nitrogen oxide concentration, since the current flowing in the second oxygen pumping cell 8 is variable by, for example, temperatures of the measuring gas, the first oxygen pumping cell 6 and the second oxygen pumping cell 8, gas diffusion resistance in the first and second diffusion paths 1 and 3, oxygen concentration set in the first cavity 2 or the set voltage of the second oxygen pumping cell 8, a standard gas having a previously known gas concentration is used for calibration. The nitrogen oxide concentration sensor has, for instance, a height (size in a direction perpendicular to the solid electrolyte layer) of 1.7 mm, a width of 3.5 mm and a length of 7 mm.

If a voltage applied across the second oxygen pumping cell 8 is set appropriately for selectively decomposing gases other than $NO_x$, such as $CO_x$, $H_2O$ or HC, the present method may be applied to measurement of the other gases. If these setting conditions are stored in a micro-computer, multi-component gases, such as $O_2$, $NO_x$, $H_2O$ or $CO_2$ may be measured by a sole sensor.

Example A2

Figure 2:
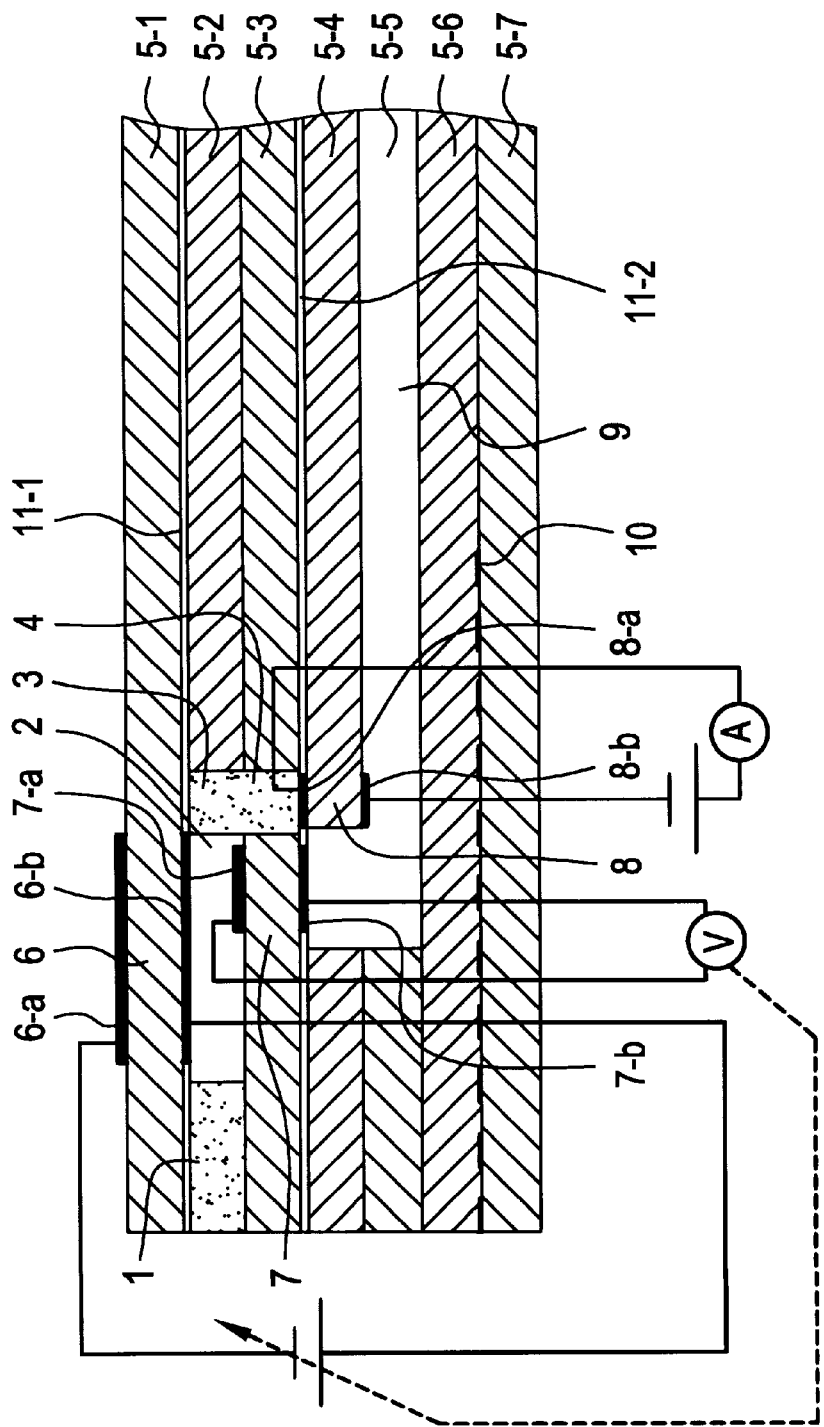
FIG. 2 is a longitudinal cross-sectional view showing a modification of a nitrogen oxide-concentration sensor of the present invention.

Example A2 shown in FIG. 2 differs from Example A1 of FIG. 1 in that insulating films 11-1 and 11-2 are arranged between the solid electrolytes 5-1 and 5-2 and between the solid electrolytes 5-3 and 5-4, and in that the second cavity 4 is charged with a porous material. In the second embodiment, the parts or components having the same functions as those of Example A1 are depicted by the same numerals and the corresponding description is omitted for simplicity (hereinafter the same). In the present embodiment, since the insulating film 11-1 of high purity alumina ceramic with a thickness of 20 to 30 μm are interposed between the solid electrolyte layers for completely prohibiting the leak current from flowing between the electrodes 7-a and 7-b of the oxygen concentration measuring cell 7 and electrodes 8-a and 8-b of the oxygen concentration measuring cell 8, the oxygen concentration measuring cell 7 has a high measuring accuracy, so that the oxygen concentration in the first cavity 2 can be stably maintained at a low constant value. Thus it becomes possible to measure nitrogen oxides with a high accuracy even if the nitrogen oxide concentration is low.

Example A3

Figure 6:
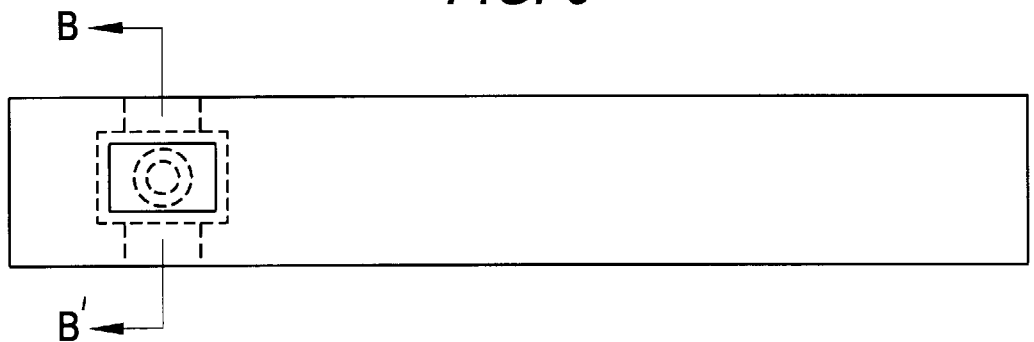
FIG. 6 is a plan view showing another embodiment of a nitrogen oxygen sensor according to the present invention.
Figure 7:
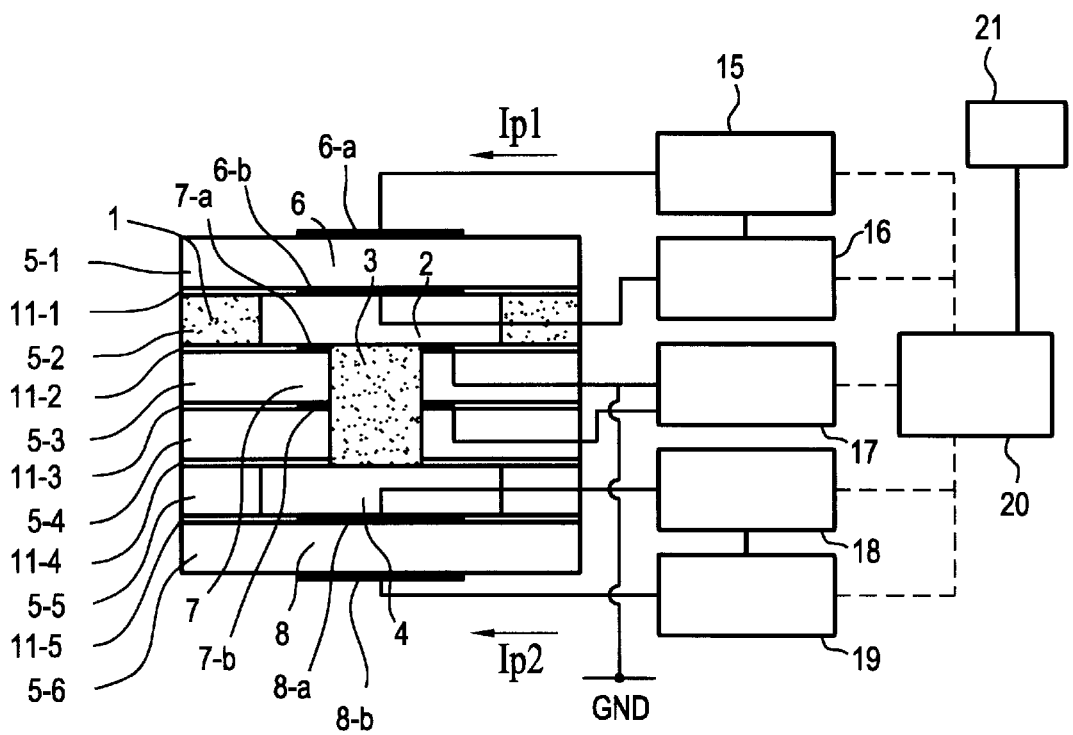
FIG. 7 is a block diagram of a control system annexed to an enlarged cross-sectional view taken along line B–B' of FIG. 6.

FIG. 6 is a plan view of another example of a nitrogen oxide concentration sensor according to the present invention, that is Example A3. This sensor has a height in the direction perpendicular to the solid electrolyte layer of 1.5 mm, a width of 3.5 mm and a length of 5 mm. FIG. 7 is a transverse cross-sectional view taken along line B–B' of the Example of FIG. 6. The present embodiment differs from Example A1 in that the first cavity 2 and the second cavity 4 are arranged substantially in register (overlapping) with each other in the vertical direction. Also, the present Example differs from Example A1 in that the first diffusion path 1 is provided on both sides of the sensor instead of on the distal end side of the sensor, and in that the insulating films 11-1, 11-2, 11-3 and 11-5 are interposed each between the solid electrolyte layers 5-1, 5-2, 5-3, 5-4, 5-5 and 5-6, with the electrodes of the oxygen cells being insulated from each other. Although the second cavity 4 is not charged with the porous material, the second cavity 4 may also be charged with the porous material, as in Example A2 described above. In FIG. 7, there is also annexed a micro-computer 20 having a power source unit 15 and an ammeter 16 of the first oxygen pumping cell 6, a potentiometer 17 of the oxygen concentration measuring cell 7, a power source unit 19 and an ammeter 18 of the second oxygen pumping cell 8 and a recorder 21. A reference oxygen concentration of the present sensor is kept in communication via a pre-set diffusion resistance with outside air by the fact that the electrode 7-b and its leads are porous. If a constant small current is allowed to flow in the oxygen concentration measuring cell 7, the electrode 7-b can be used as a self-generating reference electrode. The self-generating reference electrode has a merit that the reference oxygen concentration is not influenced by changes in the oxygen concentration in air.

Example A4

Figure 8:
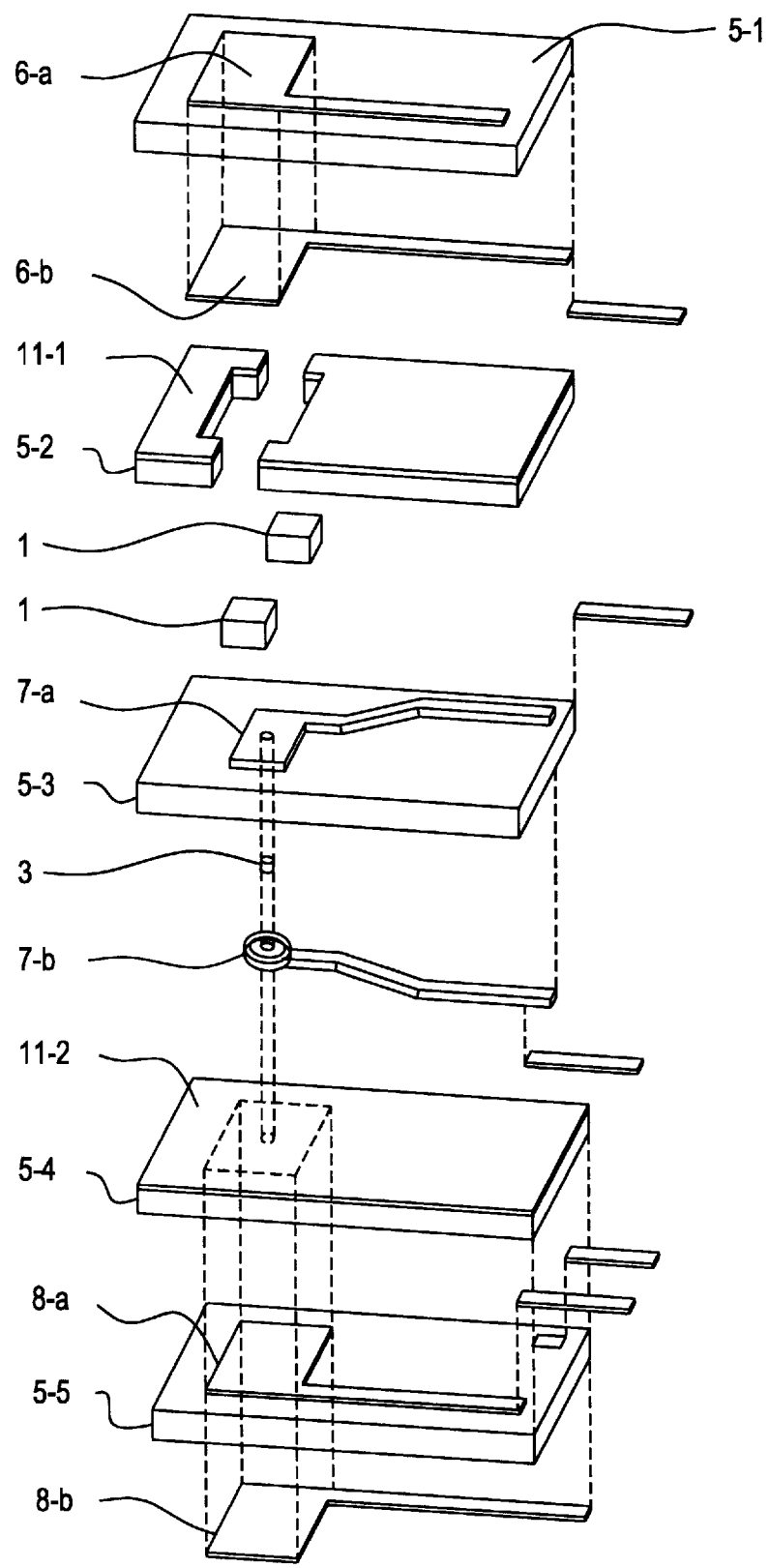
FIG. 8 is a perspective view of the layout for manufacturing the nitrogen oxide concentration sensor of FIG. 6.

FIG. 8 shows, in perspective, an illustrative layout for manufacturing a nitrogen oxide concentration sensor embodying the present invention. If a minute constant current is allowed to flow through the oxygen concentration measuring cell 7, the electrode 7-b may be used as a self-generating reference electrode.

Figure 9:
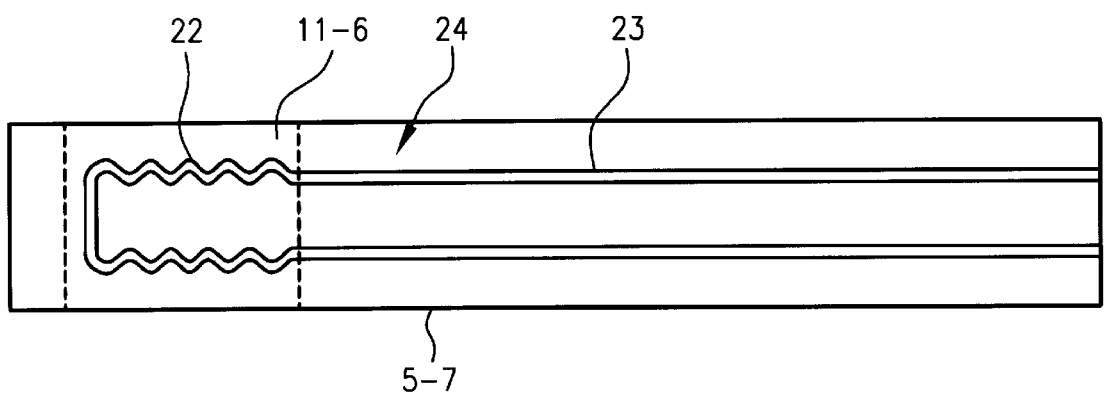
FIG. 9 is a plan view showing a heater mounted on the nitrogen oxide concentration sensor of FIG. 6.

FIG. 9 shows a heater used by being laminated on the nitrogen oxide concentration sensors of FIGS. 6 and 8. This heater 24 is made up of a heat generating part 22 of an alumina-platinum composite material screen-printed on a solid electrolyte layer 5-7 and a platinum lead wire 23. This heater 24 is laminated below and consolidated to a sensor shown for example in FIG. 6. When viewed being projected on the solid electrolyte layer in a vertical direction, the heat generating part 22 is substantially in register with the first cavity 2 and the second cavity 4. In the present Example, the heater 24 is embedded in the insulating film 11-6 of high-purity alumina ceramic and is insulated from the electrode of the second oxygen pumping cell.

Test Example A1

Figure 10:
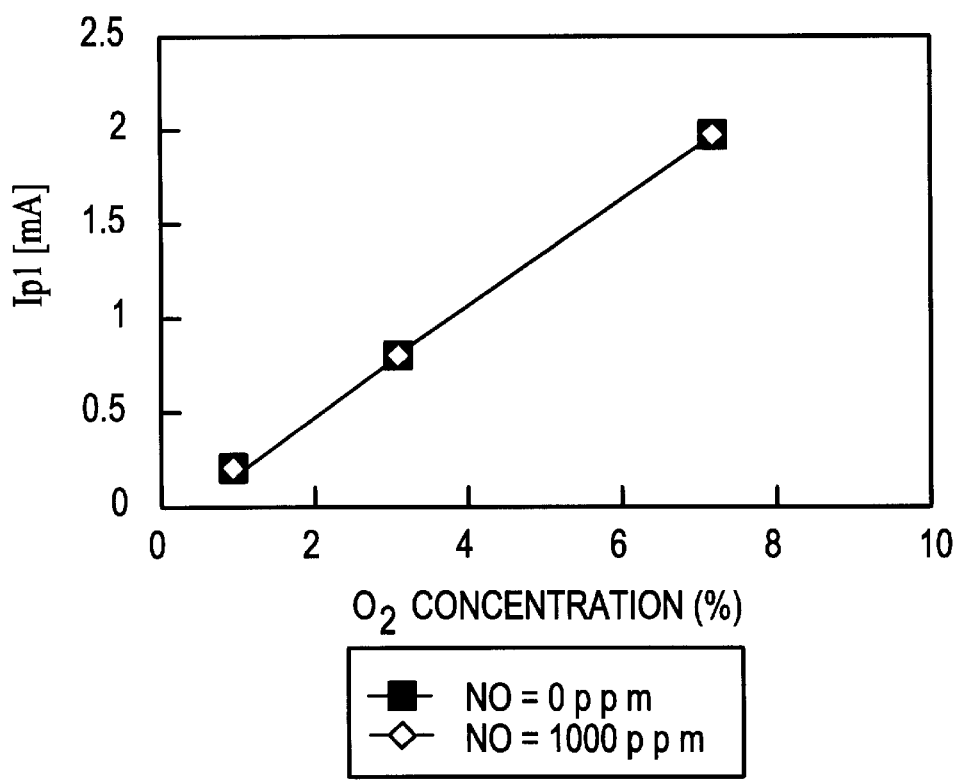
FIG. 10 is a chart showing the correlation between the pump current $IP_1$ of the first oxygen pumping cell and the nitrogen oxide concentration in the measuring gases for different nitride oxygen concentrations in the nitrogen oxide concentration sensor according to an embodiment of the present invention (the configuration shown in FIG. 2).

A method of measuring nitrogen oxides in a measuring gas maintained at 1 atmosphere, using the nitrogen oxide concentration sensor of Example A2 (having the configuration of FIG. 2), is now explained. FIG. 10 is a graph showing the relation between the pump current $Ip_1$ (mA) flowing in the first oxygen pumping cell and the oxygen concentration in the measuring gas when the first oxygen pumping cell is controlled for maintaining the oxygen concentration in the first cavity at 1 ppm, provided that the nitrogen oxide concentration in a measuring gas containing 10% of $CO_2$ introduced into the first cavity at a gas temperature of 500° C. and a sensor temperature of 760° C. is varied to 0 ppm and 1000 ppm, with an oxygen concentration being 7%, 3% and 1% (with the remaining gas being nitrogen).

Figure 11:
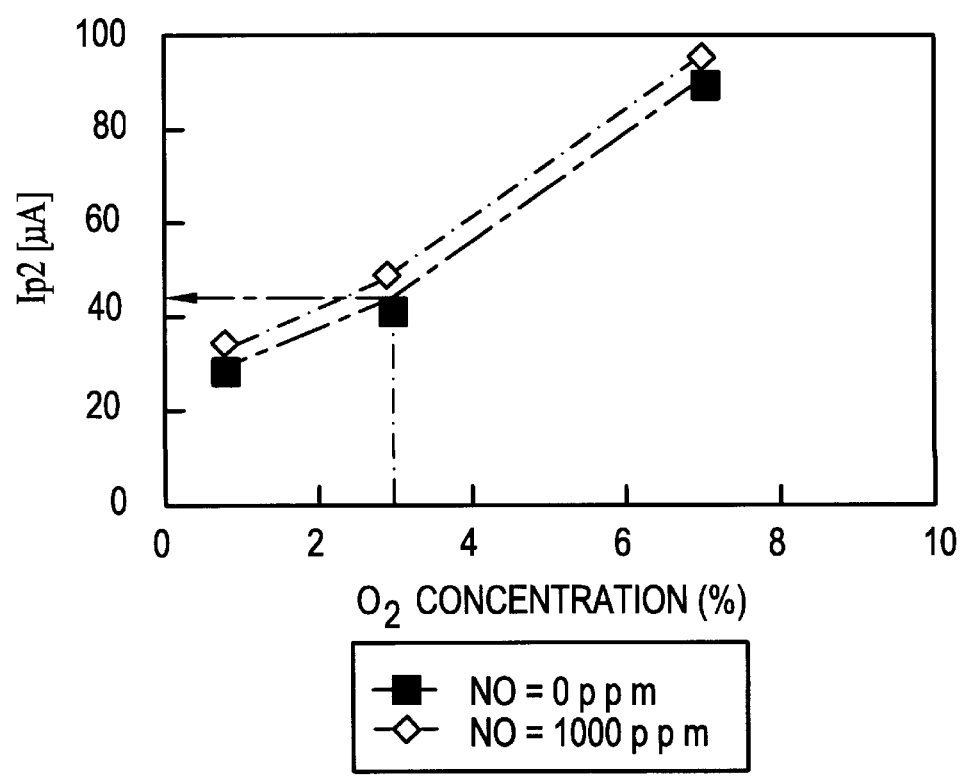
FIG. 11 is a graph showing an illustrative correlation between the pump current $IP_1$ and the oxygen concentration when a voltage of 450 mV is applied across the second pumping cell for various values of the oxygen concentration and the nitrogen oxide concentration, with the use of the nitrogen oxide concentration sensor according to the modified embodiment of the present invention (the configuration shown in FIG. 2).
Figure 12:
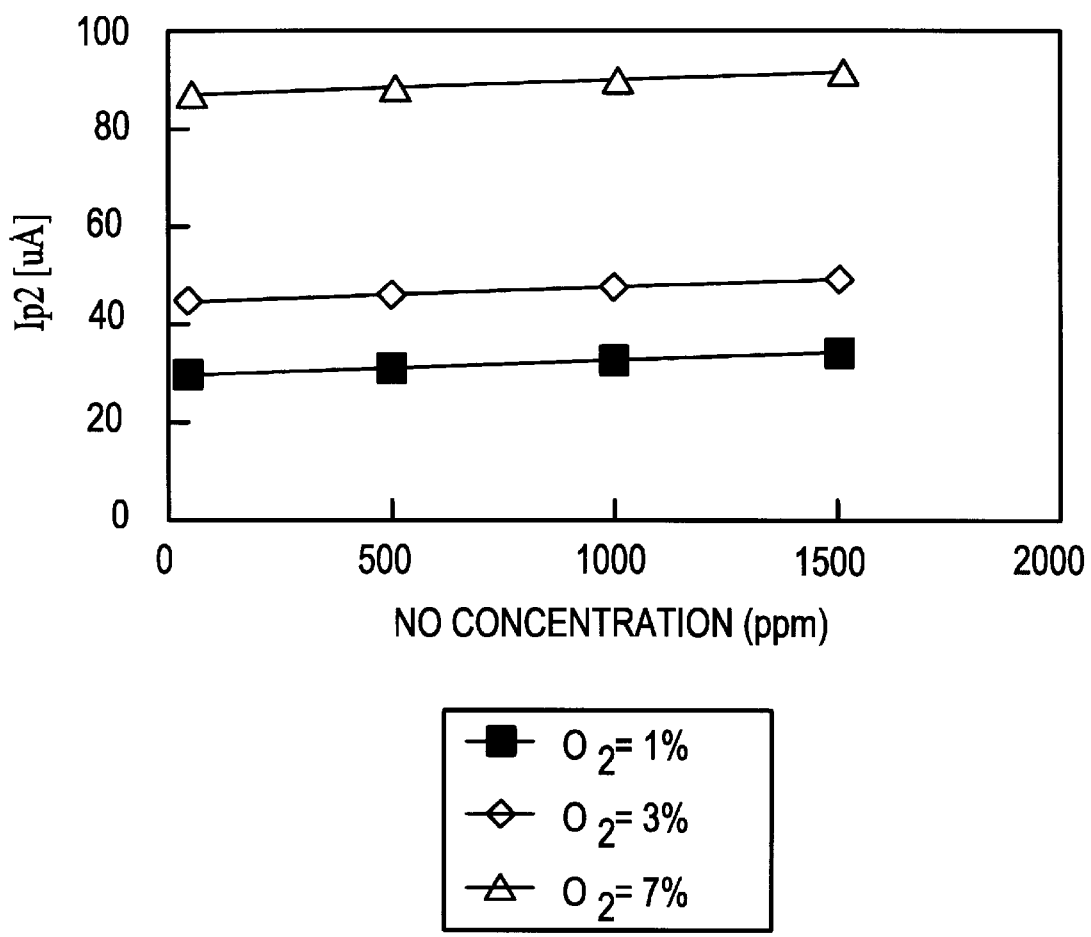
FIG. 12 is a graph showing the relation between the pump current $Ip_2$ and the oxygen concentration in the nitrogen oxide concentration sensor of the modified embodiment of the present invention (the configuration shown in FIG. 2).
Figure 13:
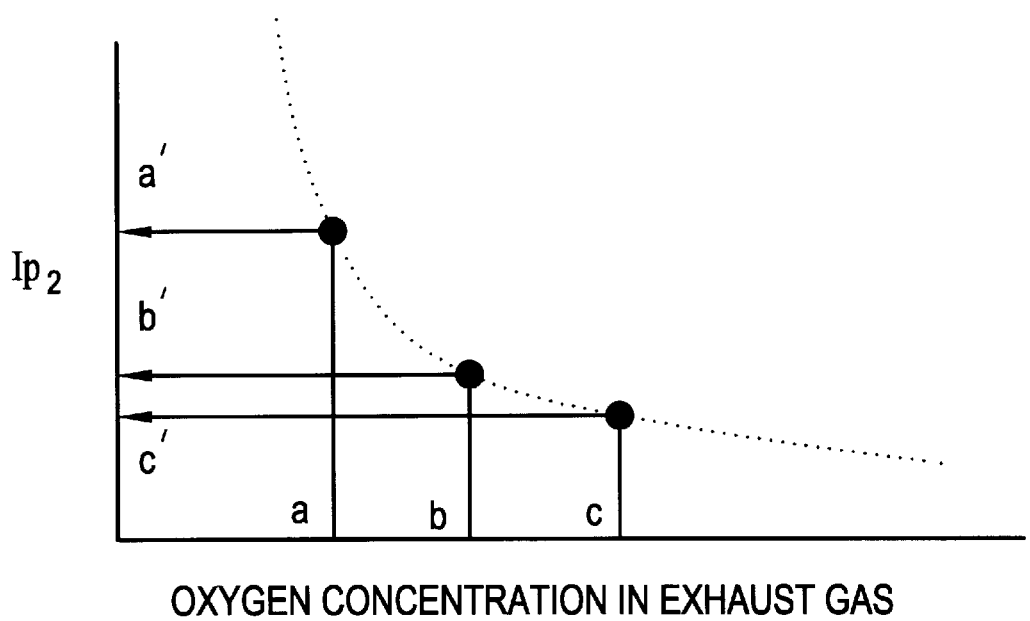
FIG. 13 is a graph showing an illustrative correlation between the oxygen concentration and $Ip_2$ for a nitrogen oxide concentration sensor according to a modification of the present invention different in design parameters from the embodiment of FIG. 11.

Next, the correlation between the pump current $Ip_2$, flowing on impressing 450 mV across the second oxygen pumping cell, and the pump current $Ip_2$, with the oxygen concentration in the measuring gas being 1%, 3% and 7%, was found. The results are shown in FIG. 11. From the graph of FIG. 11, the current value $Ip_2O$ of the second oxygen pumping cell can be determined. On the other hand, since there is a pre-set functional relation (herein a linear relation) of FIG. 12 between the nitrogen oxide concentration and the pump current $Ip_2$, an oxygen concentration in the measuring gas can be determined from pump current $Ip_1$ of the first oxygen pumping cell by previously finding data shown in FIGS. 10 and 11, and current $Ip_2O$ corresponding to the determined oxygen concentration at that time can be found from FIG. 11. If $IP_2O$ is determined, a substantially linear functional curve showing the relation between the pump current $Ip_2$ and the nitrogen oxide concentration can be plotted on the graph of FIG. 12, so that a high-precision nitrogen oxide concentration, as corrected on the basis of the pump current $Ip_2O$, can be found. There are occasions wherein, depending on the design parameters of the nitrogen oxide concentration sensor, the relation between the pump current $Ip_2$ and the oxygen concentration shown in FIG. 11 may be such as shown in FIG. 13. In this case, the nitrogen oxide concentration can be corrected in a similar manner using the oxygen concentration as found from the pump current $Ip_1$.

Test Example A2

Figure 14:
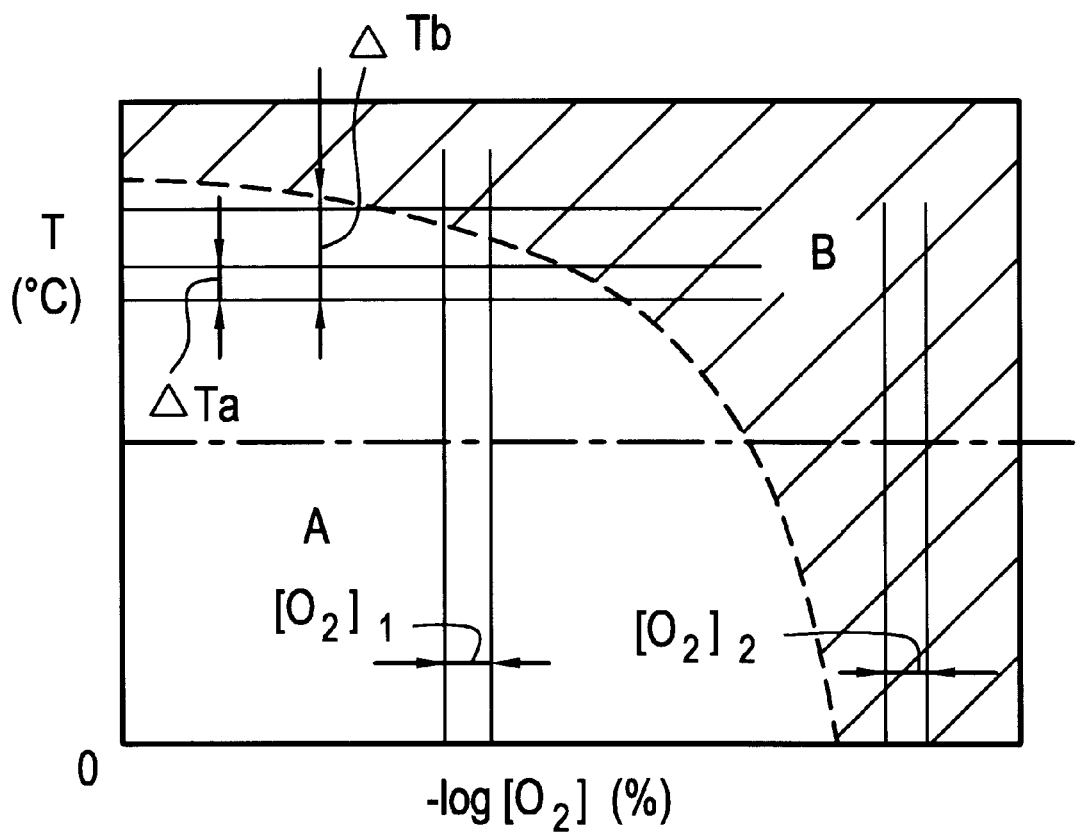
FIG. 14 is a graph for illustrating the state of use of a nitrogen oxide concentration sensor embodying the present invention.

FIG. 14 is a graph for illustrating the state of use of an Example of a nitrogen oxide concentration sensor. In this figure, the ordinate and the abscissa represent the temperature (° C.) in the first cavity and in the second cavity and the oxygen concentration (%) represented by $-\log[O_2]$, respectively. An area A and an area B in the figure denote an area where the nitrogen oxide is stable and an area where the nitrogen oxide is decomposed, respectively. In FIG. 14, a chain-dotted horizontal line denotes a lower limit temperature at which the oxygen pumping cell can be operated, while $\Delta Ta$ and $\Delta Tb$ denote ranges of temperature difference in the first cavity of a sensor having a small temperature difference and in the first cavity of a sensor having a large temperature difference. respectively. On the other hand, $[O_2]_1$ and $[O_2]_2$ denote a control range for the oxygen concentration in the first cavity and that in the second cavity, respectively.

In an oxygen concentration battery, an electromotive force (EMF) e generated between electrodes of the oxygen concentration measuring cell is given by $e=-(RT/nF)\ln(P_1/P_2)$, where F is a Faraday constant, R is a gas constant per mol, T is an absolute temperature and $P_1$, $P_2$ are oxygen partial pressures at both electrodes. In the oxygen concentration measuring cell, the oxygen concentration in the first cavity is measured using the oxygen partial pressure in air as a reference.

In nitrogen oxide concentration sensor of the Example $A_2$ of FIG. 2 or Example $A_3$ of FIGS. 6 and 7, there is no current leakage between the electrode of the oxygen concentration measuring cell and the electrode of the second oxygen pumping cell, so that it becomes possible to control the oxygen concentration in the first cavity to a high accuracy and hence to control the oxygen concentration in the first cavity to a constant value within a narrow range. If the oxygen concentration in the first cavity is fluctuated, such fluctuations directly affect the detected value of the nitrogen oxide concentration. The fluctuations in the oxygen concentration in the first cavity directly represent a measurement error. For example, if the oxygen concentration in the first cavity is fluctuated by 1 ppm, such fluctuation is significant in case of measuring the nitrogen oxide concentration of the order of a few ppm. With the nitrogen oxide concentration sensor of Example A2, it is possible to control fluctuations in the oxygen concentration in the first cavity so as to be approximately within ±0.01 ppm. If the second cavity 4 is charged with a porous material, the effective volume of the second cavity is small so that the pump current $Ip_1$ of the second oxygen pumping cell reaches an equilibrium value in a shorter time resulting in high responsiveness in measuring the nitrogen oxide concentration.

When controlling the oxygen concentration in the first cavity to a preset $[O_2]_1$ while monitoring the oxygen concentration in the first cavity by an oxygen concentration measuring cell with the oxygen partial pressure in air as a reference, even if the temperature fluctuations of $\Delta Ta$ would exist in the first cavity, there is no risk of decomposition of nitrogen oxides in the first cavity. However, if the temperature fluctuations of $\Delta Ta$ would exist in the first cavity, the state of part of the first cavity is moved into an area B in FIG. 14 to decompose part of the nitrogen oxides. Therefore, if the measuring gas in the first cavity is sent via the second diffusion path to the second cavity to lower the oxygen concentration to $[O_2]_2$ for realizing complete decomposition of the nitrogen oxides, part of nitrogen oxides is already decomposed and hence the concentration of nitrogen oxides cannot be measured accurately.

Test Example A3

The nitrogen oxide concentration sensor of Example A3 shown in FIGS. 6 and 7 were introduced via a hole formed in an exhaust gas pipe of an internal combustion engine flown through by a measuring gas for measuring the concentration of the nitrogen oxides. With the present sensor, it has been found that, if the sensor is viewed to be projected in a direction perpendicular to the solid electrolyte layer, the first cavity, second cavity and the heat generating part are substantially in register with one another, so that, if a measuring part of the sensor is viewed to be inserted via a hole formed in the pipe wall for detecting the nitrogen oxide concentration of the measuring gas flowing in the pipe, the first cavity, second cavity and the oxygen concentration measuring cell are substantially at the same distance from the pipe wall, such that there is produced substantially no temperature difference ascribable to the temperature distribution in the pipe.

Figure 15:
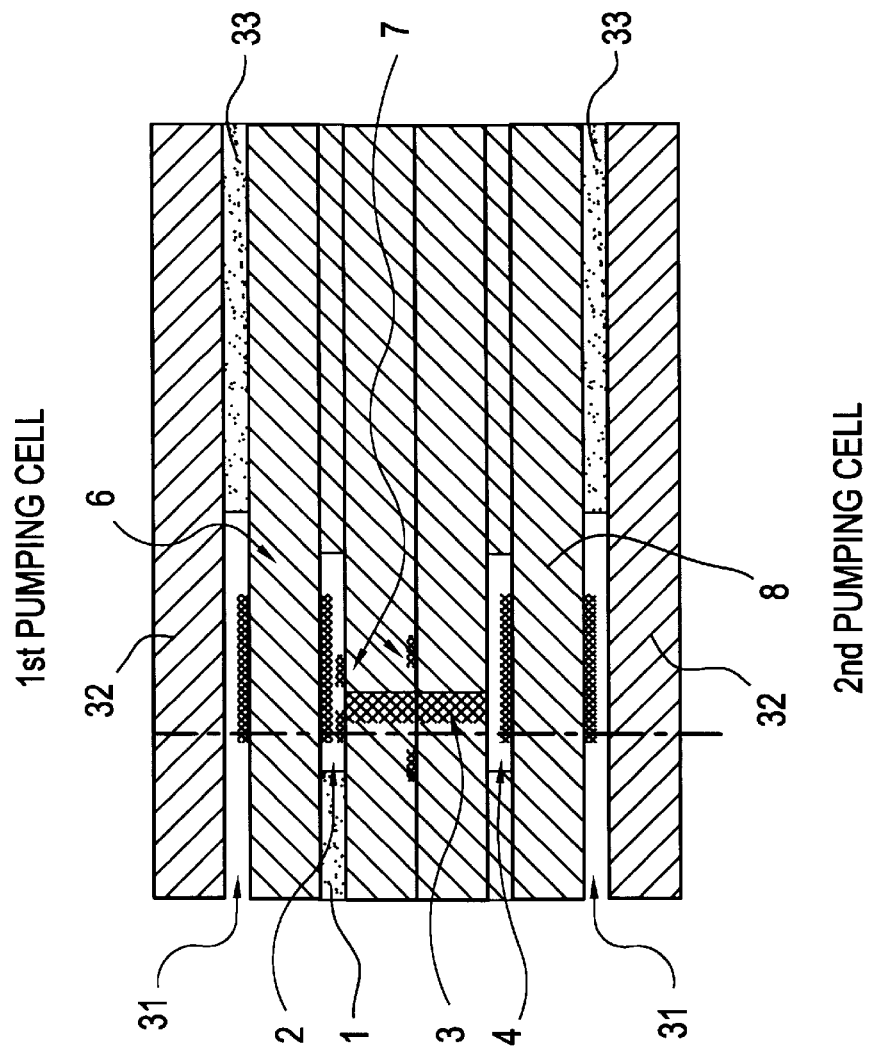
FIG. 15 is a cross-sectional view showing a further modification of a nitrogen oxide concentration sensor embodying the present invention.

On the other hand, since the first cavity is not elongated in shape, the temperature difference in the first cavity is small, thus enabling high-precision control of the oxygen concentration in the first cavity. Since the measuring gas at a pre-set low oxygen concentration is sent from the second diffusion path to the first cavity for measuring the nitrogen oxide concentration in the measuring gas, the nitrogen oxide concentration can be measured with high accuracy. Moreover, it has been found that, since the heat generating part of the heater is in register with the first cavity, second cavity and the oxygen concentration measuring cell on a projection drawing, the sensor part of the sensor can be heated easily, while the power consumption of the heater required for maintaining the temperature of the sensor part at a pre-set value can be lowered. It is also desirable to use two of the heaters configured as shown in FIG. 9 and to arrange the sensor part in-between these heaters to provide a sandwich structure. FIG. 15 shows such an example. Between the upper or lower heater 32 and the first or second pumping cell, respectively, is formed an exhaust conduit 31 communicating-with outside air for exhausting the oxygen gas extracted from the pumping cells. The base portion of the heater 32 is bonded to the base part of each pumping cell by an adhesive layer 33 such as a cement layer. An electrode of the oxygen concentration measuring cell 7 disposed on the side opposite to the first measuring chamber (cavity) serves as an internal reference electrode communicating with outside air. via a porous electrode and a porous lead.

It has also been found that, if a sensor is connected, as shown by Example A3 in FIG. 7, to a micro-computer having a recorder for measuring or controlling the oxygen concentration or temperature of the sensor part, and the micro-computer is caused to execute correction calculations based on data as found with the reference gas from the outputted first pump current $Ip_1$ or the second pump current $Ip_2$, a measured value of the corrected nitrogen oxide concentration can be obtained on a real-time basis so as to be directly used for realizing driving control of the internal combustion engine by connecting the micro-computer to the control system of the internal combustion engine.

Comparative Example A1

Using a conventional nitrogen oxide concentration sensor configured as shown in FIGS. 3 and 4, attempts were made for measuring the nitrogen oxide concentration. It has thus been found that the temperature setting range of the nitrogen oxide concentration sensor which allows normal operation of the sensor is relatively narrow. The reason was presumed to reside in that, due to the elongated shape of the first cavity of the nitrogen oxide concentration sensor, a temperature difference exists in the first cavity. It has also been found that, when measuring the nitrogen oxide concentration in the measuring gas of low nitrogen oxide concentration, the conventional nitrogen oxide concentration sensor is significantly lower in measurement accuracy than the nitrogen oxide concentration sensor of the present invention.

Example A5 and Comparative Example A2

Figure 18:
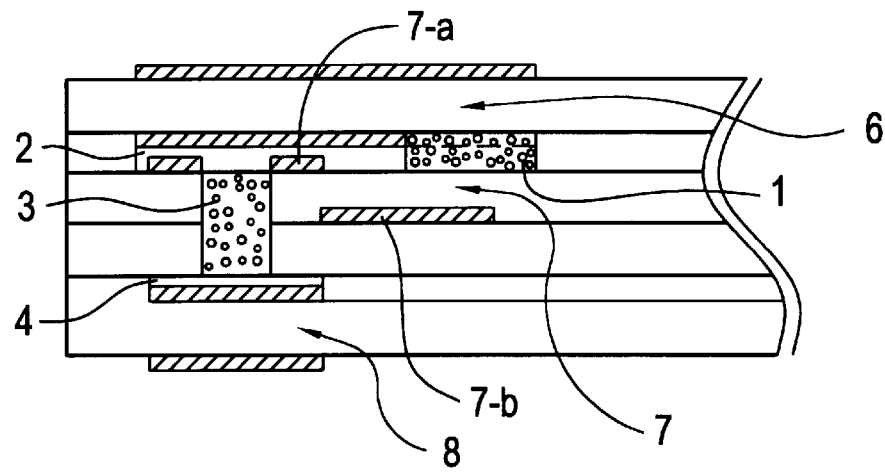
FIG. 18 is a cross-sectional view taken along the long side of a nitrogen oxide concentration sensor (Embodiment A5).

FIG. 18 is a cross-sectional view taken along the long side of the nitrogen oxide concentration sensor of the Example A5 of the present invention. The schematic structure of the crucial portion of the nitrogen oxide concentration sensor of the Example A5 of the present invention shown in FIG. 18 is as shown on the left side of FIG. 17 ($NO_x$ sensor embodying the present invention). That is, as explained previously, two first diffusion apertures (first aperture paths) are provided at a significant distance from the second diffusion aperture (second diffusion path) and the oxygen partial pressure measuring electrode 7 is smaller in size than the entire area of the bottom surface of the first measuring chamber 2 (shorter than the entire length of the first measuring chamber 2), and is arranged at a spacing from the first diffusion aperture 1 in the vicinity of the second diffusion aperture 3. On the other hand, the sensor of the type 4 of the Comparative Example has four first diffusion apertures 1 in the vicinity of the second diffusion aperture 3 for allowing the measuring gas to flow into the first measuring chamber, and an oxygen partial pressure measuring electrode 7-a is provided neighboring the first diffusion aperture 1 in substantially the entire area of the bottom surface of the first measuring chamber 2. On the other hand, the structure of the nitrogen oxide concentration sensor of Example A5 differs from the sensor of the Example shown in, for example, FIG. 1, is that the first diffusion apertures 1 are disposed opposed each other facing the short side of the first measuring chamber 2, the second diffusion aperture 3 is disposed at a spacing from the first diffusion aperture 1 towards the sensor end portion (first measuring chamber 2) and heating means formed by a Pt patterned wire is arranged as a separate member to sandwich (or surround) the element, while the distance between the first diffusion aperture 1 and the oxygen partial pressure detection electrode 7 is maintained at a pre-set value.

The sensors of types 1 to 3, in which the distance A between the first diffusion aperture 1 shown in FIG. 17 and the oxygen partial pressure detection electrode 7-a was changed as shown in Table A1, were prepared. The sensor of the type 4, as a Control Example, is of the same shape as the sensors of the types 1 to 3 except the configuration of the first aperture 1 or of the oxygen partial pressure detection electrode 7-a, and the relative disposition. The sensor is of a height (as measured in the direction of extension of the second diffusion aperture) of 1.35 mm, a width in the transverse direction (the direction of extension of the first diffusion aperture) of 4.1 mm, a length in the longitudinal direction (the direction of extension of the first measuring chamber) of 45 mm, with a width of the first diffusion aperture in the vertical direction in FIG. 17 of 2.4 mm and with a diameter of the second diffusion aperture 3 of 1.1 mm. The oxygen partial pressure detection electrode 7-a of the types 1 to 4 (see FIG. 17) is of a size (vertical direction× left-to-right direction in FIG. 17) of 6.9×2.2 mm for type 1 and of 2.0×2.2 mm for types 2 to 4, with a thickness being 10 to 20 $\mu$m for all types.

TABLE A1

| Type | A (mm) |
|---|---|
| Type 1 | 3 |
| Type 2 | 1.5 |
| Type 3 | 0 |
| Type 4 | Conventional type |

Test Example A4

Figure 19:
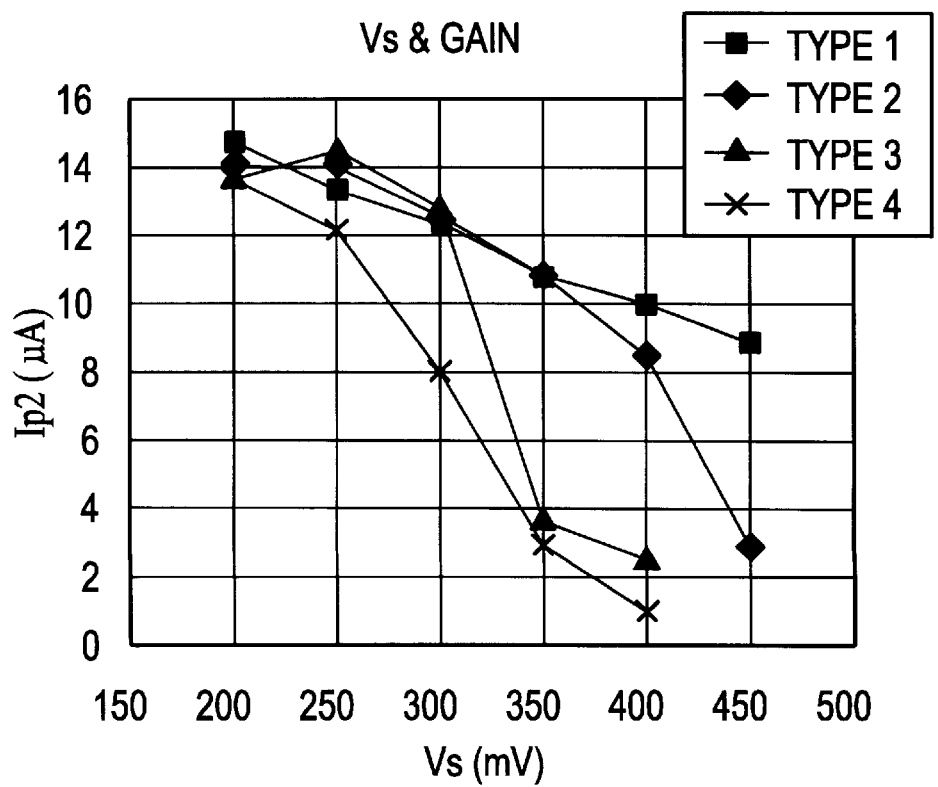
FIG. 19 is a graph showing the relation between the oxygen concentration detection potential Vs and the pump current $Ip_2$ of the second oxygen pumping cell for the nitrogen oxide concentration sensor of the modification (Embodiment A5) and the nitrogen oxide concentration sensor of a Comparative Embodiment.
Figure 20:
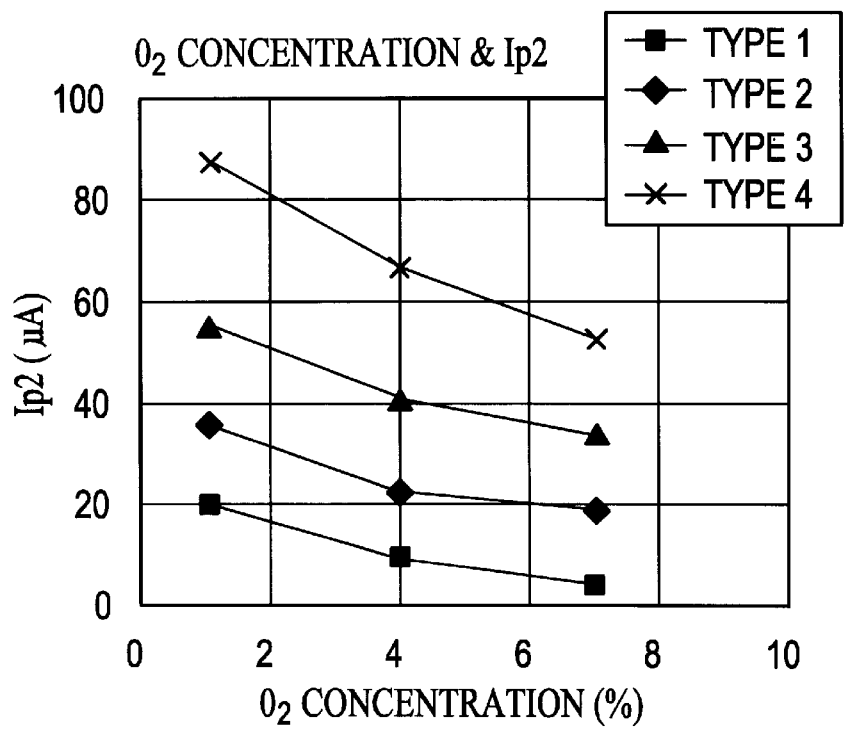
FIG. 20 is a graph showing the correlation between the oxygen concentration and $Ip_2$ by the nitrogen oxide concentration sensor according to the modification (embodiment A5) of the present invention and a Comparative Embodiment (Comparative Embodiment 2).
Figure 21:
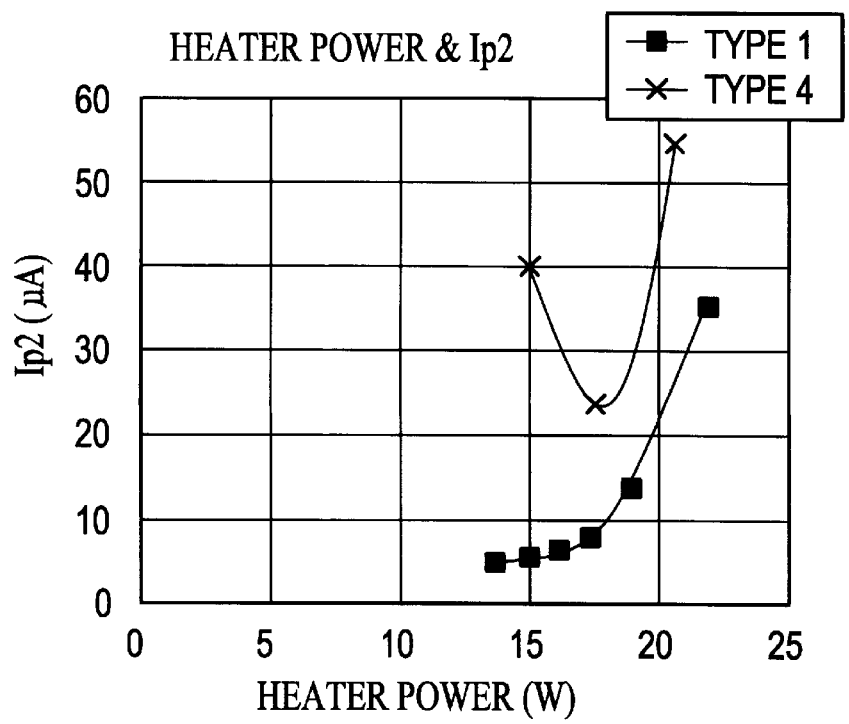
FIG. 21 is a graph showing the correlation between the heater power and $Ip_2$ by the modification (embodiment A5) of the present invention.

Using the sensors of types 1 to 4, the oxygen concentration detection potential Vs and the pump current $Ip_2$ of the second oxygen pumping cell were measured. The measurement conditions in case of measuring the correlation between the oxygen concentration detection potential Vs and the gain of the pump current $Ip_2$ of the second oxygen pumping cell were at an exhaust gas temperature of 300° C., sensor temperature of 800° C., an oxygen concentration in the exhaust gas of 7% and NO=1500 pm. For measuring the correlation between the oxygen concentration and $Ip_2$, the exhaust gas temperature was 300° C., sensor temperature was 800° C., oxygen concentration in the exhaust gases was 1, 4 and 7% and NO=0 ppm. For measuring the correlation between the heater power and $Ip_2$, the exhaust gas temperature was 300° C., oxygen concentration in the exhaust gases was 7% and NO=0 ppm. The sensor temperature is changed with the heater voltage (power), with a heater power of 16 W corresponding to 800° C. The gain of $Ip_2$ is 'an amount of change ($\mu$A) of $Ip_2$ in case of application of the pre-set concentration of NO: 1500 ppm'. The gain is preferred to be high for a better measuring sensitivity of NO gas concentration and not to be fluctuated by foreign factors. The offset of $Ip_2$ is "the value of $Ip_2$ ($\mu$A) in case of non-application of NO" and is equivalent to the concentration of residual oxygen left unpumped in the first measuring chamber. A small offset value is preferred, while it is preferred that the offset be more dull to various foreign factors, such as fluctuations in the oxygen concentration in the measuring gas atmosphere or temperature. Table A2 and FIG. 19 show the correlation between the oxygen concentration detection potential Vs for the sensor types 1 to 4 and the gain of the pump current (nitrogen oxide concentration detection current) $Ip_2$ of the second oxygen pumping cell. Table A3 and FIG. 20 show the correlation between the oxygen concentration for sensor types 1 to 4 and $Ip_2$, while Table A4 and FIG. 21 shows the correlation between the heater power and $Ip_2$.

TABLE A2

Relation between Vs set and Ip2

| | Ip2 ($\mu$A) | | | |
|---|---|---|---|---|
| Vs (mV) | Type 1 | Type 2 | Type 3 | Type 4 |
| 200 | 14.75 | 14.2 | 13.7 | 13.68 |
| 250 | 13.38 | 14 | 14.57 | 12.19 |
| 300 | 12.41 | 12.65 | 12.92 | 8.13 |
| 350 | 10.89 | 11 | 3.76 | 3.1 |
| 400 | 9.89 | 8.75 | 2.81 | 1.2 |
| 450 | 9.08 | 3.25 | | |

It is seen from Table A2 and FIG. 19 that the further away from the first diffusion aperture 1 the oxygen partial pressure detection electrode 7-a and the smaller the area of the oxygen partial pressure detection electrode 7-a formed around the second diffusion aperture 3, the lesser is the gain change of the pump current $Ip_2$ of the second oxygen pumping cell relative to changes in the oxygen concentration detection potential Vs, the larger is the gain of the pump current and the higher is the NO gas concentration measuring sensitivity.

TABLE A3

| Oxygen Concentration(%) | Ip2 ($\mu$A) | | | |
|---|---|---|---|---|
| | Type 1 | Type 2 | Type 3 | Type 4 |
| 1 | 19.35 | 35 | 55 | 87.28 |
| 4 | 9.95 | 23 | 41 | 66.89 |
| 7 | 6.1 | 19 | 35 | 54.22 |
| 20 | 4.12 | 14 | 29 | 61.56 |

It is seen from Table A3 and FIG. 20 that the further away from the first diffusion aperture 1 the oxygen partial pressure detection electrode 7-a and the smaller the area of the oxygen partial pressure detection electrode 7-a formed around the second diffusion aperture 3, the lesser is the value of and fluctuations in the nitrogen oxide concentration detection current $Ip_2$ relative to changes in the oxygen concentration and the lesser the influence of foreign disturbances on the oxygen concentration.

TABLE A4

Relation between Heater Power and Ip2

| Heater Power (W) | Ip2 ($\mu$A) | |
|---|---|---|
| | Type 1 | Type 4 |
| 20.475 | | 54.22 |
| 17.575 | | 23.94 |
| 14.79 | | 40.92 |
| 21.52 | 36.36 | |
| 18.76 | 14.05 | |
| 17.23 | 8.2 | |
| 16.02 | 6.15 | |
| 14.87 | 5.2 | |
| 13.62 | 5.3 | |

It is seen from Table A4 and FIG. 21 that the further away from the first diffusion aperture 1 the oxygen partial pressure detection electrode 7-a and the smaller the area of the oxygen partial pressure detection electrode 7-a formed around the second diffusion aperture 3, as in the type 1 sensor, the lesser is the value of and fluctuations in the value of the nitrogen oxide concentration detection current $Ip_2$ relative to the element temperature and the lesser is the influence of disturbances on the sensor.

From the above results, it has been shown that the gain fluctuations in the $Ip_2$ gain, the offset value, its fluctuations, the influence of element temperature fluctuations become lesser in the order of the types of 1 to 4 (with the type 1 being the best) to permit accurate measurement of nitrogen oxide concentration. Moreover, a sensor with a distance between the first diffusion aperture and the oxygen partial pressure detection electrode A=1.5 mm or longer is preferred, with a sensor with A=3 mm or longer being more preferred. A sensor having any optional value A of not less than 1.5 mm is also preferred.

It is thought to be desirable to provide the first diffusion aperture and the oxygen partial pressure detection electrode at a spacing from each other by not less than ⅔ (preferably by the same length) or longer of the length along the long side of the first measuring chamber of the oxygen partial pressure detection electrode in the longitudinal direction of the first measuring chamber (in the direction proceeding from the first diffusion aperture towards the second diffusion aperture, that is in the vertical direction in FIG. 17).

Manufacturing Example A

The method for manufacturing a nitrogen oxide concentration sensor shown in, for example, FIG. 18, and its layout, will now be explained. FIG. 22(A),(B) illustrates the method for manufacturing a nitrogen oxide concentration sensor and its layout. From FIG. 18 and from the following explanation, the layout and the manufacturing method of other Examples and Comparative or Control Examples will be understood easily.

Referring to FIG. 22(A),(B), a $ZrO_2$ sheet and a paste for electrodes are layered from left upper side towards left lower side and from right upper side towards right lower side to form a unitary sensor. The paste materials, such as an insulating coating or electrodes, are layered by screen printing on a pre-set $ZrO_2$ sheet. A manufacturing example A of various component parts, such as $ZrO_2$, shown in FIG. 22, is now explained.

Forming of $ZrO_2$ Sheet $ZrO_2$ powders were calcined at 600° C. for two hours in an atmospheric oven. 30 kg of the $ZrO_2$ thus fired was mixed in a trommel with 150 g of a dispersant, 10 kg of an organic solvent and 60 kg of balls. The resulting mixture was mixed and dispersed for approximately 50 hours and admixed with 4 kg of an organic binder dissolved in 10 kg of an organic solvent. The resulting mixture was further mixed for 20 hours to produce a slurry having a viscosity of the order of 10 Pa.s (Pascal/second). From this slurry, a $ZrO_2$ green sheet with a thickness of the order of 0.4 mm was prepared by the doctor blade method and dried at 100° C. for one hour.

Paste for Printing (1) A printing paste for a first oxygen pumping electrode a, an oxygen partial pressure detection electrode (oxygen reference electrode) a and the second oxygen pumping electrodes a and b were prepared by mixing 20 g of platinum powders, 2.8 g of $ZrO_2$ powders and a suitable amount of organic solvents in a mortar machine or a pot-mill and further mixed and dispersed for four hours. To the resulting mixture were added 2 g of an organic binder dissolved in 20 g of an organic solvent and 5 g of a viscosity adjustment agent. The resulting mixture was further mixed for four hours to produce a paste having a viscosity on the order of 150 Pa.s.

(2) A printing paste for the first oxygen pump electrode b and for the oxygen partial pressure detection electrode (oxygen reference electrode) b, was prepared by mixing 19.8 g of platinum powders, 2.8 kg of $ZrO_2$ powders, 0.2 g of gold powders, and a suitable amount of an organic solvent, for four hours and dispersed by a mortar machine or pot mill. To the resulting mixture were added 2 g of an organic binder dissolved in 20 g of an organic solvent and 5 g of a viscosity adjustment agent. The resulting product was further mixed for four hours to produce a paste having a viscosity of 150 Pa.s.

(3) A printing paste for an insulating coating and protective coating was prepared by mixing 50 g of alumina powders and a suitable amount of an organic solvent in a mortar machine or a pot mill, for 12 hours, by adding 20 g of a viscosity adjustment agent and by mixing the resulting mass for three hours. In this manner, a paste with a viscosity of the order of 100 Pa.s was formed.

(4) A printing paste for a porous material containing Pt (for lead wires) was prepared by mixing 10 g of alumina powders, 1.5 g of platinum powders, 2.5 g of an organic binder and 20 g of an organic solvent in a mortar machine or pot-mill for four hours by admixing 10 g of a viscosity adjustment agent and mixing the resulting mass for four hours. In this manner, a paste having a viscosity of the order of 100 Pa.s was produced.

(5) A printing paste for the first diffusion aperture was prepared by weighing 10 g of alumina powders with an average particle size of 2 $\mu$m, 2 g of an organic binder and 20 g of an organic solvent in a mortar machine or pot-mill, mixing and dispersing the resulting mass and admixing 10 g of a viscosity adjustment agent. The resulting mass was further mixed for four hours to produce a paste having a viscosity of the order of 400 Pa.s.

(6) A printing paste for carbon coating was produced by weighing 4 g of carbon powders, 2 g of an organic binder and 40 g of an organic solvent mixing and dispersing the resulting mass in a mortar machine or a pot-mill, and admixing 5 g of a viscosity adjustment agent for 4 hours. By printing a carbon coating, it becomes possible to prevent a first oxygen pump electrode b from being contacted with the oxygen reference electrode b, as an example. The carbon coating is used for forming a first measuring chamber and a second measuring chamber. Since carbon is burned off during firing, there is no carbon coating layer on the fired product.

Pellets

For the diffusion aperture, 20 g of alumina powders with an average particle size of the order of 2 $\mu$m, 8 g of an organic binder and 20 g of an organic solvent were mixed in a mortar machine or pot-mill for one hour and granulated. The resulting mass was pressed by a metal mold press under a pressure of approximately 200 MPa (2 t/cm$^2$) to produce a cylindrically-shaped press-molded product of 1.3 mm in diameter and 0.8 mm in thickness in a green state. The press-molded product in the green state was inserted into pre-set portions of the second and third layers of the zirconia green sheets and pressed to form a unitary product which was then fired to form a second diffusion aperture in the sensor.

Method of Layering ZrO$_2$

After pressing affixture of the second and third layers, the portion (1.3 mm diameter) thereof corresponding to the second diffusion aperture is punched and a cylindrically-shaped molded product which provides the second diffusion aperture is embedded in the punched portion. The first to fourth layers of ZrO$_2$ sheets were pressed and affixed to one another under a pressing force of 0.5 MPa (5 kg/cm$^2$) for a pressing time of one minute.

Removal of Organic Binder and Firing

The pressed and affixed molded product was subjected to removal of organic binder at 400° C. for two hours and fired at 1500° C. for one hour.

As for the aspects of A1 to A3, the effects of the present invention may be summarized as follows:

If the nitrogen oxide concentration sensor according to aspect A1 of the present invention, since the oxygen concentration measuring cell and the oxygen pumping cell are provided in different solid electrolyte layers, and hence only little or no current flows between the electrodes of the oxygen concentration measuring cell an the electrodes of the oxygen pumping cell, due to insulation between the electrodes, the measung accuracy of oxygen concentration is high thus enabling the oxygen concentration in the first cavity to be controlled accurately. This assures stable and accurate measurement of the nitrogen oxide concentration on a practical level even if the nitrogen oxide concentration oxide in the measuring gas is low.

With the method for measuring the nitrogen oxide concentration in aspect A2 of the present invention, the influence on the measured value of the nitrogen oxide concentration of the concentration of oxygen contained in the measuring gas may be eliminated or removed by correction to enable a measured value of high accuracy to be obtained in a stable manner. By annexing a micro-computer to the nitrogen oxide concentration sensor, the measured value of the corrected nitrogen oxide concentration may be obtained on the real-time basis to enable connection to a control system for a combustor of, for example, an internal combustion engine.

With aspect A3 of the present invention, since the electrode of the oxygen concentration measuring cell is partially disposed in the vicinity of the second diffusion path on a layer surface of the solid electrolyte layer formed with the aperture of the second diffusion path in a wall surface which defines the first cavity, or at least the electrode of the oxygen concentration measuring cell towards the first cavity is disposed at a spacing from the first diffusion path in the vicinity of the second diffusion path, the concentration of residual oxygen in the first measuring chamber can be measured accurately, so that it becomes possible to lower the residual oxygen concentration in the first measuring chamber without decomposing nitrogen oxides, and hence the oxygen concentration dependency and temperature dependency in the measurement of the nitrogen oxide concentration can be reduced significantly. Moreover, by setting the distance between the internal electrode of the oxygen concentration measuring cell and the internal exit of the first diffusion path so as to be within a pre-set value, the above effect may be achieved more reliably.

Preferred embodiments for carrying out the present invention are defined in the sub-claims. To the basic effects in the aspects A1, A2 and A3 are added further desirable merits and effects pertaining to the respective embodiments. The details have been stated in the Preferred Embodiments and Examples and hence are not explained here specifically.

Aspect B1

Preferred Embodiments

According to aspect B, the present inventors have found the facts set forth below, in the case of a NO$_x$ gas concentration sensor having a first oxygen (ion) pumping cell for pumping out oxygen and a second oxygen pumping cell for measuring the NO$_x$ gas concentration from the current Ip$_2$ due to decomposition of NO$_x$ and resulting efflux of the dissociated oxygen ions, in which an electrode outside the second measuring chamber of the second oxygen (ion) pumping cell is exposed to the atmosphere of the measuring gas (exhaust gas): (a) that since the electrode outside the second measuring chamber of the second oxygen pumping cell is exposed to the measuring gas atmosphere (exhaust gas), the electro-motive force generated in the second oxygen pumping cell depends on changes in the oxygen concentration in the atmosphere of the measuring gas. The present inventors have also directed attention to the facts (b) that an effective voltage (Vp$_2$–electro-motive force (EMF)) impressed across the electrodes of the second oxygen pumping cell for decomposing $NO_x$ depends on the oxygen concentration in the measuring gas atmosphere and (c) that the relation $Ip_2=(Vp_2-EMF)/R$ holds, where $Ip_2$ is the current flowing across the electrodes of the second oxygen pumping cell ($NO_x$ gas concentration measuring current), $Vp_2$ is the voltage applied across the electrodes of the second oxygen pumping cell for decomposing $NO_x$ and R is the resistance across the electrodes of the second oxygen pumping cell, so that an offset value of $Ip_2$ depends on the oxygen concentration in the measuring gas atmosphere. The present inventors conducted perseverant researches which led to achievement of the present invention.

For accomplishing the above object, the present invention of the aspect B is characterized by protection means (member) at least partially surrounding said electrodes in the vicinity of the electrode outside of the second measuring chamber (cavity). The protection means alleviates or eliminate changes in the atmosphere, brought about with changes in the state of the measuring gas. Such changes in atmosphere include rapid changes in oxygen concentration, changes in temperature and/or changes in the flow of atmospheric gas etc. The protection means may be provided for completely encircling the electrode.

The feature of aspect B is applied with advantage to a $NO_2$ gas concentration sensor comprising a first measuring chamber in which a measuring gas is introduced via a first diffusion resistance (or path), an oxygen partial pressure measuring electrode for measuring the oxygen partial pressure in the measuring gas in the first measuring chamber, a first oxygen pumping cell pumping out a sufficient amount of the oxygen in the measuring gas out of the first measuring chamber, based on the potential of the oxygen partial pressure measuring electrode, to such an extent as substantially not to cause decomposition of $NO_x$ in the measuring gas, a second measuring chamber into which the gas is introduced out of said first measuring chamber via a second diffusion resistance and a second oxygen pumping cell having on the inside and outside of the second measuring chamber a pair of electrodes across which a voltage is impressed to decompose $NO_x$ in the second measuring chamber, with a current flowing therein by the dissociated oxygen in an amount corresponding to the $NO_x$ gas concentration.

In a $NO_x$ gas concentration sensor of the present invention, desirable in connection with aspect B, the protection means is a solid electrolyte layer laminated on the second oxygen pumping cell so as to surround the electrode outside of the second measuring cell provided in the second oxygen pumping cell. Preferably, the protection means includes the solid electrolyte layer and a diffusion layer layered so as to coat the electrode for preventing the electrode from being directly exposed to the measuring atmosphere, wherein the electrode is provided outside the second measuring chamber between the second oxygen pumping cell and the solid electrolyte layer. Also preferably, the electrode outside of the second measuring chamber provided on the second oxygen pumping cell, diffusion layer and the solid electrolyte layer are laminated in this order and, more preferably, the lateral surface of the electrode is sealed with ceramics, such as dense alumina ceramic. The electrode is preferably constructed so as not to be directly contacted with outside air (atmosphere of the measuring gas or ambient air).

Figure 23:
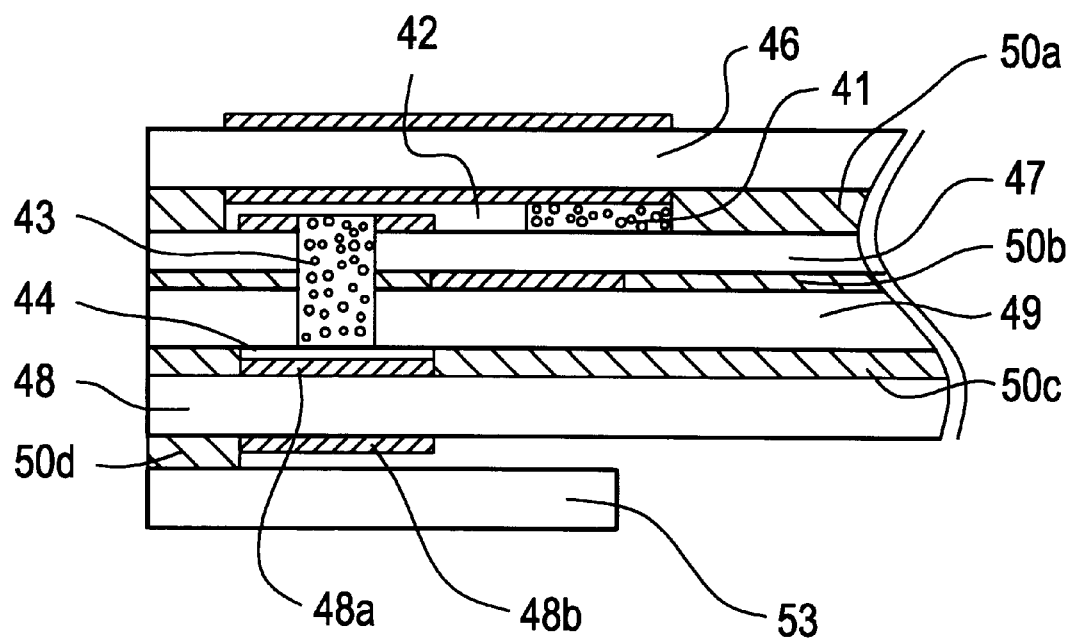
FIG. 23 illustrates the schematic structure of a $NO_x$ gas sensor embodying the present invention.

Referring to FIG. 23, essential portions of an embodiment of the present aspect, in particular the protection means which protect the electrode on the outer side of the second measuring chamber of the second oxygen pumping cell (exposed to the exhaust gas side), will be explained. In the $NO_x$ gas concentration sensor, shown in FIG. 23, as means for protecting an exhaust gas side electrode 48b of the second oxygen pumping cell 48 (electrode mounted on the outer side of the second measuring chamber) from rapid fluctuations in the atmosphere, a cover 53 formed of, e.g., a solid electrolyte is layered so as to surround the exhaust gas side electrode 48b of the second oxygen pumping cell 48 as an outer layer of the second oxygen pumping cell 48. This cover 53 reduces fluctuations in the oxygen concentration in the vicinity of the electrode 48b to stabilize the electromotive force generated between the electrodes of the second oxygen pumping cell. The result is that the offset of the second oxygen pumping cell current $Ip_2$ is stabilized and the $Ip_2$ offset is reduced in particular on the low oxygen concentration side so that ultimately the oxygen concentration dependency of the $Ip_2$ offset and gain is lowered.

Such $NO_x$ concentration sensor is applied with advantage to, above all, a system having a diesel engine subject to severe fluctuations in the oxygen concentration in the exhaust gas, or to a system subject to fluctuations in the air/fuel ratio.

The cover 53 shown in FIG. 23 is effective to prevent the severe flow of the exhaust gas from flowing around the space between the cover and the electrode 48b to intensify the above operation.

Preferably, a porous diffusion layer of, for example, alumina or alumina-zirconia complex material, covering the electrode 48b outside of the second measuring chamber of the second oxygen pumping cell 48, is provided on the inner side of the cover, as shown in FIG. 24A. The interstice on the inner side of the cover (clearance between the cover and the electrode 48b) or the thickness of the diffusion layer in the layering direction, is preferably in a range from 10 to 20 μm.

Although the cover 53 of FIG. 23 partially surrounds the electrode 48b, it may also be mounted for completely surrounding the electrode 48b.

The present aspect is preferably applied to a sensor in which the first oxygen pumping cell, oxygen concentration measuring cell and the second oxygen concentration measuring cell are provided in respective different solid electrolyte layers. Also, for preventing the current leakage between the electrodes provided in these cells, an insulating layer of, for example, alumina ceramic etc., is layered between these cells. Moreover, a heater layer is preferably provided for maintaining a constant temperature of the oxygen concentration measuring cell.

The solid electrolyte may be a zirconia-yttria solid solution or a zirconia-calcia solid solution etc. As a material for the porous electrode formed on both surfaces of the thin plate-shaped solid electrolyte layer by screen printing or firing, platinum or rhodium exhibiting the catalytic function or alloys thereof is preferably employed. As the first and second diffusion apertures, porous ceramics, for example, porous alumina ceramics, are preferably employed. Preferably, the heat generating part of the heater is formed of a complex material, such as ceramics-platinum or platinum alloys, while its lead portion is formed of platinum or platinum alloys.

The present invention is also applicable to a CO or HC gas concentration sensor. As in the case of the $NO_x$ gas concentration sensor, the effect of the atmosphere (oxygen concentration or moisture) is decreased to permit accurate measurement of the concentration of the measuring gas. Other preferred features are disclosed in aspects A1 to A3 corresponding to the JP Patent Application No. 8-160812, the contents of which can be incorporated in this aspect upon need.

Examples B

Referring to the drawings, embodiments of the present aspect will be explained.

Example B1

FIG. 23 is a cross-sectional view taken along the longitudinal direction of a $NO_x$ gas concentration sensor according to Example B1 of the present invention. The $NO_x$ gas concentration sensor, shown in FIG. 23 is made up of a solid electrolyte layer, a layer of a first oxygen pumping cell 46 having electrodes formed on both sides of the solid electrolyte layer, an insulating layer 50a including a first measuring chamber 42, another solid electrolyte layer, i.e., a layer of an oxygen concentration measuring cell 47 having an oxygen partial pressure measuring electrodes formed on both sides of the solid electrolyte layer, an insulating layer 50b, a layer 49 of a solid electrolyte, an insulating layer 50c including a second measuring chamber 4, a further solid electrolyte layer, i.e, a layer of a second oxygen pumping cell 48 having electrodes 48a, 48b formed on both sides of the solid electrolyte layer, laminated by layered in this order. In the first measuring chamber 42 are formed a first diffusion aperture 41 for introducing the measuring gas via diffusion resistance and a second diffusion aperture 43 spaced apart from each other. A second diffusion aperture 43 is passed through the oxygen concentration measuring cell 47, insulating layer 50b and the layer of the solid electrolyte 49 for establishing communication between the first measuring chamber 42 and the second measuring chamber 44 so that a gas containing at least $NO_x$ and $O_2$ is introduced from the first measuring chamber 42 via diffusion resistance into the second measuring chamber 44.

The $NO_x$ gas concentration sensor of the Example B1 has a feature that the electrode 48b is covered by the protective layer 53 formed of a solid electrolyte (zirconia ceramic). The protective layer 53 is laminated on the surface of an insulating layer 50d thicker than the electrode 48b so as to be extended in the long-axis direction of the sensor slightly spaced apart from the electrode 48b.

The function of the protective layer is previously explained in the preferred embodiment of the present aspect and hence is not specifically explained.

Although not shown, heater layers for heating the sensor are bonded via a cement or adhesion layer to the first oxygen pumping cell 46 and to an outer side of the protective layer 53 of solid electrolyte for sandwiching the entire sensor in the laminating direction.

One of the features of the present sensor is that the first measuring chamber 42 and the second measuring chamber 44 are substantially in register with each other in the vertical direction. Another feature is that the first diffusion apertures 41 are formed on both sides of the sensor, instead of on the distal end thereof, there is charged no porous material in the second measuring chamber 44, insulating films are formed between all neighboring solid electrolyte layers, and the cell electrodes are insulated from each other. The second measuring chamber 44 may be charged with a porous material.

Meanwhile, a reference oxygen concentration upon measuring by a pair of electrodes of the oxygen concentration measuring cell 47 may be in communication with outside air via a pre-set diffusion resistance and via the outer electrode of the first measuring chamber 42 and its lead wire (pattern) formed both of a porous material. If a pre-set minute current is allowed to flow in the oxygen concentration measuring cell 47, one of the electrodes thereof may be used as a self-generating reference electrode. The self-generating reference electrode has a merit that the reference oxygen concentration is scarcely affected by changes in the oxygen concentration in air.

Example B2

Figure 24:
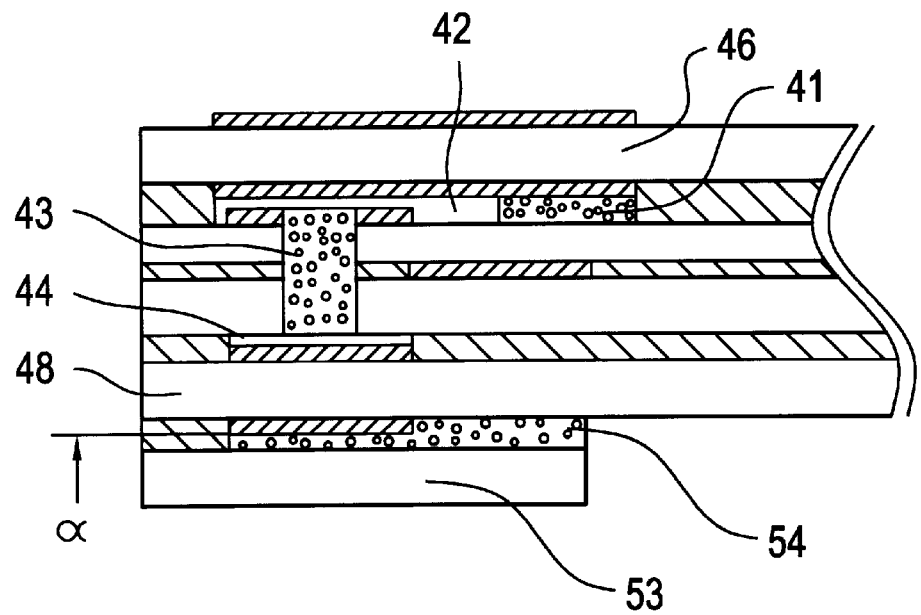
FIGS. 24A and 24B illustrate the schematic structure of a $NO_x$ gas sensor according to a further embodiment of the present invention, where
Figure 24:
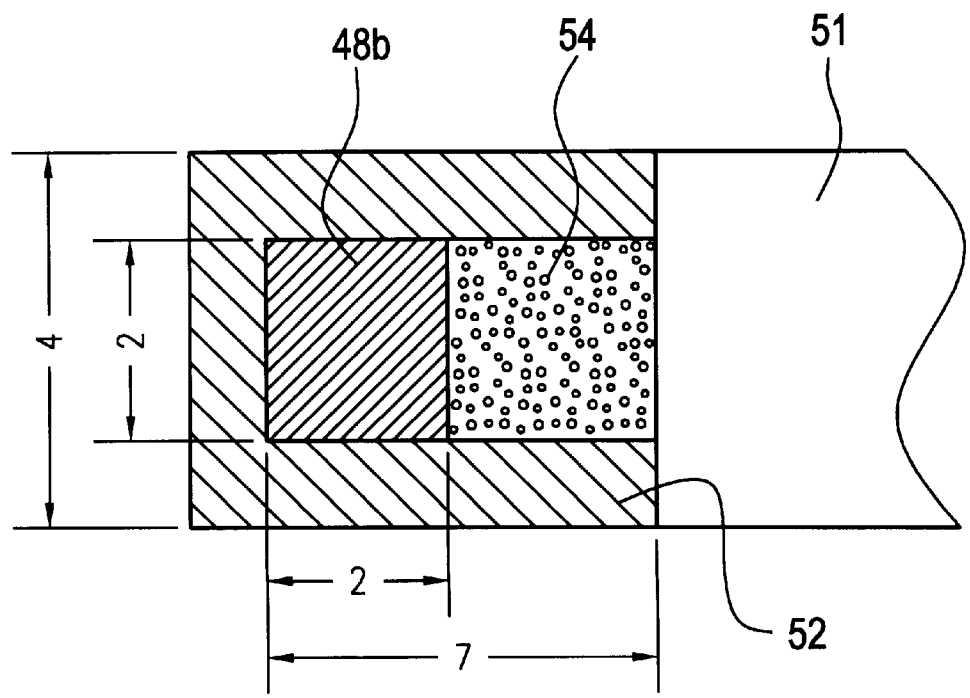

FIG. 24 illustrates the structure of a $NO_x$ gas concentration sensor according to another embodiment of the present invention, wherein FIG. 24A is a cross-sectional view of the $NO_x$ gas concentration sensor according to this embodiment, taken along its longitudinal direction, and FIG. 24B is a cross-sectional view taken along the direction of arrow α in FIG. 24A. Since the $NO_x$ gas concentration sensor according to this example B2 is configured similarly to the $NO_x$ gas concentration sensor according to example B1 shown in FIG. 23, the parts or components similar to those of the sensor of example B1 are not specifically explained.

The $NO_x$ gas concentration sensor shown in FIG. 24 includes, in addition to the structure of example B1, a porous diffusion layer of alumina 54 covering the electrode 48b in an interstice between the second oxygen pumping cell 48 and the protective layer 53 formed of, e.g., a solid electrolyte. The protective layer 53 of the solid electrolyte and the porous diffusion layer 54 formed of alumina alleviate changes in atmosphere around the electrode 48b for diffusing a pre-set gas.

The layout of the $NO_x$ gas concentration sensor of Example B2 used in the test examples as later explained and an illustrative method of forming a $ZrO_2$ sheet is explained. Meanwhile, the layout of the sensor of Example B1 and the sensor of a reference example will be readily understood from FIG. 25.

FIG. 22(A),(B) provides the steps (1)–(26) of a first stage followed by steps (27b)–(30b) of stage (B).

Referring to FIGS. 22 and 25, $ZrO_2$ sheets and paste for electrodes are layered from upper left to lower left, upper right and to lower right for producing a unitary sensor. The paste materials, such as insulating coats or electrodes, are layered by screen printing on a pre-set $ZrO_2$ sheet.

Manufacturing Example B

In the following, a manufacturing example of various component parts, such as $ZrO_2$ sheets shown partially in FIG. 25 will be explained.

The $NO_x$ gas concentration sensor of Examples B1 and B2 used in Test Examples B1 and B2 has an outer dimension of 50 mm in length in the longitudinal direction, 4 mm in width and 1.3 mm in the direction of thickness (in the laminating direction), with the exclusion of the protective layer 53, insulating layer 50d and the porous diffusion layer 54. The second oxygen pumping cell is 0.3 mm in thickness, 2 mm in length along the long side and 2 mm in width along the short side of the sensor, with the electrodes of the second oxygen pumping cell being 10 to 20 $\mu$m in thickness. The protective layer 53 of the electrode 48b and the porous diffusion layer 54 are 0.3 mm and 10 to 20 $\mu$m, respectively, in thickness. Other sizes are shown by arrows in mm in FIG. 24B.

Figure 28:
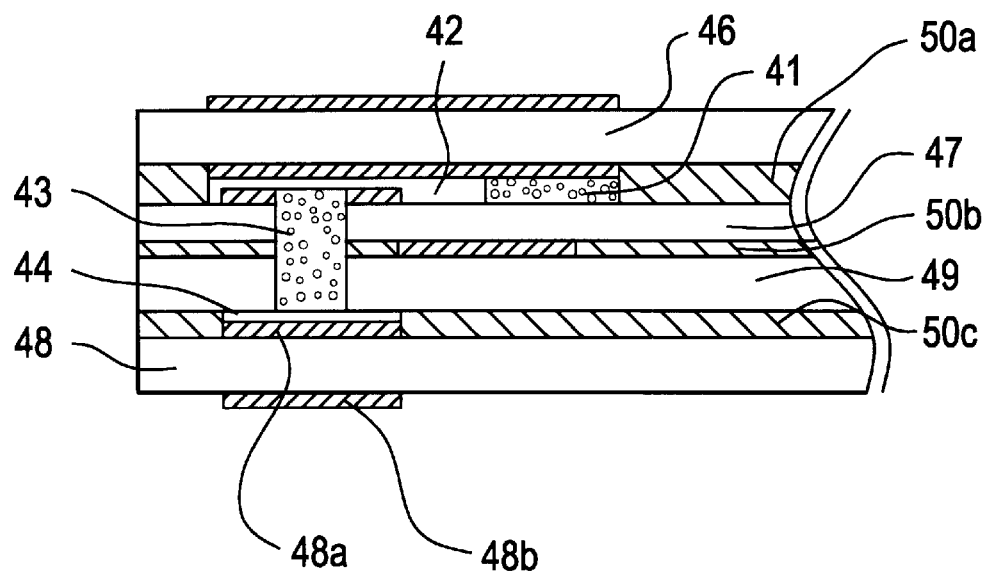
FIG. 28 illustrates the schematic structure of a $NO_x$ gas sensor of a Control Example.

Using the $NO_x$ gas concentration sensors of Examples B1 and B2, tests were conducted for measuring the NO gas concentration in the measuring gas. The control sensor of the reference example shown in FIG. 28 is the same as the Examples of FIGS. 23 and 24 except that the control sensor is devoid of the protective layer 53, insulating layer 50d and the porous diffusion layer 54. The common measuring conditions in the test Examples B1-B2 described below include measuring gas components: NO (0 to 1500 ppm), $O_2$ (0 to 16%), $CO_2$ (10%), with the balance being $N_2$, temperature of the exhaust gas (measuring gas) of 300° C. and the sensor temperature of 800° C.

Test Example B1

Measurements were made of fluctuations in the offset value of the second oxygen pumping current for various values of the oxygen concentration, with NO: 0%. Meanwhile, the offset means a value of $Ip_2$ in case NO is not charged into the measuring gas, and is equivalent to the residual oxygen concentration left unpumped in the first measuring chamber 2. A smaller value of the offset is preferred. It is desirable for the offset to be less sensitive to various extraneous conditions, such as oxygen concentration or temperature in the measuring gas atmosphere and hence less susceptible to fluctuations.

Figure 26:
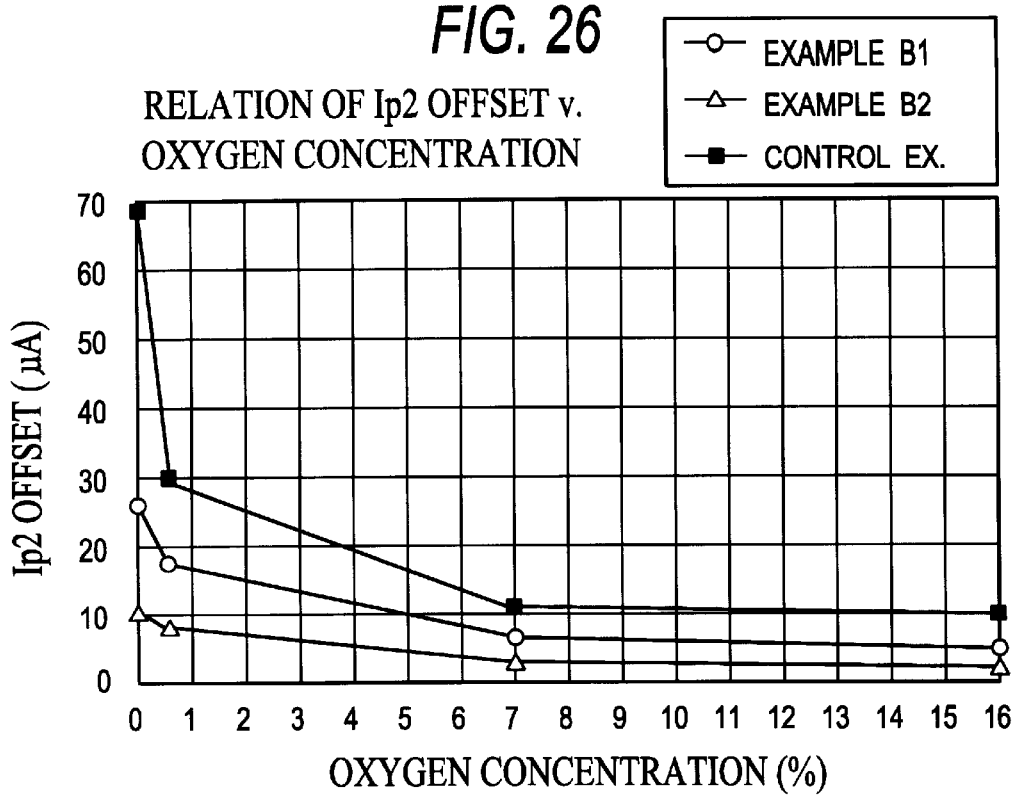
FIG. 26 is a graph showing the oxygen concentration dependency of the offset of the second oxygen pumping current $Ip_2$ wherein white circles, white triangles and black squares denote measured results by the $NO_x$ gas sensors of Embodiment 1, Embodiment 2 and the Control Embodiment, respectively.

Table B1 and FIG. 26 show the results of the Test Example B1. FIG. 26 is a graph showing the oxygen concentration dependency of the offset of the second oxygen pumping current $Ip_2$. In this graph, white circles, white triangles and black squares denote the measured results of the Examples B1 and B2 and Control example, respectively.

TABLE B1

Relation between Oxygen Cencentration and Ip2 Offset

| Oxygen Concentration(%) | Ip2 offset ($\mu$A) | | |
|---|---|---|---|
| | Example 1 | Example 2 | Example 3 |
| 16 | 5.18 | 3.18 | 9.87 |
| 7 | 7.83 | 4.87 | 11.1 |
| 0.5 | 17.25 | 8.32 | 28.77 |
| 0 | 25.57 | 10.44 | 68.03 |

As may be seen from FIG. 26, the amount of change in the $Ip_2$ offset relative to the change of 1 to 16% of the oxygen concentration is smaller in the sensors of Examples B1 and B2 than in the sensor of the Control example. In particular, in the sensor of Example B2, the amount of change in the $Ip_2$ offset for the amount of change of 1 to 16% of the oxygen concentration is not more than 10 $\mu$A, indicating that the amount of change in the offset is extremely small. Also the offset value is lower in the Examples B1 and B2 than in Control example.

Test Example B2

1500 ppm NO was injected into a measuring gas and the gain of the second oxygen pump current was measured for the oxygen concentration of 0 to 16%. Meanwhile, the gain is the amount of change of $Ip_2$ ($\Delta Ip_2$) on injection of NO at a pre-set concentration (herein 1500 ppm). A larger value of the offset is preferred. It is desirable for the gain to be less sensitive to various extraneous conditions, such as oxygen concentration or temperature in the measuring gas atmosphere and hence less susceptible to fluctuations.

Figure 27:
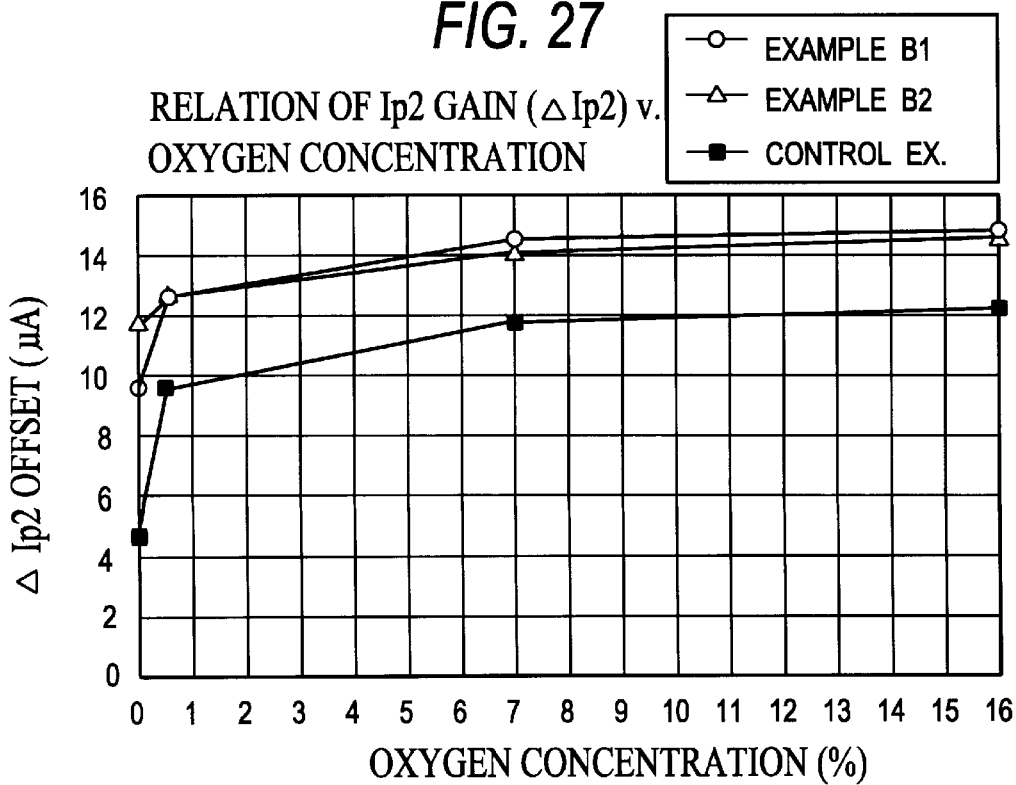
FIG. 27 is a graph showing oxygen concentration dependency of the gain of the second oxygen pumping current $Ip_2$, wherein white circles, white triangles and black squares denote measured results by the $NO_x$ gas sensors of Embodiment 1, Embodiment 2 and the Control Example, respectively.

Table B2 and FIG. 27 show the results of the Test Example B2. FIG. 27 is a graph representing oxygen concentration dependency in terms of gain $\Delta IP_2$ of the second oxygen pump current. In this graph, white circles, white triangles and black squares denote the measured results of the Examples B1 and B2 and Control example, respectively.

TABLE B2

Relation between Oxygen Concentration and Gain($\Delta$ Ip2)

| Oxygen Concentration(%) | $\Delta$ Ip2 ($\mu$A) | | |
|---|---|---|---|
| | Example 1 | Example 2 | Example 3 |
| 16 | 14.85 | 14.69 | 12.31 |
| 7 | 14.41 | 14.07 | 11.66 |
| 0.5 | 12.79 | 12.83 | 9.68 |
| 0 | 9.68 | 11.72 | 4.59 |

As may be seen from FIG. 27, the amount of change in the $Ip_2$ gain relative to the change of 0 to 16% of the oxygen concentration is smaller in the sensors of Examples B1 and B2 than in the sensor of the Control example. In particular, in the sensor of Example B2, the amount of change in the $Ip_2$ gain for the amount of change of 0 to 16% of the oxygen concentration is not more than 4 $\mu$A, indicating that the amount of change in the gain is extremely small. Also the gain value is lower and the measuring sensitivity higher in the Examples B1 and B2 than in Control example.

It is seen from the measured results of Test Examples B1 and B2 that, with the sensors of the Examples B1 and B2, the measuring gas oxygen concentration dependency of the offset and the gain of the second oxygen pump current $Ip_2$ is lowered in particular on the low oxygen concentration side, thus improving accuracy in $Ip_2$-based $NO_x$ gas concentration measurement. it is also seen that, since the oxygen concentration dependency of the $Ip_2$ offset and gain in the sensor of Example B2 is lowered, the oxygen concentration dependency is further lowered if the electrode outside the second measuring chamber of the second oxygen pumping cell is coated with the porous diffusion layer, thus improving $NO_x$ gas concentration measurement accuracy.

The effect of the present aspect may be summarized as follows:

In the present aspect, since the measuring gas oxygen dependency of the offset and gain of the second oxygen pump current $Ip_2$ is lowered, measurement of the $Ip_2$-based $NO_x$ gas concentration may be improved in accuracy. By forming the protective layer as a solid electrolyte layer layered on the second oxygen pumping cell for surrounding the electrode outside of the second measuring chamber provided on the second oxygen pumping cell, the protective layer can be formed simultaneously with the cell production process thus decreasing the number of steps and lowering the manufacturing cost. If a diffusion layer layered for covering the electrode is provided between the second oxygen pumping cell and the solid electrolyte layer for preventing the electrode from being directly exposed to the measuring atmosphere, changes in the atmosphere in the vicinity of the electrode can be alleviated to a greater extent.

Aspect C

Preferred Embodiments

The feature of aspect C is applied with advantage to a $NO_2$ gas concentration sensor including a first measuring chamber in which a measuring gas is introduced via a first diffusion resistance, an oxygen partial pressure measuring electrode for measuring the oxygen partial pressure in the measuring gas in the first measuring chamber, a first oxygen pumping cell pumping out a sufficient amount of oxygen in the measuring gas out of the first measuring chamber, based on the potential of the oxygen partial pressure measuring electrode, to such an extent as not to cause decomposition of oxygen in the measuring gas by $NO_2$, a second measuring chamber into which the gas is introduced out of the first measuring chamber via a second diffusion resistance and a second oxygen pumping cell across which the voltage is impressed for decomposing $NO_x$ in the second measuring chamber, with the current flowing therein by pumping out the dissociated oxygen in an amount corresponding to the $NO_x$ gas concentration.

In connection with aspect C, preferably the first diffusion resistance (or path) is disposed at a different side from the second diffusion resistance in the first measuring chamber (cavity) at a spacing from each other. An electrode assigned to the first measuring chamber and an inlet opening of the second diffusion resistance (or path) are disposed on one and the other of opposing wall surfaces of the first measuring chamber, respectively. At least the electrode exposed to the first measuring chamber of the first oxygen pumping cell is extended from the vicinity of the first diffusion resistance at longest to a range not reaching the immediately above area of the inlet opening of the second diffusion resistance. Also preferably, the electrode exposed to the first measuring chamber of the first oxygen pumping cell is at least not formed directly above (overlapping with) or in the vicinity of an inlet opening (first measuring chamber side) of the second diffusion resistance.

Referring to FIGS. 29 to 37, an embodiment of the present aspect will be explained. The measuring principle in a $NO_x$ gas concentration sensor having two sets of diffusion resistances, oxygen pumping cells and measuring chambers is as follows: (1) The exhaust gas flows into the first measuring chamber via a first diffusion aperture having a diffusion resistance. (2) By the first oxygen pumping cell, oxygen in the first measuring chamber is pumped out to such an extent that $NO_x$ in the first measuring chamber is not decomposed (the oxygen partial pressure in the first measuring chamber is controlled by an output signal of an oxygen partial pressure measuring electrode). (3) The gas in the first measuring chamber (concentration-controlled $O_2$ gas plus $NO_x$ gas) flows into the second measuring chamber via a second diffusion aperture having a diffusion resistance. (4) By the second oxygen pumping cell further pumping out oxygen from the gas in the second measuring chamber, the $NO_x$ gas in the second measuring chamber is decomposed into $N_2$ and $O_2$. (5) Since the current $Ip_2$ flowing through the second oxygen pumping cell has a linear relation with respect to the $NO_x$ gas concentration, the $NO_x$ gas concentration can be measured by detecting $Ip_2$.

Figure 29:
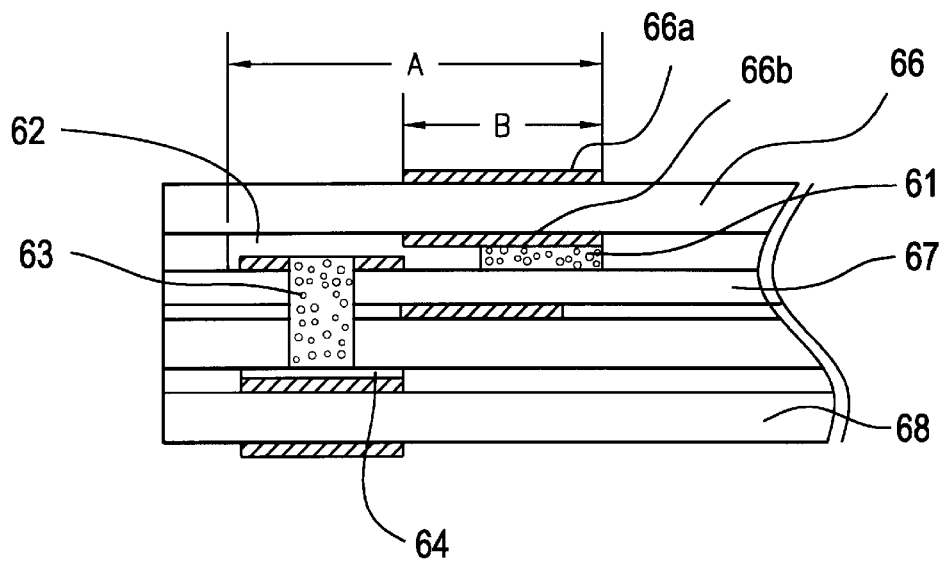
FIGS. 29A to C illustrate a $NO_x$ gas sensor embodying the present invention, where
Figure 29:
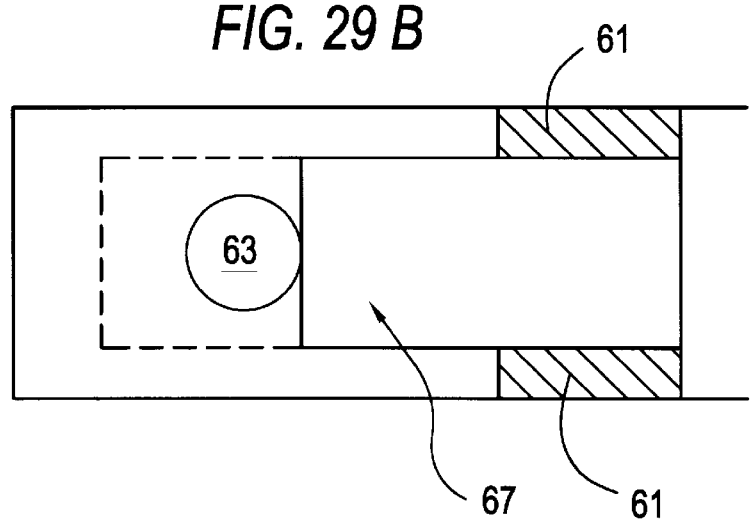
Figure 29:
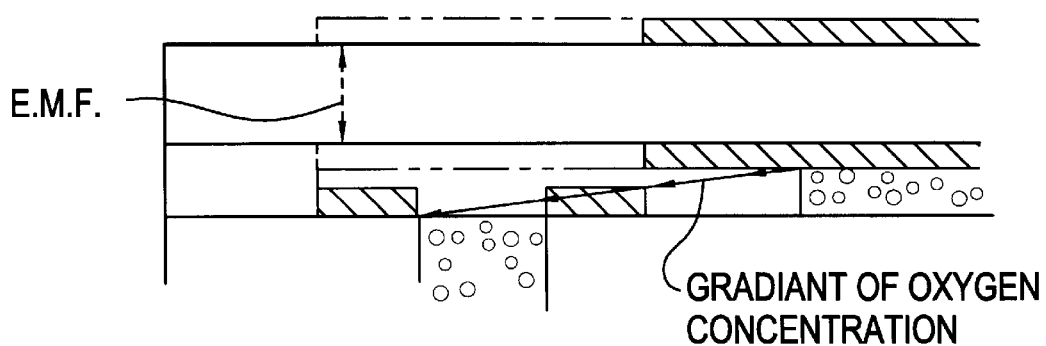
Figure 37:
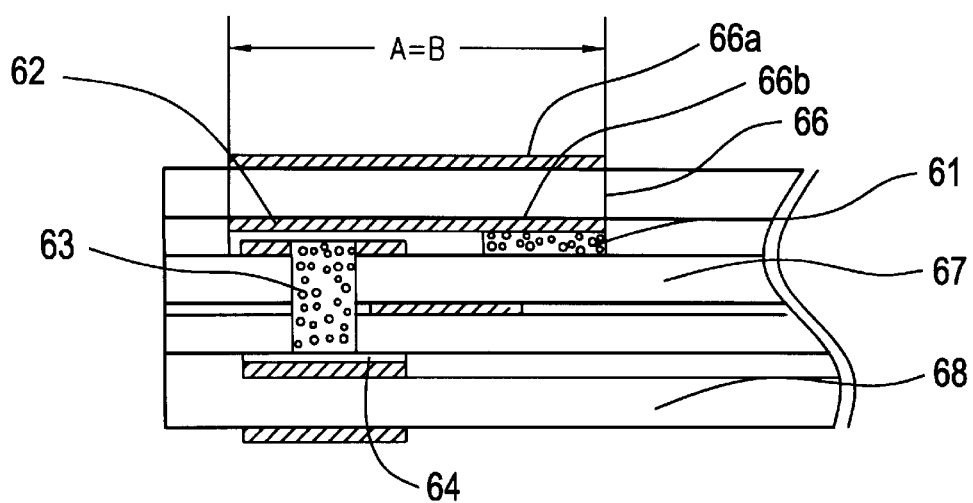
FIG. 37 is a cross-sectional view showing the schematic structure of a $NO_x$ gas concentration sensor according to a Control Example.

The feature of the $NO_x$ gas concentration sensor according to an embodiment of the present aspect is explained by referring to FIG. 29 illustrating a sensor according to an example of the present invention and to FIG. 37 illustrating a sensor according to a Control example concerning the present aspect. The present invention, however, is not limited to the sensor shown in FIG. 29. The sensor shown in FIG. 29 differs from the sensor shown in FIG. 37 in that, in the sensor of FIG. 29, the distal ends directed to the second diffusion aperture 63 of the electrodes 66a, 66b of the first oxygen pumping cell 66 have been removed (A>B). Therefore, the length of each of the electrodes 66a, 66b is shorter and hence the electrode area is smaller in the sensor of FIG. 29. By the electrodes of the first oxygen pumping cell 66 being shorter in length, the oxygen concentration gradient in the first measuring chamber 62 in particular in the measuring gas flow direction (direction proceeding from a first diffusion aperture 61 towards a second diffusion aperture 63) is lowered, that is the oxygen concentration difference from one to the opposite end of the electrode 66b is reduced, that is the oxygen concentration difference in the range where the electrode 66b is present is reduced, while the electromotive force generated at the distal portions of the electrodes 66a, 66b is suppressed, as shown in FIG. 29C. Moreover, with suppression of the electromotive force generated in the electrodes 66a, 66b, the first oxygen pumping cell voltage Vp1 is reduced resulting in a reduced temperature dependency and oxygen concentration dependency in the $NO_x$ gas concentration measurement.

This effect is attributed to the fact that the first oxygen pumping cell voltage Vp1 required for pumping out excess oxygen is lowered so that there occurs no dissociation or decomposition of the NO gas other than oxygen-pumping-out in the first measuring chamber. Specifically, the NO gas flowing into the second measuring chamber is not decreased to prevent the $\Delta IP_2$ (gain) from being lowered.

Moreover, since the oxygen concentration gradient in the first measuring chamber 62 is decreased, the oxygen concentration becomes constant in the vicinity of the second diffusion aperture 63, so that the concentration of oxygen introduced into the second measuring chamber 64 for measuring the $NO_x$ concentration becomes constant. That is, the concentration of oxygen pumped out in the second measuring chamber 4 becomes constant ($Ip_2$ is stabilized) such that the $Ip_2$ value depends solely on the amount of NO dissociation or decomposition.

In the sensor of the reference example shown in FIG. 37, the electrodes 66a, 66b are extended over the entire length of the first measurement chamber 62, so that, at the distal end of the first measuring chamber 62 (between the ends of the electrodes 66a and 66b), an electromotive force opposite in direction to the first pumping cell voltage Vp1 may be generated, depending on the oxygen concentration difference inside and outside the first measuring chamber 62, such that, while oxygen is pumped out at the inlet side (directed to the first diffusion aperture 61) of the first measuring chamber 62, oxygen is pumped into the first measuring chamber 62 at the outlet side (directed to the second diffusion aperture 63). Conversely, with the sensor shown in FIG. 29, the distal end of the electrode 66a has been removed, so that, as shown in FIG. 29C, the electromotive force is prevented from being produced at the distal end of the first measuring chamber 62 (towards the second diffusion aperture 63 or at the outlet side of the first measuring chamber).

If at least the electrode of the first oxygen pumping cell provided on the wall surface of the first measuring chamber is too long, the first oxygen pumping cell voltage Vp1 is increased to cause $NO_x$ dissociation in the first measuring chamber. If, conversely, the electrode of the first oxygen pumping cell provided on the wall surface of the first measuring chamber is too short, oxygen pumping from the first measuring chamber becomes insufficient. Thus in both cases it results in a decreased gain of the second oxygen pumping cell current. Therefore, the length ratio of at least the electrode of the provided on the wall surface of the first measuring chamber to the overall length of the first measuring chamber along the flowing direction of the measuring gas in the first measuring chamber is set so that (electrode/overall length)=¼ or more, or ¾ or less and preferably 2/7 to 4/7, or 5/7 or less. In the present specification, the numerical range includes not only upper and lower limit values but also any optional intermediate values.

The $NO_x$ gas concentration sensor according to the present invention is characterized in that the first oxygen pumping cell 66, oxygen concentration measuring cell 67 and the second oxygen pumping cell 68 are provided in respective different solid electrolyte layers, as shown in FIG. 29. This reduces the leakage current flowing between the cell electrodes to permit accurate control of the oxygen concentration in the first measuring chamber 62. Preferably, insulating films or layers of alumina ceramic etc. are provided between the cells.

Preferably, heating layer(s) for heating the sensor is laminated between solid electrolyte layers. By providing the heating layer, the oxygen partial pressure measuring electrode can be maintained at a suitable temperature.

As a solid electrolyte of each cell, a solid solution of zirconia-yttria, a solid solution of zirconia-calcia ect. is employed. The porous electrodes formed by screen printing or firing on both surfaces of the thin plate-shaped solid electrolyte layer are preferably formed using platinum or rhodium exhibiting a catalytic operation or alloys thereof. It is preferred to use a porous ceramic material for the first and second diffusion apertures, e.g., porous alumina ceramics etc. Preferably, the heat generating part of the heater is formed of a complex material of ceramics and platinum or platinum alloys, while the lead portion is formed of platinum or a platinum alloy.

The measuring method of the present invention may be applied to a CO gas sensor or a HC gas sensor, in which case the influence of $H_2O$ is reduced to permit accurate measurement of the concentration of the measuring gas, as in the case of the $NO_x$ gas sensor.

Example C1

Referring to the drawings, example C1 of the present aspect C is explained.

FIGS. 29A to 29C illustrate a $NO_x$ gas concentration sensor according to an embodiment of the present aspect, where FIG. 29A is a cross-sectional view taken along the longitudinal direction, FIG. 29B is a plan view showing a first measuring chamber and FIG. 29C is an enlarged cross-sectional view showing essential portions of the first measuring chamber. The sensor of FIG. 29 includes a laminate comprising, in the following order, a layer of the first oxygen pumping cell 66 having a solid electrolyte layer and an electrode 66a (positive electrode) and a negative electrode 66b on both sides of the solid electrolyte layer, a layer of an oxygen concentration measuring cell 67 having another solid electrolyte layer and an oxygen concentration measuring cell 67 having oxygen partial pressure measuring electrodes formed on both sides of the solid electrolyte layer, a layer of solid electrolyte, and a layer of a second oxygen pumping cell 68 having a further (fourth) electrolyte layer and oxygen pumping electrodes on both side of this electrolyte layer. Between the layer of the first oxygen pumping cell 68 and the layer of the oxygen concentration measuring cell 67 is defined a first measuring chamber 62 by an insulating layer on left and right sides and a solid electrolyte layer on upper and lower sides in the drawing. Similarly, a second measuring chamber 64 is defined above the second oxygen pumping cell 68. The first measuring chamber 62 is provided with a first diffusion aperture 61 and a second diffusion aperture 63 for introducing the measuring gas via a diffusion resistance. The second diffusion aperture 63 passes through layers of the oxygen concentration measuring cell 67 and the solid electrolyte layer for establishing communication between the first and second measuring chambers 62, 64 for sending a gas containing at least $NO_x$ and $O_2$ from the first measuring chamber 62 via the diffusion resistance into the second measuring chamber 64.

Between the neighboring solid electrolyte layers are interposed insulating layers formed of alumina ceramics. Although not shown, heater layers for heating the sensor are bonded by cement layers for sandwiching the sensor in its entirety. The electrodes are connected to a device outside the sensor, such as a power source, via a lead wire pattern formed between the layers.

One of the features of the sensor is that the first measuring chamber 62 and the second measuring chamber 64 are substantially in register with each other in vertical direction. Another feature is that the first diffusion aperture 61 is formed on both sides of the sensor, instead of on the distal thereof, there is charged a porous material in the second measuring chamber 64, insulating films are interposed between every neighboring solid electrolyte layers, and the cell electrodes are insulated from each other. The second measuring chamber 64, delimiting a cavity, may also be filled with a porous material.

The feature of the sensor of FIG. 1 as compared to the sensor of FIG. 37 as a Control example, is that the lengths along the flowing direction of the measuring gas from the first diffusion aperture to the second aperture (in the longitudinal direction) of the positive electrode 66a and the negative electrode 66b of the first oxygen pumping cell 66 are shorter than the length of the first measuring chamber (A>B) and that the electrodes 66a, 66b are not formed reaching up to directly above the second diffusion aperture 63.

The operation of the electrodes 66a, 66b is the same as that explained in the description of the preferred embodiment and hence is not explained for clarity.

Using the sensor of the Example of FIG. 29 and the sensor of Control example shown in FIG. 37, the $NO_x$ gas concentration was measured. The length along the long side, width (along the short side) and thickness (in the laminating direction) of the sensor are 50 mm, 4 mm and 1.3 mm, respectively. The thickness of the first oxygen pumping cell is 0.3 mm, the length B along the long side and that along the short side of the first measuring chamber of the electrodes 66a, 66b are 4 mm and 2 mm, respectively. The length along the long side, that along the short side and hieght of the first measuring chamber are 7 mm, 2 mm and 50 $\mu$m, respectively. The length along the long side, that along the short side and thickness of the first diffusion aperture are 2 mm, 1 mm and 50 $\mu$m, respectively. The second diffusion aperture has a diameter of 1 mm and a distance thereto from the end (right end) of the first diffusion aperture is 5.5 mm. The sensor of the Control example (FIG. 37) is of the same size as the sensor of the embodiment of FIG. 29 except that the length along the long side of the electrodes 66a, 66b is 7 mm (A=B).

The method for producing the sensor used for measurement and the layout thereof are hereinafter explained. The method for producing the sensor and the layout thereof are shown in FIG. 22. The layout of the example and that of the Control example are the same except the different length of the electrodes of the first oxygen pumping cell, as shown in FIGS. 29 and 37.

Referring to FIGS. 22(A),(B), $ZrO_2$ sheets, pastes for electrodes and so forth are laminated from upper left to lower left, upper right and to lower right in the drawing to form a unitary sensor. In the sensors used for measurement, protective coating paste 3, shown in FIG. 22, is provided, although the protective coating is not shown in FIGS. 29 or 37. Meanwhile, a manufacturing example C for various components such as $ZrO_2$ sheets is basically the same as the manufacturing example A shown in FIG. 22 as to the steps including the molding of the $ZrO_2$ sheets, printing pastes, pellets, method for laminating $ZrO_2$, removal of organic binder and firing step, except additional steps, as later explained.

Using the $NO_x$ gas concentration sensor, thus produced, tests were conducted for measuring the NO gas concentration in the measuring gas. The measured results are shown in Tables C1 and C2 and are shown in a summary in FIGS. 30 to 36. The measurement conditions common to the test examples as later explained include measuring gas components NO, $O_2$ and $CO_2$ of 0 to 1500 ppm, 1 to 16% and 10%, respectively, with the balance being $N_2$, exhaust gas (measuring gas) temperature of 300° C., heater power of 18 to 25 W (20 W corresponds to a sensor temperature of 800° C.).

TABLE C1

Relation between Oxygen Concentration and Offset, Gain, Vp1 Oxygen Pump Electrode (of 4 mm)

| Oxygen Concentration 0.2% | IP2 Offset (μA) | | Δ IP2 Gain (μA) | | VP1 (mV) | |
|---|---|---|---|---|---|---|
| | Improved | Control | Improved | Control | Improved | Control |
| 1 | 6.475 | 7.45 | 13.31 | 12.31 | 151.2 | 184.05 |
| 7 | 5.89 | 4.63 | 13.51 | 13.155 | 231.3 | 274.9 |
| 16 | 5.475 | 4.265 | 13.56 | 13.28 | 331.9 | 388.7 |

TABLE C2

Relation between Temperature and Offset, Gain, Vp1 Oxygen Pump Electrode (of 4 mm)

| Heater Power (W) | Offset (μA) | Gain (μA) | VP1 (mV) |
|---|---|---|---|
| 24.985 | 5.385 | 12.535 | 225.4 |
| 22.99 | 4.78 | 12.255 | 229.65 |
| 20.969 | 4.16 | 11.955 | 254.35 |
| 18.945 | 5.115 | 11.36 | 354.4 |
| 24.989 | 5.535 | 13.67 | 268.45 |
| 22.995 | 3.61 | 13.67 | 290.8 |
| 20.976 | 2.465 | 13.1 | 368.45 |
| 19.05 | 2.32 | 10.47 | 501.8 |

TABLE C3

Relation between Oxygen Concentration and Offset, Gain, VP1 Oxygen Pump Electrode (of 4 mm)

| Heater Power (W) | Offset (μA) | Gain (μA) | VP1 (mV) |
|---|---|---|---|
| 21.47 | −30.01 | 1.4 | 994.8 |

Test Example C1

Figure 30:
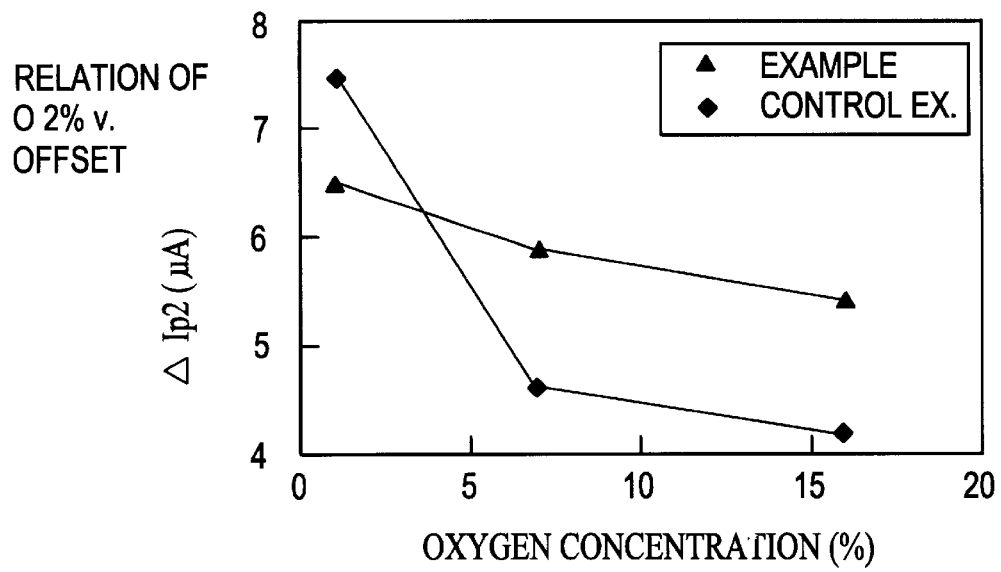
FIG. 30 is a graph showing oxygen concentration dependency of the second oxygen ion pumping current $Ip_2$ (offset) according to an embodiment of the present invention and a Control Example.

For various values of the oxygen concentration and for NO: 0%, fluctuations in the offset value of the second oxygen pumping current were measured. The offset is the amount of change of $Ip_2$ ($\Delta Ip_2$) when NO is not injected into the measuring gas. A smaller value of the offset is preferred. It is desirable for the offset to be less sensitive to various extraneous conditions, such as oxygen concentration or temperature in the measuring gas atmosphere and hence less susceptible to fluctuations. The offset corresponds to the concentration of the residual oxygen left unpumped in the first measuring chamber 62 (see FIG. 29). FIG. 30 shows the results of the test example C1. In FIG. 30, which is a graph showing oxygen concentration dependency of the offset of the second oxygen pumping current $Ip_2$, triangular and diamond marks denote measured data by the sensor of the example and the sensor of the Control example, respectively. Referring to FIG. 30, the sensor of the Example undergoes $Ip_2$ changes of the order of 1 μA relative to amounts of change of 1 to 16% of the oxygen concentration, thus indicating that the oxygen concentration dependency of the gain is lower than in Control example.

Test Example C2

Figure 31:
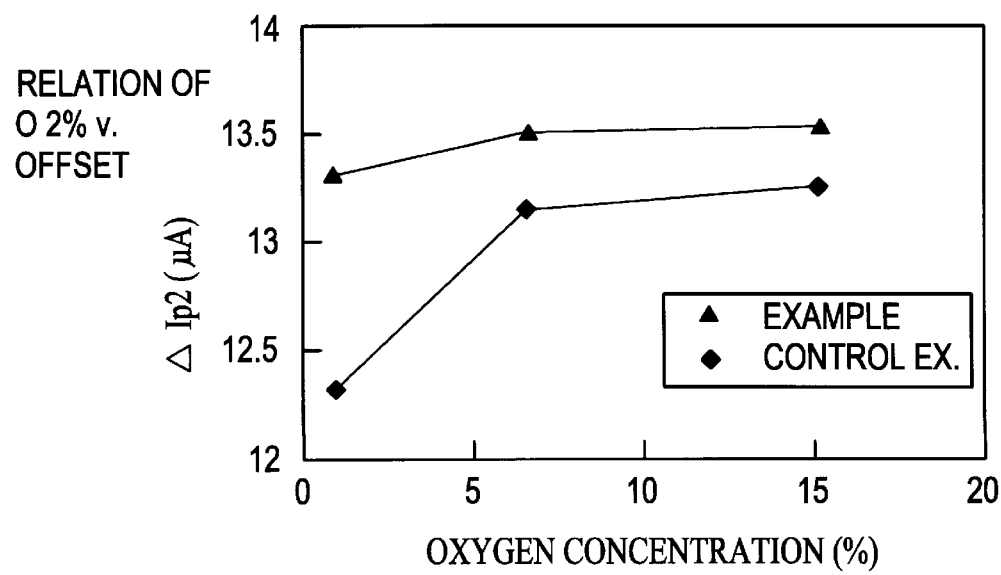
FIG. 31 is a graph showing oxygen concentration dependency of the second oxygen ion pumping current $\Delta Ip_2$ (gain) according to an embodiment of the present invention and a Control Example.
Figure 32:
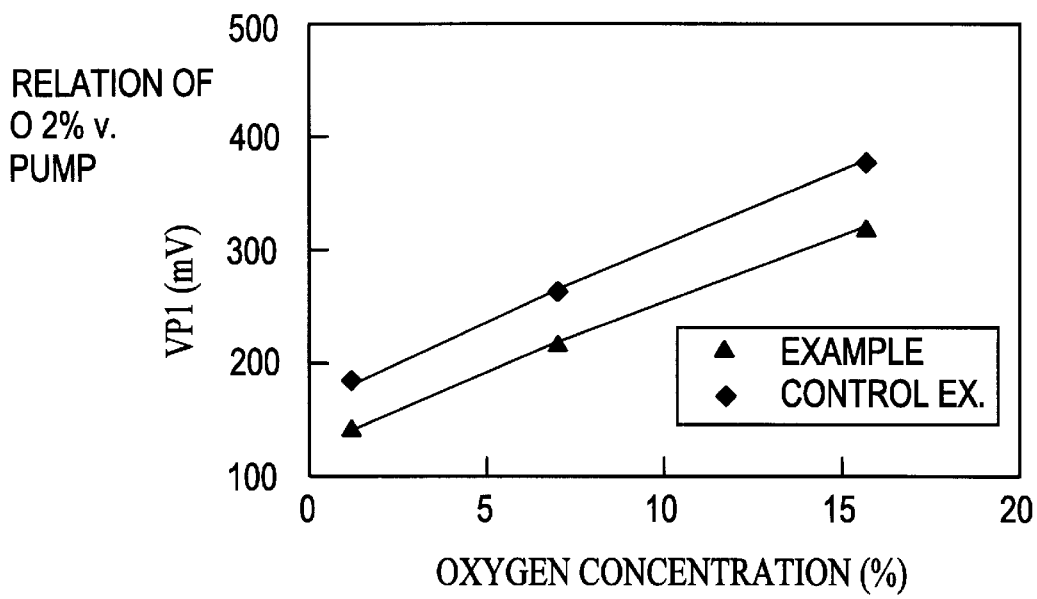
FIG. 32 is a graph showing the oxygen concentration dependency of a first oxygen pumping voltage $Vp1$ according to an embodiment of the present invention and a Control Example.

NO was injected to 1500 ppm into the measuring gas, and measurements were made of the gain of the second oxygen pumping current for oxygen concentration values of 1 to 16%. The gain represents the amount of change in Ip2 when NO is injected in a determined amount. FIG. 32 shows the results of the test example C2. In FIG. 32, which is a graph showing the oxygen concentration dependency of the gain Δ Ip2 of the second oxygen pump current, triangular and diamond marks represent measured data by the sensor of the Example and that of the Control example, respectively. It is seen in FIG. 31 that, with the sensor of the Example, $Ip_2$ gain is scarcely changed versus changes of 1 to 16% of the oxygen concentration, thus indicating that the temperature dependency is improved over the Control example.

Test Example C3

The first oxygen pumping cell voltage Vp1 across the first oxygen pumping electrodes with respect to changes in the oxygen concentration was measured for NO: 0%. The oxygen pumping cell voltage Vp1 is a voltage required for pumping out excess oxygen in the first measuring chamber. FIG. 32 shows the results of the test example C3. In FIG. 32, which is a graph showing the oxygen concentration dependency of the first oxygen pumping cell voltage Vp1, triangular and diamond marks denote measured data by the sensor of the example and the sensor of the Control example, respectively. It is seen from FIG. 32 that the sensor of the Example scarcely undergoes changes in the oxygen pump cell voltage $Ip_1$ versus the amounts of changes of 1 to 16% of the oxygen concentration, thus indicating that the oxygen concentration dependency of the oxygen pump cell voltage Vp1 reduced as compared with the Control example.

Test Example C4

Figure 33:
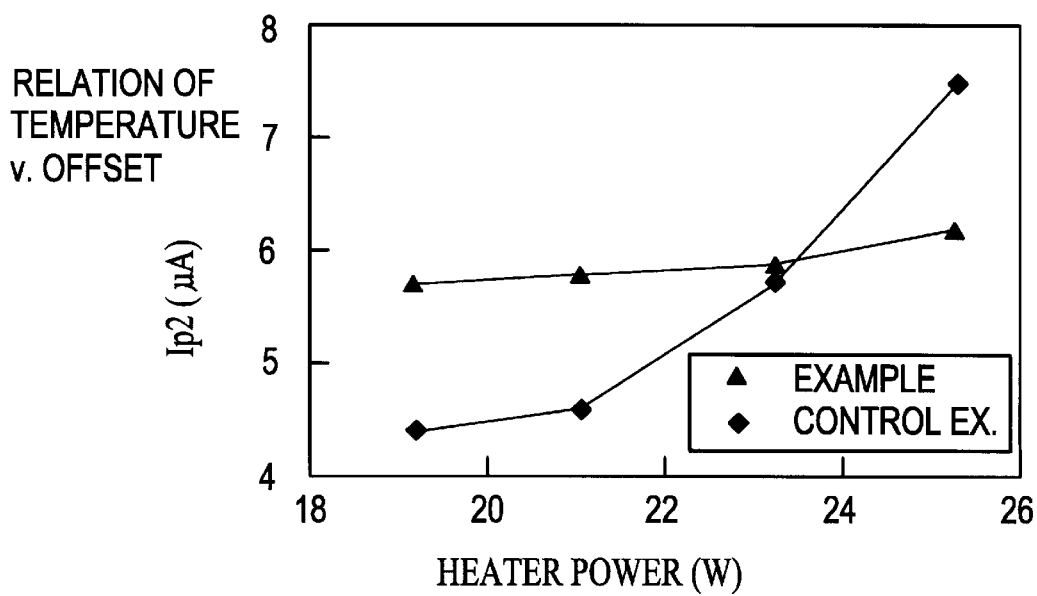
FIG. 33 is a graph showing the temperature (heater power) dependency of the second oxygen ion pumping current $\Delta Ip_2$ (offset) according to an embodiment of the present invention and a Control Example.

For NO: 0%, 7% $O_2$ was injected to the measuring gas, and variation in offset value of the second oxygen pumping cell current Ip2 versus changes in heater power was measured. FIG. 33 shows the results of the test example C4. In FIG. 33, which is a graph showing the temperature (heater power) dependency of the offset of the second oxygen pumping cell current Ip2, triangular and diamond marks denote measured data by the sensor of the Example and the sensor of the Control example, respectively. It is seen from FIG. 33 that, with the sensor of the Example, the Ip2 offset is scarcely changed versus changes of 18 to 25 W of the heater power, thus indicating an improved temperature dependency.

Test Example C5

Figure 34:
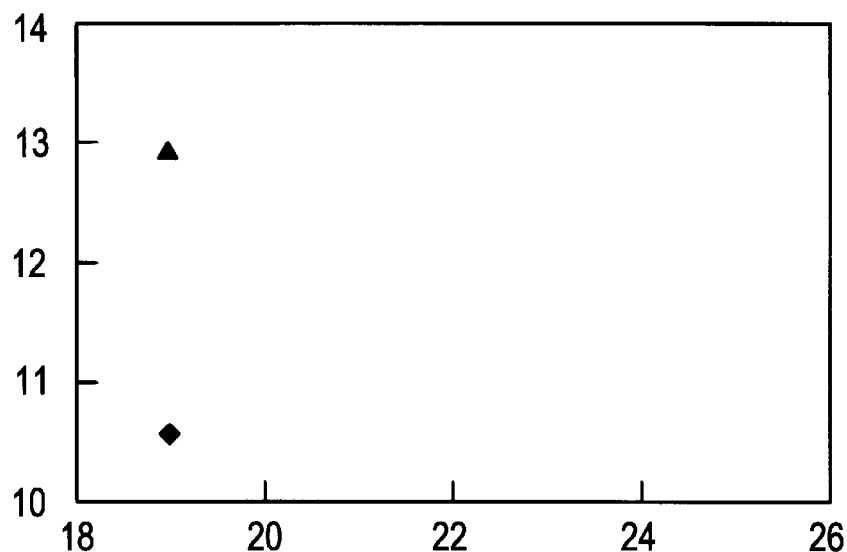
FIG. 34 is a graph showing the temperature (heater power) dependency of the second oxygen ion pumping current $\Delta Ip_2$ (gain) according to an embodiment of the present invention and a Control Example.

For NO: 1500 ppm, 7% of $O_2$ was charged into the measuring gas, and measurements were made of fluctuations in the gain value of the second oxygen pumping current $Ip_2$ upon varying values of the heater power. FIG. 34 shows the results of the test example 5. In FIG. 34, which is a graph showing the temperature (heater power) dependency of the second oxygen pump current gain $\Delta IP_2$, triangular and diamond marks represent measured data by the sensor of the Example and that of the Control example, respectively. It is seen in FIG. 34 that, with the sensor of the Example, $Ip_2$ gain changes become substantially constant versus changes of the heater power ranging, thus indicating that the temperature dependency is improved over the Control example.

Test Example C6

Figure 35:
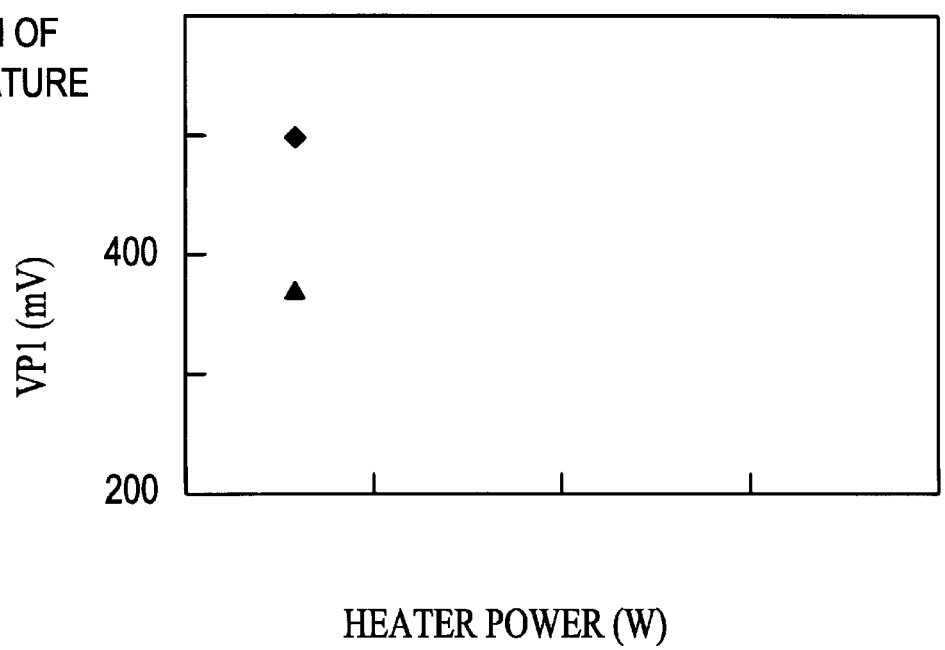
FIG. 35 is a graph showing the temperature (heater power) dependency of the first oxygen ion pumping cell voltage $Vp1$ according to an embodiment of the present invention and a Control Example.

For NO: 0%, 7% of $O_2$ was charged into the measuring gas, and measurements were made of the changes in the first oxygen pumping cell voltage Vp1 for varying values of the heater power. FIG. 35 shows the results of test example C6. In FIG. 35, which is a graph showing the temperature (heater power) dependency of the first oxygen pumping cell voltage Vp1, triangular and diamond marks represent measured data by the sensor of the Example and that of the Control example, respectively. It is seen that, in the heater of the Example, the amount of change in Vp1 has been significantly reduced versus changes in heater power of 18 to 25 W.

Figure 36:
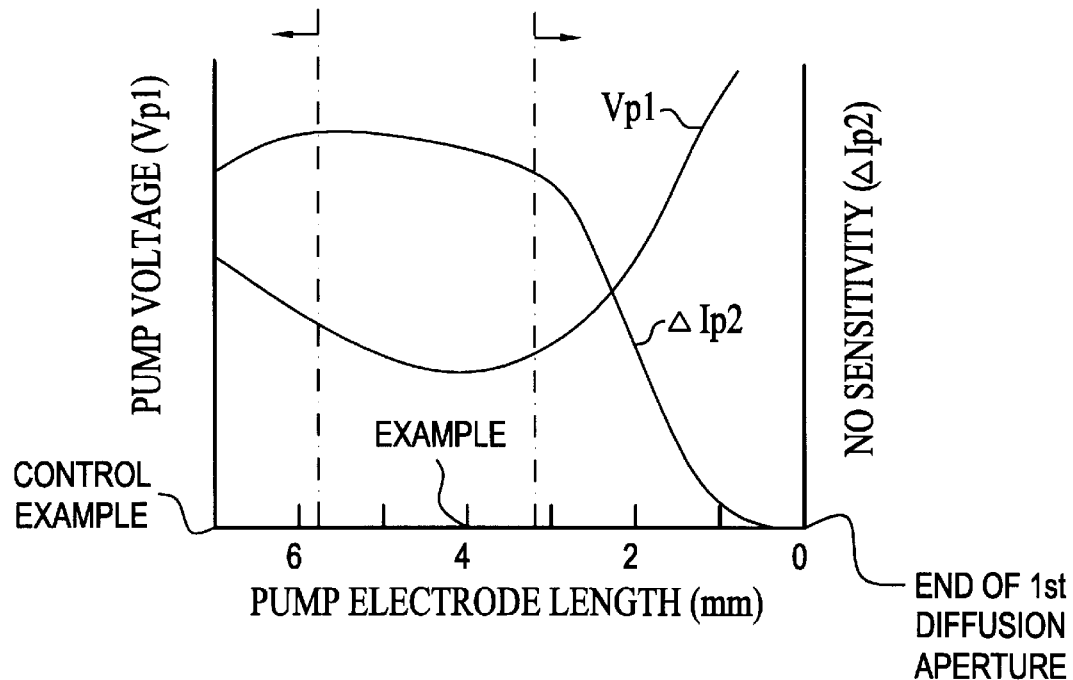
FIG. 36 is a graph showing the relation between the length of the first oxygen pump electrode and the voltage $Vp1$ of the first oxygen ion pump electrode and the second oxygen pump current $\Delta Ip_2$ according to an embodiment of the present invention and a Control Example.

From the results of the above Test Examples C1 to C6 (FIGS. 30 to 35), it is seen that, if the electrodes of the first oxygen pumping cell (at least the electrode exposed the first measuring chamber) is longer than the length of the first measuring chamber, the first oxygen pumping cell voltage Vp1 tends to be increased under the effect of the electromotive force generated at the distal end of the first oxygen pumping cell (the distal end of the electrode opposite to the first diffusion aperture), with the effective voltage being then decreased, because the adversely pumped-in oxygen into the first measuring chamber is pumped out for compensating for the decreased effective voltage for maintaining the oxygen concentration in the first measuring chamber at a pre-set concentration. It is also seen that, if the electrodes of the first oxygen pumping cell is shorter than the length of the first measuring chamber, the gain of the second oxygen pumping cell voltage Ip2 tends to be decreased due to insufficient pumping capability (more oxygen is diffused towards the second measuring chamber so that measurement of a trace amount of the $NO_x$ gas concentration becomes inaccurate). FIG. 36 shows the relation between the electrode length of the first oxygen pumping cell and the first oxygen pumping cell voltage Vp1 and the second oxygen pumping cell current $\Delta$ Ip2 (gain). FIG. 36 shows that the length of the first oxygen pumping electrode equal to 4 mm for the length of the first measuring chamber of 7 mm, that is a ratio of the electrode length to the first measuring chamber length of 4/7, is particularly preferred. The length of the first oxygen pump electrode approximately of 2 to 5.4 mm is preferred, while the length approximately of 3.5 to 5 mm is particularly preferred.

In the state where the electrode of the first oxygen pumping cell is so long as to cover the second diffusion aperture, it is seen that the generated EMF gives rise to in crease the first oxygen pumping cell voltage Vp1 and decrease $\Delta$ Ip2. On the other hand, the electrodes of the first oxygen pumping cell are too short, it si seen that the Ip2 output will decrease because of shortage in the pumping capability.

It is seen from above that, with the $NO_x$ gas concentration sensor of the present aspect, the electro-motive force (EMF) produced in the first measuring chamber is suppressed, and the first oxygen pumping cell voltage Vp1 is decreased to suppress the dissociation and decomposition of the NO gas in the first measuring chamber, thus improving the oxygen- and temperature dependency of $NO_x$ gas concentration measurement for enabling more accurate measurement of the $NO_x$ gas concentration.

Aspect D

Preferred Embodiments

In connection with the fifth object of the present invention, the present inventors have directed attention to the fact that (a) the generated electromotive force (EMF) of the second oxygen pumping cell depends on fluctuations in the oxygen concentration of the exhaust gas atmosphere and that (b) the value of the current $Ip_2$ flowing in the second oxygen pumping cell depends on changes in the oxygen concentration in the exhaust gas.

As a result of our further researches, the present inventors have found that the above problem can be resolved by providing an electrode as a counter-electrode of the oxygen pumping cell in the second measuring chamber (cavity) (oxygen pumping out side) within a device (between laminated solid electrolyte layers) for pumping out oxygen by a lead portion of the electrode or a part thereof and by discharging the pumped-out oxygen by following various means.

Figure 38:
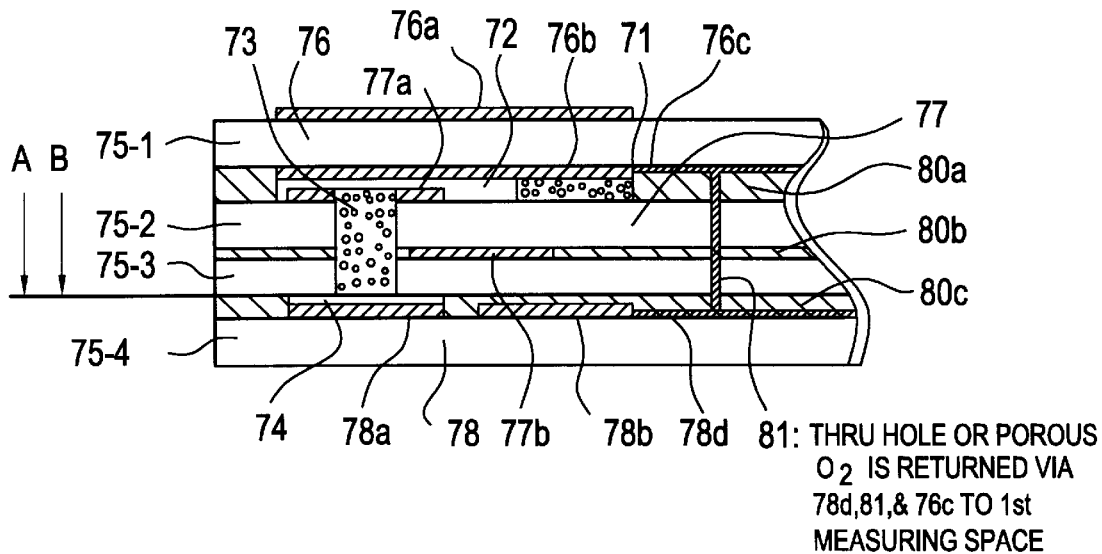
FIG. 38 is a cross-sectional view taken along the long side of a $NO_x$ gas concentration sensor according to one embodiment of the present invention for explaining the structure of the sensor.

(1) The pumped out oxygen is discharged out into the first measuring chamber via the lead portion or part thereof and a through-hole (see FIG. 38).

Figure 39:
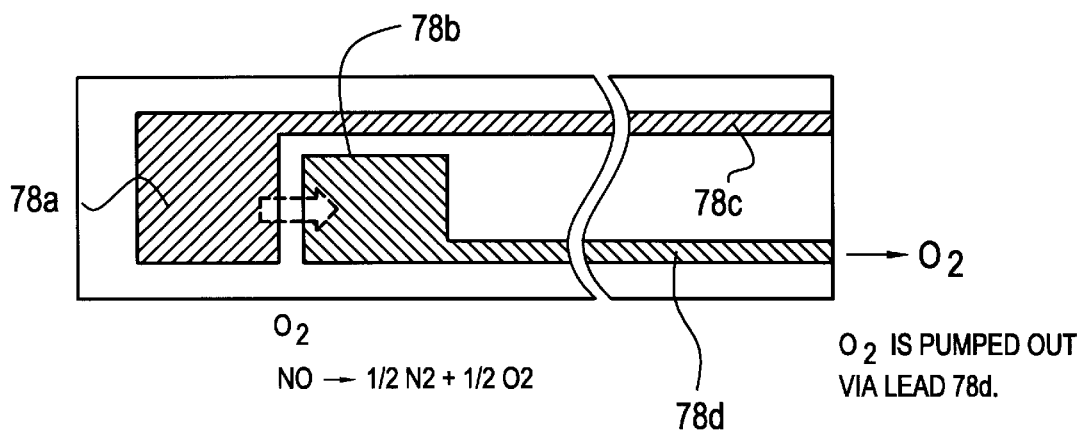
FIG. 39 is a cross-sectional plan view taken along arrow A in FIG. 38.

(2) The pumped out oxygen is discharged via the lead portion into atmosphere or exhaust gas (see FIG. 39).

Figure 40:
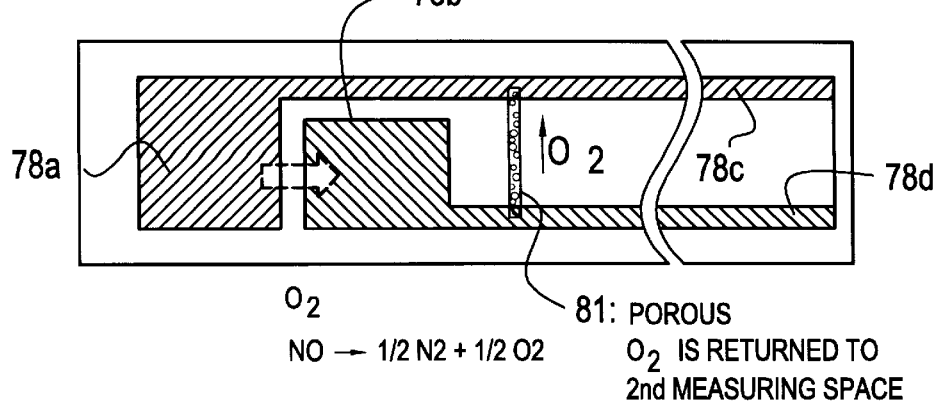
FIG. 40 is a cross-sectional plan view showing a variant of the $NO_x$ gas concentration sensor embodying the present invention (equivalent to the cross-sectional plan view taken along arrow B in FIG. 38).

(3) The pumped out oxygen is discharged via a part of the lead and a porous portion into the second measuring chamger (see FIG. 40).

By the above structure and means, the external electrode of the second measuring chamber as the counter-electrode to the electrode of the oxygen pumping cell in the second measuring chamber is interrupted from the exhaust gas atmosphere, so that the oxygen pumped out of the second measuring chamber is pooled, thus stabilizing the oxygen concentration in the vicinity of the electrode and the electromotive force generated across the electrodes of the second measuring chamber. The result is a decreased dependency on changes in the oxygen concentration in the exhaust gas of the pump current $Ip_2$ flowing in the second oxygen pumping cell thus assuring accurate measurement of the $NO_x$ gas concentration even in the low oxygen concentration atmosphere.

With the sensor of the D1 aspect of the present invention, as described above, the electrode provided outside of the second measuring chamber, referred to hereinafter as "electrode of the second oxygen pumping cell provided outside of the second measuring chamber"), is arranged so as not to be in direct contact with air outside the sensor and diffusion resistance means discharging the oxygen with a diffusion resistance is provided around the electrode of the second oxygen ion pump cell provided outside of the second measuring chamber.

The sensor having this feature preferably includes a first measuring chamber in which a measuring gas is introduced via a first diffusion resistance, oxygen partial pressure measuring electrodes measuring the oxygen partial pressure in the measuring gas in the first measuring chamber, a first oxygen pumping cell pumping out a sufficient amount of oxygen in the measuring gas out of the first measuring chamber, based on the potential of the oxygen partial pressure measuring electrodes, to such an extent as substantially not to cause decomposition of oxygen in the measuring gas by $NO_2$, a second measuring chamber into which the gas is introduced out of the first measuring chamber via a second diffusion resistance and a second oxygen pumping cell having on the inside and outside of the second measuring chamber a pair of electrodes across which the voltage is impressed for decomposing $NO_x$ in the second measuring chamber, with the current flowing therein by pumping out the dissociated oxygen in an amount corresponding to the $NO_x$ gas concentration.

With a sensor of aspect D2 of the present invention, at least the diffusion resistance means is a lead portion for electrical connection to an external electrode of the second measuring chamber of the second oxygen (ion) pumping cell, or a portion thereof.

With a sensor of aspect D3 of the present invention, the external electrode of the second measuring chamber of the second oxygen pump cell is communicated via a lead portion by a diffusion resistance with the atmosphere of the sensor.

With a sensor of aspect D4 of the present invention, the external electrode of the second measuring chamber of said second oxygen pumping cell is arranged between insulating layers and/or solid electrolyte layers constituting the laminated structure of the sensor and the diffusion resistance means is connected to the electrode, so that the external electrode of the second measuring chamber of the second oxygen pumping cell is not directly contacted with the atmosphere of the sensor. The external electrode of the second measuring chamber of the second oxygen pumping cell is indirectly connected via diffusion resistance means to the atmosphere of the sensor.

With a sensor of aspect D5 of the present invention, the diffusion resistance means is communicated with a gas channel (or path) provided within the sensor. The gas channel is communicated with an electrode of the first oxygen pumping cell, a lead portion of the electrode or with the first measuring chamber.

With a sensor of aspect D6 of the present invention, diffusion resistance means is communicated with a gas channel provided in the sensor. The gas channel is communicated with an electrode of the pair of electrodes of the second oxygen pumping cell provided inside of the second measuring chamber, referred to hereinafter as "electrode of the second oxygen pumping cell provided inside of the second measuring chamber", a lead portion thereof or with the second measuring chamber.

With a sensor of aspect D7 of the present invention, the lead portion communicated with the gas channel is contacted with atmosphere.

With a sensor of aspect D8 of the present invention, a solid electrolyte layer provided with the pair of electrodes of the second oxygen pumping cell is laminated between the solid electrolyte layer provided with the oxygen partial pressure measuring electrode and the second measuring chamber.

With a sensor of aspect D9 of the present invention, the paired electrodes of the second oxygen pumping cell are provided on the same surface of the solid electrolyte layer constituting the laminated structure of the sensor.

With a sensor of aspect D10 of the present invention, the electrode of the second oxygen pumping cell provided inside of the second measuring chamber is provided surrounding an opening of the second diffusion resistance in the second measuring chamber.

A sensor of aspect D11 of the present invention includes a first oxygen pumping cell for pumping out oxygen from the measuring gas so that $NO_x$ is not decomposed and a second oxygen pumping cell having a pair of electrodes in a solid electrolyte layer, the electrical voltage being impressed across said electrodes for decomposing $NO_x$ in the residual gas for pumping out oxygen for causing the current to flow in an amount corresponding to the amount of decomposed $NO_x$. The sensor has diffusion resistance means interrupting direct contact with atmosphere of the sensor of the electrode of the second oxygen pumping cell provided outside of the second measuring chamber.

By the diffusion resistance, the diffusion resistance means diffuses the oxygen pumped out by the second oxygen pumping cell for alleviating fluctuations in the oxygen concentration around the electrode.

The measurement principle of the $NO_x$ gas concentration sensor having two sets of diffusion resistance units, oxygen pumping cells and measuring chambers, according to an embodiment of the present aspect, is hereinafter explained.
(1) The exhaust gas flows into the first measuring chamber via a first diffusion aperture having diffusion resistance.
(2) Using the first oxygen pumping cell, oxygen in the first measuring chamber is pumped out to the extent that $NO_x$ is substantially not decomposed (the oxygen partial pressure in the first measuring chamber is controlled by an output signal of an oxygen partial pressure detection electrode).
(3) The gas in the first measuring chamber (concentration-controlled $O_2$ gas plus $NO_x$ gas) flows into the second measuring chamber via a second diffusion aperture having diffusion resistance.
(4) By further pumping out oxygen by the second oxygen pumping cell, the $NO_x$ gas in the second measuring chamber is decomposed into $N_2+O_2$.
(5) Since there is a linear relationship between the pump current $Ip_2$ flowing at this time through the second pumping cell and the $NO_x$ gas concentration, the $NO_x$ gas concentration can be measured by measuring $Ip_2$.

If there is an oxygen concentration difference between the paired electrodes of the second oxygen pumping cell, an electromotive force is generated in the second oxygen pumping cell, such that, even if the voltage impressed across the cell is controlled to a constant value, the effective pump voltage varies. The effective pump voltage meas 'a difference between the impressed voltage and the electromotive force'. Therefore, if the oxygen concentration difference varies, $Ip_2$ varies by the oxygen concentration instead of by the $NO_x$ gas concentration. Thus, an embodiment of the present invention includes means for maintaining a constant oxygen concentration difference across paired electrodes of the second oxygen pumping cell, that is means for stabilizing the oxygen concentration around the electrode provided outside the second measuring chamber of the second oxygen pumping cell. Such means stabilize the electromotive force varied with fluctuations in the oxygen concentration. Since the impressed voltage is made constant, the effective pump voltage is stabilized thus enabling accurate $NO_x$ gas concentration independent of the oxygen concentration. Preferably, as means for interrupting the electrode outside of the second measuring chamber of the second oxygen pumping cell, a protective layer, such as an alumina insulating layer and/or a solid electrolyte layer of zirconia, is provided for breaking direct contact between the electrode and air outside the sensor. In addition, as means for discharging pumped-out oxygen, there is provided diffusion resistance means connected to the outside electrode for diffusing oxygen. Thus, the solid electrolyte layer, insulating layer and diffusion resistance means break the direct contact between the electrode outside of the second measuring chamber of the second oxygen pumping cell and air outside the sensor (atmosphere or measuring gas such as exhaust gas), while the diffusion resistance means assure oxygen discharge via diffusion resistance thus stabilizing the oxygen concentration around the electrode. Preferably, the diffusion resistance means is formed by a lead portion of a porous material, such as platinum alloy, rhodium alloy and alloys thereof with ceramics for eliminating the necessity of providing separate diffusion resistance means and electrical connection means of the electrodes, thus achieving effective utilization of a minimum spacing and reduction of the number of steps and materials.

Preferably, a solid electrolyte layer having paired electrodes of the second oxygen pumping cell is laminated between the solid electrolyte layer provided with the oxygen partial pressure measuring electrodes (oxygen concentration measuring cell) and the second measuring chamber. That is, the second oxygen pumping cell is arranged between the oxygen concentration measuring cell and the layer of the second measuring chamber. Preferably, for preventing current leakage between the electrodes, an insulating layer is provided between the solid electrolyte layer having paired electrodes of the second oxygen pumping cell and the solid electrolyte layer provided with the oxygen partial pressure measuring electrode. By arranging the second oxygen pumping cell in this manner, the solid electrolyte layer is utilized more effectively than if the second oxygen pumping cell is arranged between the second measuring chamber and the outside of the sensor, and the solid electrolyte layer may be reduced further, while the laminating thickness may be reduced to render the sensor more compact.

A preferred $NO_x$ gas concentration sensor according to the present invention is characterized in that the first oxygen pumping cell 76, oxygen concentration measuring cell 77 and the second oxygen pumping cell 78 are provided on different solid electrolyte layers (see FIG. 38). This diminishes the leakage current flowing between the cell electrodes for assuring accurate control of the oxygen concentration in the first measuring chamber. Also preferably, an insulator or an insulating film is provided between the cells.

Also preferably, a heater layer for heating the sensor is laminated between layered solid electrolyte layers. Such heater layer stabilizes the capability of the first and second oxygen pumps.

As the solid electrolyte of each cell, a solid solution of zirconia-yttria or a solid solution of zirconia-calcia etc. is employed. The porous electrodes formed by screen printing or firing on both surfaces of the thin plate-shaped solid electrolyte layers are preferably formed using platinum or rhodium exhibiting a catalytic operation or alloys thereof. The first and second diffusion apertures are preferably formed of porous ceramics, such as porous alumina ceramics. Preferably, the heat generating part of the heater is formed of a complex material of ceramics and platinum or platinum alloys, while the lead portion is formed using platinum or a platinum alloy.

The measuring method of the present invention may be applied to a CO gas sensor or a HC gas sensor, in which case the effect of $H_2O$ is reduced to permit accurate measurement of the concentration of the measuring gas, as in the case of the $NO_x$ gas sensor.

Examples D

Referring to FIGS. 38 to 46, aspect D examples of the present invention will be explained.

Example D1

FIG. 38 illustrates the structure of a $NO_x$ gas concentration sensor embodying the present invention.

The sensor shown in FIG. 38 includes a first oxygen concentration measuring cell 76, a second oxygen concentration measuring cell 77 and a second oxygen pumping cell 78, laminated in this order. The first oxygen pumping cell 76 has a pair of electrodes 76a, 76b formed on both sides of a solid electrolyte layer 75-1. The second oxygen concentration measuring cell 77 has a pair of oxygen partial pressure measuring electrodes 77a, 77b formed on both sides of a solid electrolyte layer 75-2, while the second oxygen pumping cell 78 has a pair of electrodes on the surfaces of the solid electrolyte layers 75-3 and 75-4, that is, an electrode 78a inside of the second measuring chamber of the second oxygen pumping cell 78 and an electrode 78b outside of the second measuring chamber of the second oxygen pumping cell 78. Between the solid electrolyte layers 75-1, 75-2, 75-3 and 75-4 are formed insulating layers 80a, 80b and 80c. In an interlayer spacing between the first oxygen pumping cell 76 and the oxygen concentration measuring cell 77 is defined a first measuring chamber 72 by left and right insulating layers 80a and upper and lower solid electrolyte layers 75-1 and 75-2. Similarly, above the second oxygen pumping cell 78, a second measuring chamber 74 is defined by the insulating layer 80c and the solid electrolyte layers 75-3 and 75-4. On one side of the first measuring chamber 72 on both sides along the short-side direction of the sensor (on the front side and back sides in FIG. 38) is formed a first diffusion aperture 71 having diffusion resistance. On the opposite side of the first measuring chamber 72 is formed an opening of the second diffusion aperture 73 at a spacing from the first diffusion aperture 71. The second diffusion aperture 73 passes thorough the oxygen concentration measuring cell 77 and the solid electrolyte layer 75-3 for establishing communication between the first and second measuring chambers 72, 74 with diffusion resistance.

In the present sensor, the electrodes 78a and 78b of a porous material, such as platinum or rhodium alloy, are formed on the same surface of the solid electrolyte layer 75-4 of the second oxygen pumping cell 78. Although the electrodes 78a and 78b are isolated from each other by the insulating layer 80c, oxygen ion conduction occurs via the solid electrolyte layer 75-4 to produce a current $Ip_2$. The electrode 78b is prevented by the solid electrolyte layer 75-4, an insulating layer 80c and a lead portion 78d from having direct contact with air outside the sensor, and can discharge oxygen pumped out by the second oxygen pumping cell 78 via the porous lead portion 78d having the diffusion resistance. To the electrodes 78a, 78b are electrically connected a lead 78c, not shown, and a lead 78d, respectively. The lead portion 78d electrically connected to the electrode 78b outside the second measuring chamber 74 is porous to permit oxygen ions to be diffused. Thus, oxygen decomposed from the $NO_x$ gas and pumped out from electrode 78a to electrode 78b by the second oxygen pumping cell 78 as indicated by arrow in FIG. 39 is discharged via lead portion 78d.

This oxygen, discharged via the lead portion 78d, is discharged via the porous lead portion 76c of the first oxygen pumping cell 76 into the first measuring chamber 72 via a through-hole (or pores of a porous material) 81 as a gas channel communicating the lead portion 78d with the porous lead portion 76c of the first measuring chamber 72 shown in FIG. 38 and thence into air outside the sensor.

The measurement principle of the sensor of FIG. 38 is as described above at the preferred embodiments of the invention. That is, an electromotive force corresponding to the oxygen concentration in the measuring gas introduced on diffusion through the first diffusion aperture 71 into the first measuring chamber 72 is generated across the electrodes 77a, 77b of the oxygen concentration measuring cell 77. The voltage impressed across the first oxygen pumping cell 76 is controlled so that the voltage by this electromotive force will be constant (optionally by digital or analog control by a micro-computer). Excess oxygen is pumped out and the measuring gas having a pre-set oxygen concentration is diffused via second diffusion aperture 73 into the second measuring chamber 74. Any residual oxygen is further pumped out by voltage impressed across the electrodes 78a, 78b of the second oxygen pumping cell 78. By the catalytic action of the electrodes of the platinum alloy or rhodium alloy, $NO_x$ is decomposed into $N_2$ and $O_2$. This $O_2$ is converted into ions migrating through the solid electrolyte layer of the second oxygen pumping cell 78 so that the current $Ip_2$ corresponding to the amount of the decomposed $NO_x$ flows between the electrodes 78a, 78b of the second oxygen pumping cell 78 provided inside and outside the second measuring chamber 74. The $NO_2$ gas concentration can be measured by measuring the current $Ip_2$.

With the present sensor, in which the electrode 78b as a counter-electrode of the electrode 78a of the second oxygen pumping cell 78 is mounted in the inside of the device (between the layered solid electrolytes), the solid electrolyte layer 75-4 and the insulating layer 80c serve as protection means for the electrode 78b, while the lead portion 78d serves as the diffusion resistance means. Thus the electrode 78b is isolated from the atmosphere of the measuring gas (exhaust gas) so as to be out of direct contact with outside air, while pumped-out oxygen is pooled in the vicinity of the electrode 78b, thus stabilizing the oxygen concentration around or in the vicinity of the electrode 78b and the electro-motive force generated across the electrodes 78a, 78b of the second oxygen pumping cell 78. Moreover, since the generated electro-motive force is stabilized, the effective pump voltage of the pump voltage Vp2 impressed across the second oxygen pumping cell 78 (Vp2−electro-motive force) is stabilized for decreasing oxygen concentration dependency of measurement of the $NO_x$ gas concentration.

Figure 43:
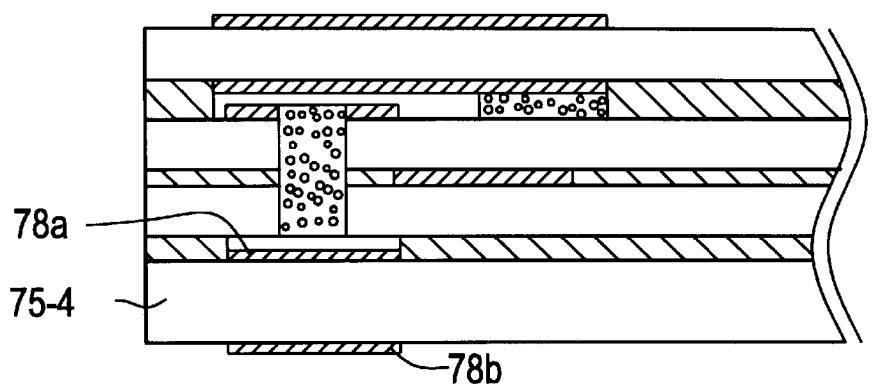
FIG. 43 is a cross-sectional view taken along the long side of a $NO_x$ gas concentration sensor according to a Control Example D for explaining the structure of the sensor.

Conversely, with a sensor of a Control example shown in FIG. 43, in which the electrode 78b is formed outside of the device (sensor), the effective pump voltage acting between the electrodes 78a, 78b of the second oxygen pumping cell 78 is fluctuated to increase oxygen concentration dependency of measurement of the $NO_x$ gas concentration.

The sensor shown in FIG. 38 also has a merit that the electrodes 78a, 78b of the second oxygen pumping cell 78 can be printed at a time.

In addition, the paired electrodes of the first oxygen pumping cell 76, oxygen pumping cell 77 and the second oxygen pumping cell 78 can be connected to outside via interlayer lead portions. In the measurement examples, as later explained, the electrodes 76a, 76b of the first oxygen pumping cell 76 and the electrodes 78a, 78b of the second oxygen pumping cell 78 are connected to a power source and to an ammeter, respectively, while the electrodes 77a, 77b of the oxygen concentration measuring cell 77 is connected to a voltmeter. This configuration is shown in FIG. 7 (=FIG. 7 of our senior JP Patent Application 8-160812).

FIGS. 39 and 40 are a plan view and a cross-sectional view showing a preferred embodiment of the above-described $NO_x$ gas concentration sensor. That is, FIGS. 39 and 40 correspond to the plan view and the cross-sectional views shown by arrows A and B in FIG. 38. The sensor of FIG. 40 differs from the sensor of FIG. 38 in that the lead portion 78d is contacted with the air outside of the sensor (atmosphere or atmosphere of the measuring gas) so that the outside communicates with the electrode 78d via diffusion resistance. The sensor of FIG. 40 differs from the sensor of FIG. 38 in that the porous layer (film) 81 formed between solid electrolyte layers establishes communication between the leads 78c and 78d and in that oxygen pumped out by the second oxygen pumping cell is recycled to the second measuring chamber 74 via the porous layer (film) 81 and the porous lead portion 78c and electrode 78a.

Figure 41:
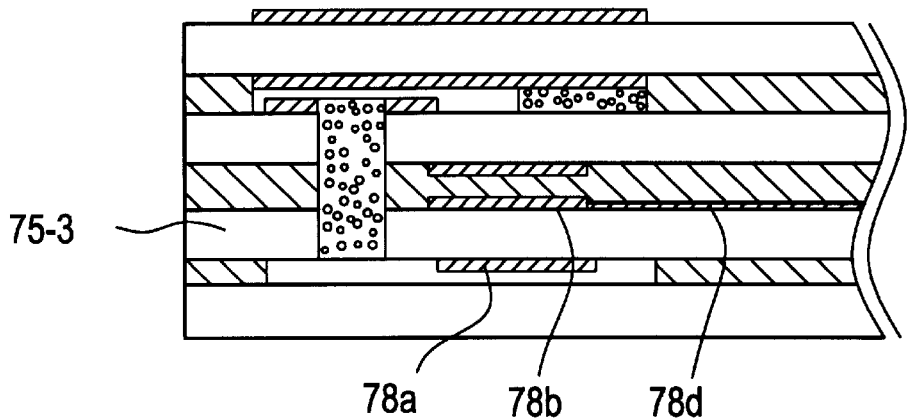
FIG. 41 is a cross-sectional view taken along the long side of a $NO_x$ gas concentration -sensor according to another variant of the present invention for explaining the structure of the sensor.
Figure 42:
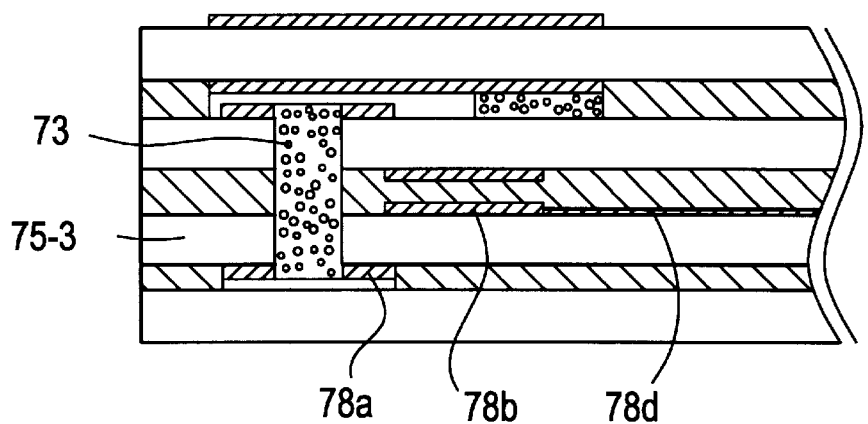
FIG. 42 is a cross-sectional view taken along the long side of a $NO_x$ gas concentration sensor according to a further variant of the present invention for explaining the structure of the sensor.

Referring to FIGS. 41 to 43, a $NO_x$ gas concentration sensor according to another embodiment of aspect D is explained.

Example D2

FIG. 41 illustrates the structure of the $NO_x$ gas sensor according to another example of the present aspect. The sensor shown in FIG. 41 differs from the sensor of Example D1 in that the paired electrodes 78a and 78b of the second oxygen pumping cell 78 are provided symmetrically on both sides of the solid electrolyte layer (cell) 75-3 defining an upper portion of the second measuring chamber 74, with the oxygen pumping-out electrode 78b being electrically connected to the porous electrode portion 78d. The lead portion 78d may be communicated to outside air, while the pumping-out side electrode 78b is electrically connected to the porous lead portion 78d. The lead portion 78d may be connected to outside air, or connected to the first chamber 72 or to the second measuring chamber 74 by through-holes or porous holes as shown in FIGS. 38 or 39. By such configuration, the lowermost solid electrolyte layer in the drawing can be replaced by a layer formed of another material.

Example D3

FIG. 42, illustrating the structure of a $NO_x$ gas concentration sensor according to another embodiment of the present invention, is a cross-sectional view taken along the long side of the sensor. The sensor shown in FIG. 42 differs from the sensor of Example D2 in that the electrode 78a of the second oxygen pumping cell 78 in the second measuring chamber 74 is formed around or in the vicinity of the second diffusion aperture 73 and in that the second measuring chamber 74 is of reduced volume. The sensor of Example D3 is otherwise the same in structure as the sensor of Example D2.

Using the $NO_x$ gas concentration sensors of the Examples D1 to D3 and Control example, tests were conducted for measuring the NO gas concentration in the measuring gas. First referring to FIG. 46, a manufacturing example of the sensor used for measurement is explained. FIG. 46 illustrates a manufacturing example and the layout of the sensor used for measurement.

Manufacturing Example D

Referring to FIG. 46, a previous process A1 (steps 1 to 21) excluding step 13 are basically the same as that of the manufacturing example A shown in FIG. 22. In the present manufacturing example, the step 13d replaces step 13. Next to the last step 21 of the previous process A1, the (D) process 22d to 25d shown in FIG. 46 is added. According to the combination of FIG. 22 and FIG. 46, $ZrO_2$ green sheets, electrode pastes and so forth are layered from upper left to lower left, upper right and to lower right (FIG. 22) to complete a unitary sensor. The insulating coats and paste materials, such as electrodes, are layered by screen printing on a pre-set $ZrO_2$. Next, a manufacturing example of component parts, such as $ZrO_2$ green sheets, is explained. The pores of the porous material shown in FIG. 38 are produced using the process and materials which are the same as those for the first diffusion aperture or the second diffusion aperture of the manufacturing example A. The porous layer or film shown in FIG. 40 is manufactured using the materials and the process which are the same as those of the first diffusion aperture or the second diffusion aperture of the manufacturing example A.

Namely, sheet forming of $ZrO_2$, printing paste, pellets, laminating method of $ZrO_2$, removal of organic binder and sintering are carried out in the same manner as the manufacturing example A.

Test Example D

Using the $NO_x$ gas concentration sensor of Examples D1 to D3 and Control example, tests were conducted for measuring the NO gas concentration in the measuring gas. The sensor used for measurement has a length along its long side of 50 mm, a width (along its short side) of 4 mm and a thickness (in the laminating direction) of 1.3 mm. The first oxygen pumping cell has a thickness of 0.3 mm, the length in the long-side direction and that in the short side direction of the electrodes 6a, 6b are 7 mm and 2 mm, respectively, the length in the long-side direction and that in the short side direction of the first measuring chamber are 7 mm and 2 mm, respectively, with a height being 50 μm. The length in the long-side direction and that in the short side direction of the second measuring chamber are 7 mm and 2 mm, respectively, with a height being 50 μm, for Examples D1 to D3. The length in the long-side direction and that in the short side direction of the second measuring chamber are 2 mm and 2 mm, respectively, with a height being 50 μm, for Examples D1 and D3, while the length in the long-side direction of the second measuring chamber is 7 mm; the length along the long side and that along the short side of the first diffusion aperture are 2 mm and 1 mm, respectively, with a thickness of 50 μm, and the second diffusion aperture being of a diameter of 1 mm, for Example D2.

TABLE D1

Relation between Oxygen Concentration and Ip2 Offset

| Oxygen Concentration(%) | Ip2 Offset (μA) | | | |
|---|---|---|---|---|
| | Example 1 | Example 2 | Example 3 | Comparative Example |
| 16 | 3.65 | 2.43 | 2.75 | 5.33 |
| 7 | 3.95 | 2.54 | 2.63 | 8.31 |
| 1 | 4.14 | 2.99 | 2.69 | 14.53 |
| 0.5 | 4.15 | 3.11 | 2.83 | 20.02 |
| 0 | 4.03 | 3.24 | 2.65 | 50.51 |

TABLE D2

Relation between Oxygen Concentration and Gain(Δ Ip2)

| Oxygen Concentration(%) | Δ Ip2 Offset (μA) | | | |
|---|---|---|---|---|
| | Example 1 | Example 2 | Example 3 | Comparative Example |
| 16 | 12.74 | 12.5 | 13.75 | 12.65 |
| 7 | 11.93 | 11.84 | 12.8 | 11.66 |
| 1 | 11.39 | 11.45 | 12.19 | 10.51 |
| 0.5 | 11.32 | 11.41 | 12.09 | 9.68 |
| 0 | 11.15 | 11.33 | 11.98 | 4.59 |

Test Examples D

Using the $NO_x$ gas concentration sensors of Examples D1 to D3 and Control example, tests were conducted on measuring the NO gas concentration in the measuring gas. The measured results are shown in Tables D1 and D2 and are shown in summary in FIGS. 44 and 45. The measurement conditions common to the test examples as later explained include measuring gas components NO, $O_2$ and $CO_2$ of 0 and 1500 ppm, 0 to 16% and 10%, respectively, with the balance being $N_2$, exhaust gas (measuring gas) temperature of 300° C. and the heater power of 18 W.

Test Example D1

(1) For various values of the oxygen concentration and for NO: 0%, fluctuations in the offset value of the second oxygen pumping current $Ip_2$ were measured. The offset is the amount of $Ip_2$ when NO is not charged into the measuring gas and is equivalent to the concentration of residual oxygen left unpumped in the first measuring chamber. A smaller value of the offset is preferred. It is desirable for the offset to be less sensitive to various extraneous conditions, such as oxygen concentration in the measuring gas or temperature in the measuring gas atmosphere and hence less susceptible to fluctuations.

Figure 44:
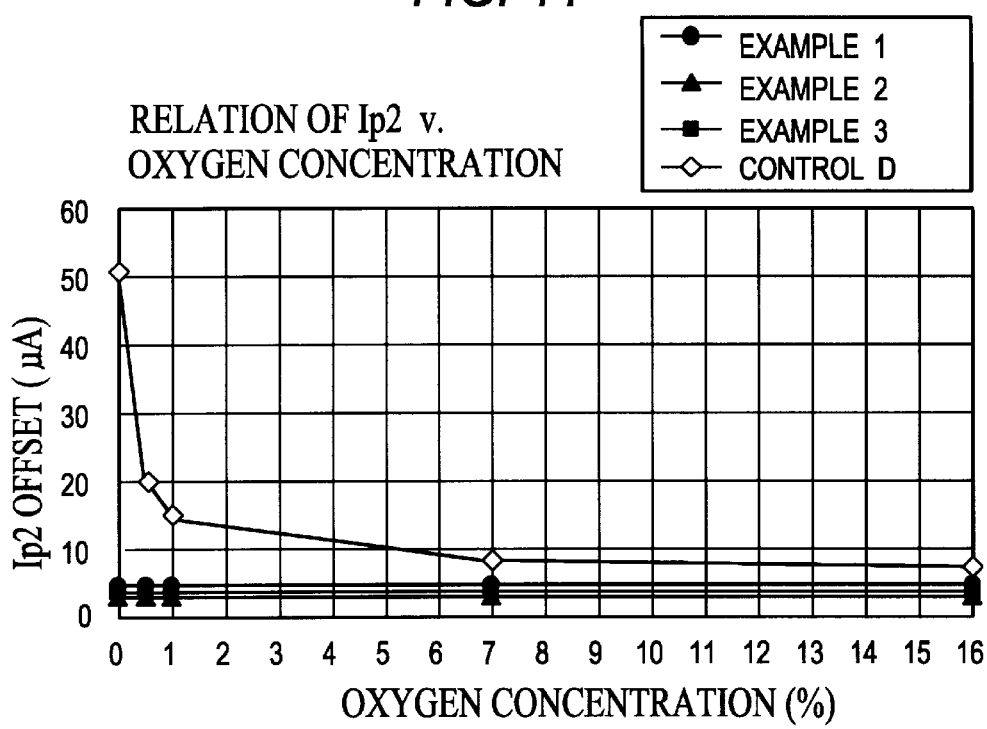
FIG. 44 is a graph showing oxygen concentration dependency of the offset of the second oxygen pumping cell current $Ip_2$, where circular, triangular, square and diamond-shaped plots represent measurement data by the sensors of Examples D1, D2 and D3 and Control Example D.

FIG. 44 shows the results of the test example D1. In FIG. 44, which is a graph showing oxygen concentration dependency of the $Ip_2$ offset, circular, triangular, square and diamond marks denote measured data by the sensors of Examples D1, D2 and D3 and the Control example, respectively. Referring to FIG. 44, the sensors of Examples D1 to D3 undergo in $Ip_2$ offset changes of 1 μA or less versus the varied range of 1 to 16% of the oxygen concentration, thus indicating that the oxygen concentration dependency has been significantly improved (reduced) in particular on the low oxygen concentration side.

Test Example D2

(2) NO was charged at 1500 ppm into a measuring gas and the gain of the current $Ip_2$ flowing in the second pumping cell for the oxygen was measured. The gain is a change in $Ip_2$ on charging NO of a pre-set concentration in the present test example, difference in $Ip_2$ value on charging 0 ppm NO and 1500 ppm NO. For raising the measurement sensitivity for the $NO_x$ gas concentration, a higher value of the $Ip_2$ gain is desirable. It is desirable for the gain to be less sensitive to various extraneous conditions, such as oxygen concentration or temperature in the measuring gas atmosphere and hence less susceptible to fluctuations.

Figure 45:
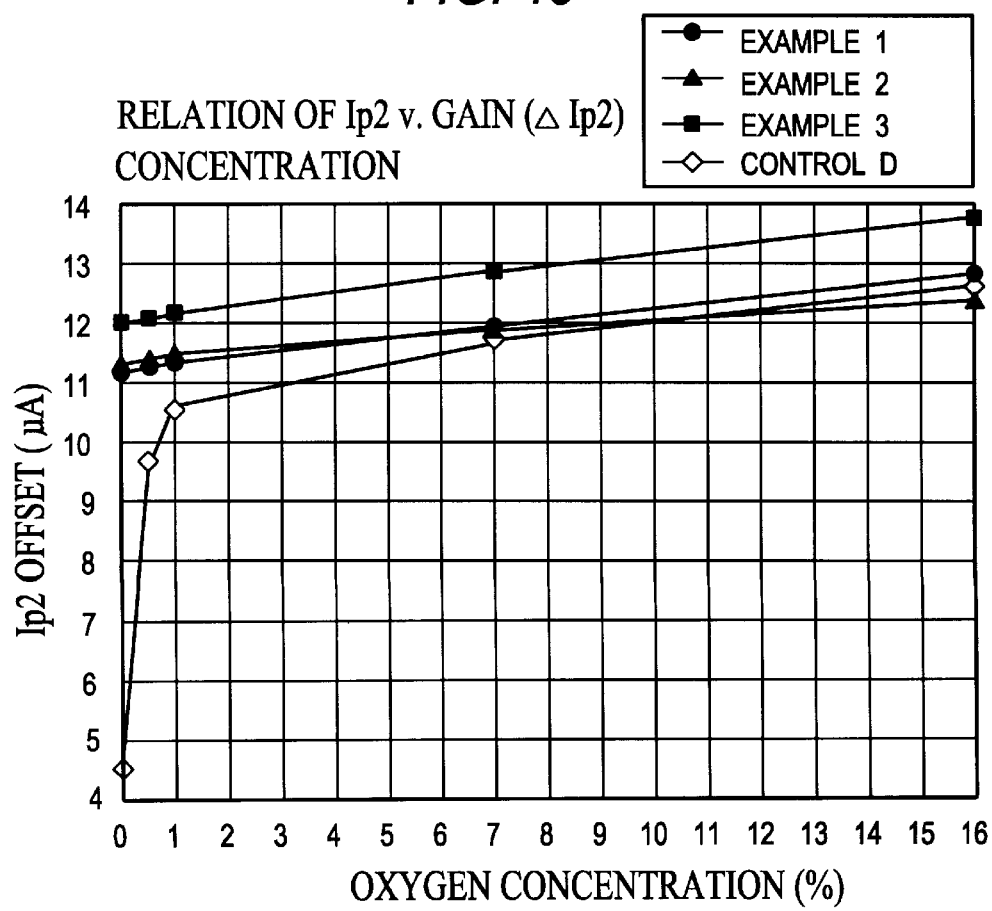
FIG. 45 is a graph showing oxygen concentration dependency of the offset of the second oxygen pumping cell current $\Delta Ip_2$ (Ip2 gain), wherein circular, triangular, square and diamond-shaped plots represent measurement data by the sensors of Examples 1, 2 and 3 and Control Example D, respectively.

FIG. 45 shows results of the test example D2. In FIG. 45, which is a graph showing oxygen concentration dependency of $\Delta IP_2$ ($Ip_2$ gain), circular, triangular, square and diamond marks denote measured data by the sensors of Examples D1, D2 and D3 and the Control example D, respectively. Referring to FIG. 45, $Ip_2$ gain changes are not more than 2 μA versus the varied range of 1 to 16% of the oxygen concentration, thus indicating that the oxygen concentration dependency is smaller than in the case of Control example. It is also seen that the $Ip_2$ gain is higher especially on the low oxygen concentration side than in the case of the Control example, indicating improved sensitivity (resolution) in measurement of the $NO_x$ gas concentration.

With the $NO_x$ gas concentration sensor of the present aspect D, the electromotive force generated across the electrodes of the second oxygen pumping cell is stabilized, thus enabling more accurate $NO_x$ gas concentration measurement in particular in the low oxygen concentration atmosphere. Thus, the present sensor is superior as a sensor for a gasoline engine emitting an exhaust gas of a low oxygen concentration or an internal combustion engine fluctuated significantly in the air/fuel ratio.

The present invention is not limited to examples which are given only by way of illustration. These examples may be modified within a range tolerated by the gist and claimed scope of the invention.

What is claimed is:

1. A sensor for measuring nitrogen oxide concentration, comprising:
    (a) different first, second and third solid electrolyte cells in a lamination;
    (b) an insulating layer being interposed between the first and second solid electrolyte cells; and
    (c) another insulating layer being interposed between the second and third solid electrolyte cells;
    wherein
    (d) a first cavity is provided with the first electrolyte cell as a first oxygen pumping cell and the second electrolyte cell as an oxygen concentration measuring cell, said first and second electrolyte cells each having a solid electrolyte layer and having a pair of porous electrodes, one of said electrodes of the first electrolyte cell facing said cavity;
    (e) a second cavity is provided with the third electrolyte cell as a second oxygen pumping cell having a solid electrolyte layer and a pair of porous electrodes;
    (f) a volume of the first cavity is more than two times the volume of the second cavity;
    (g) a diffusion path for diffusing the nitrogen oxide from the first cavity to the second cavity is formed penetrating through the second electrolyte cell;
    (h) one of said electrodes of the second electrolyte cell that measures oxygen concentration is located around an inlet of the diffusion path; and
    (i) the electrode of the first electrolyte cell facing the first cavity is extended along the solid electrolyte layer of the first cell in a direction toward but not reaching an area immediately above the inlet of the diffusion path.

2. The sensor for measuring nitrogen oxide concentration as claimed in claim 1, wherein
    a length of the electrode of the first electrolyte cell facing the first cavity is from ¼ to ¾ of the length of the first cavity when the length is determined by measuring along an inside wall of the first electrolyte cell in a flowing direction of the gas inside the first cavity.

3. A sensor for measuring $NO_x$ gas concentration comprising:
    (a) a first measuring chamber in which a measuring gas is introduced via a first diffusion resistance;
    (b) an oxygen partial pressure measuring electrode making up an oxygen measuring cell for measuring oxygen partial pressure in the measuring gas in said first measuring chamber;
    (c) a first oxygen pumping cell pumping a sufficient amount of oxygen in said measuring gas out of said first measuring chamber, based on a potential of said oxygen partial pressure measuring electrode, to such an extent as substantially not to cause decomposition of $NO_x$ in said measuring gas;
    (d) a second measuring chamber into which the gas is introduced out of said first measuring chamber via a second diffusion resistance; and
    (e) a second oxygen pumping cell across which a voltage is impressed for decomposing $NO_x$ in said second measuring chamber, with a current flowing therein based on the dissociated oxygen in an amount corresponding to the $NO_x$ gas concentration;
    (f) wherein an insulating layer is interposed between the first oxygen pumping cell and the oxygen measuring cell, and
    (g) another insulating layer is interposed between the oxygen measuring cell and the second oxygen pumping cell;
    wherein
    (h) said first diffusion resistance and said second diffusion resistance are arranged at a spacing from each other with respect to said first measuring chamber;
    (i) an electrode of the first oxygen pumping cell facing the first measuring chamber and an inlet opening of said second diffusion resistance are disposed on opposing surfaces of the first measuring chamber, respectively; and
    (j) wherein the electrode of the first oxygen pumping cell facing the first measuring chamber is extended from the vicinity of said first diffusion resistance to a location not reaching the immediately above area of the inlet opening of the second diffusion resistance.

4. The sensor for measuring $NO_x$ gas concentration as defined in claim 3, wherein said cells are disposed in lamination;
    wherein said second diffusion resistance is formed as a path penetrating said oxygen partial pressure measuring electrode; and
    wherein said oxygen partial pressure measuring electrode is disposed around said inlet of the second diffusion resistance path.

5. The sensor for measuring $NO_x$ gas concentration as defined in claim 3, wherein the first measuring chamber has a volume more than two times the volume of the second measuring chamber.

6. The sensor for measuring $NO_x$ gas concentration as defined in claim 3, wherein a ratio of the length of the electrode of the first oxygen pumping cell facing the first measuring chamber to an overall length of said first measuring chamber in the flowing direction of the measuring gas in said first measuring chamber is given by (electrode/overall length)=¼ to ¾.

7. A senor for measuring nitrogen oxide concentration made up of laminated solid electrolyte layers, comprising:
    (a) a first cavity including a first oxygen pumping cell and an oxygen concentration measuring cell, said first oxygen pumping cell having a solid electrolyte layer and a pair of porous electrodes, one of said electrodes facing said first cavity;
    (b) a second cavity including a second oxygen pumping cell having a solid electrolyte layer and a pair of porous electrodes;

(c) a first diffusion path communicating said first cavity with a measuring gas, and (d) a second diffusion path communicating said first cavity with said second cavity, wherein (e) said first oxygen pumping cell, oxygen concentration measuring cell and the second oxygen pumping cell are disposed in a different solid electrolyte layer from each other and (f) the electrode of the first oxygen pumping cell facing the first cavity is extended along the solid electrolyte layer of the first oxygen pumping cell in a direction toward but not reaching an area immediately above an inlet of the second diffusion path.

8. A sensor for measuring nitrogen oxide concentration made up of laminated solid electrolyte layers, comprising:

(a) a first cavity including a first oxygen pumping cell and an oxygen concentration measuring cell, said first oxygen pumping cell having a solid electrolyte layer and a pair of porous electrodes, one of said electrodes facing said first cavity;

(b) a second cavity including a second oxygen pumping cell having a solid electrolyte layer and a pair of porous electrodes;

(c) a first diffusion path communicating said first cavity with a measuring gas, and (d) a second diffusion path communicating said first cavity with said second cavity, wherein (e) said first oxygen pumping cell, oxygen concentration measuring cell and the second oxygen pumping cell are disposed in a different solid electrolyte layer from each other, (f) the electrode of the first oxygen pumping cell facing the first cavity is extended along the solid electrolyte layer of the first cell in a direction toward but not reaching an area immediately above the inlet of the second diffusion path, and (g) a length of the electrode of the first oxygen pumping cell facing the first cavity is from ¼ to ¾ of the length of the first cavity when the length is determined by measuring along an inside wall of the first oxygen pumping cell in a flowing direction of the gas inside the first cavity.

9. The sensor of claim 7, wherein an insulating layer is interposed between the first oxygen pumping cell and the oxygen concentration measuring cell, and another insulating layer is interposed between said oxygen concentration measuring cell and the second oxygen pumping cell.

10. The sensor of claim 7, wherein said first oxygen pumping cell pumps a sufficient amount of oxygen from the first cavity into a measuring gas such that the amount of oxygen does not cause a substantial decomposition of NOx in said measuring gas.

11. The sensor of claim 7, wherein said oxygen concentration measuring cell has a porous electrode facing the first cavity disposed in the vicinity of said inlet of the second diffusion path.

12. The sensor of claim 7, wherein a diffusion resistance is disposed within the second diffusion path.

* * * * *